(12) United States Patent
Sigurdsson

(10) Patent No.: US 10,859,582 B2
(45) Date of Patent: *Dec. 8, 2020

(54) TAU IMAGING LIGANDS AND THEIR USES IN THE DIAGNOSIS AND TREATMENT OF TAUOPATHY

(71) Applicant: New York University, New York, NY (US)

(72) Inventor: Einar M. Sigurdsson, Scarsdale, NY (US)

(73) Assignee: New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/151,555

(22) Filed: Oct. 4, 2018

(65) Prior Publication Data

US 2019/0025331 A1    Jan. 24, 2019

Related U.S. Application Data

(63) Continuation of application No. 15/324,141, filed as application No. PCT/US2015/039205 on Jul. 6, 2015, now Pat. No. 10,132,818.

(60) Provisional application No. 62/021,897, filed on Jul. 8, 2014.

(51) Int. Cl.
| | |
|---|---|
| *G01N 33/68* | (2006.01) |
| *C07K 16/18* | (2006.01) |
| *A61K 49/00* | (2006.01) |
| *A61K 38/00* | (2006.01) |

(52) U.S. Cl.
CPC ..... *G01N 33/6896* (2013.01); *A61K 49/0058* (2013.01); *C07K 16/18* (2013.01); *A61K 38/00* (2013.01); *C07K 2317/30* (2013.01); *C07K 2317/34* (2013.01); *C07K 2317/622* (2013.01); *C07K 2317/92* (2013.01); *G01N 2440/14* (2013.01); *G01N 2800/2821* (2013.01)

(58) Field of Classification Search
CPC ........... G01N 33/6896; G01N 2440/14; G01N 2800/2821; A61K 49/0058; A61K 38/00; C07K 16/18; C07K 2317/34; C07K 2317/92; C07K 2317/30; C07K 2317/622; A61P 25/28; A61P 25/16; A61P 25/00; A61P 21/02

See application file for complete search history.

(56) References Cited

U.S. PATENT DOCUMENTS

| | | | |
|---|---|---|---|
| 4,179,337 A | 12/1979 | Davis et al. | |
| 4,495,285 A | 1/1985 | Shimizu et al. | |
| 4,609,546 A | 9/1986 | Hiratani | |
| 4,681,581 A | 7/1987 | Coates | |
| 4,735,210 A | 4/1988 | Goldenberg | |
| 4,766,106 A | 8/1988 | Katre et al. | |
| 4,861,581 A | 8/1989 | Epstein et al. | |
| 5,101,827 A | 4/1992 | Goldenberg | |
| 5,102,990 A | 4/1992 | Rhodes | |
| 5,225,539 A | 7/1993 | Winter | |
| 5,434,050 A | 7/1995 | Maggio | |
| 5,530,101 A | 6/1996 | Queen et al. | |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,569,825 A | 10/1996 | Lonberg et al. | |
| 5,580,717 A | 12/1996 | Dower et al. | |
| 5,585,089 A | 12/1996 | Queen et al. | |
| 5,589,466 A | 12/1996 | Felgner et al. | |
| 5,625,126 A | 4/1997 | Lonberg et al. | |
| RE35,500 E | 5/1997 | Rhodes | |
| 5,633,425 A | 5/1997 | Lonberg et al. | |
| 5,648,471 A | 7/1997 | Buttram et al. | |
| 5,661,016 A | 8/1997 | Lonberg et al. | |
| 5,670,477 A | 9/1997 | Poduslo et al. | |
| 5,697,902 A | 12/1997 | Goldenberg | |

(Continued)

FOREIGN PATENT DOCUMENTS

| | | |
|---|---|---|
| WO | WO 1992/003918 | 3/1992 |
| WO | WO 1992/022645 | 12/1992 |

(Continued)

OTHER PUBLICATIONS

Paul W. E. Fundamental Immunology, 3rd edition, 1993, pp. 292-295.*

(Continued)

*Primary Examiner* — Gregory S Emch

(74) *Attorney, Agent, or Firm* — Jeffrey I. Auerbach; AuerbachSchrot LLC

(57) ABSTRACT

The present invention relates to antibody-based probes (including single domain antibody fragment, scFv molecules, antibodies, antibody fragments, diabodies, and the epitope-binding domains thereof) that are capable of immunospecifically and selectively binding to a phosphoserine-containing epitope of Tau, such as, for example, Tau-phospho-serine 396/404 peptide. Such imaging ligands are useful to detect pathological Tau protein conformer if present in a biological sample, especially in conjunction with the diagnosis of Alzheimer's disease or other tauopathy, and thus provide a diagnostic for Alzheimer's disease and other Tau pathologies. The scFv molecules of the present invention have utility as diagnostic markers for, Alzheimer's disease and related tauopathies and as pharmaceutical compositions for the treatment of such conditions.

20 Claims, 14 Drawing Sheets

Specification includes a Sequence Listing.

(56) References Cited

U.S. PATENT DOCUMENTS

| | | | |
|---|---|---|---|
| 5,721,106 A | 2/1998 | Maggio | |
| 5,733,743 A | 3/1998 | Johnson et al. | |
| 5,741,957 A | 4/1998 | Deboer et al. | |
| 5,750,172 A | 5/1998 | Meade et al. | |
| 5,756,687 A | 5/1998 | Denman et al. | |
| 5,770,429 A | 6/1998 | Lonberg et al. | |
| 5,789,650 A | 8/1998 | Lonberg et al. | |
| 5,814,318 A | 9/1998 | Lonberg et al. | |
| 5,827,690 A | 10/1998 | Meade et al. | |
| 5,837,473 A | 11/1998 | Maggio et al. | |
| 5,859,205 A | 1/1999 | Adair et al. | |
| 5,874,299 A | 2/1999 | Lonberg et al. | |
| 5,877,397 A | 3/1999 | Lonberg et al. | |
| 5,973,972 A | 10/1999 | Kwon et al. | |
| 6,077,835 A | 6/2000 | Hanson et al. | |
| 6,207,153 B1 | 3/2001 | Dan et al. | |
| 6,265,150 B1 | 7/2001 | Terstappen et al. | |
| 6,407,213 B1 | 6/2002 | Carter et al. | |
| 6,471,960 B1 | 10/2002 | Anderson | |
| 6,821,504 B2 | 11/2004 | Wisniewski et al. | |
| 6,881,557 B2 | 4/2005 | Foote | |
| 7,446,180 B2 | 11/2008 | Novak | |
| 8,012,936 B2 | 9/2011 | Sigurdsson et al. | |
| 8,748,386 B2 | 6/2014 | Sigurdsson | |
| 9,139,643 B2 | 9/2015 | Sigurdsson | |
| 2003/0147811 A1 | 8/2003 | Wisniewskki et al. | |
| 2008/0050383 A1 | 2/2008 | Sigurdsson et al. | |
| 2008/0220449 A1 | 9/2008 | Vasan et al. | |
| 2009/0098155 A1 | 4/2009 | Garsky et al. | |
| 2010/0316564 A1 | 12/2010 | Sigurdsson et al. | |
| 2011/0318358 A1 | 12/2011 | Sigurdsson et al. | |

FOREIGN PATENT DOCUMENTS

| | | |
|---|---|---|
| WO | WO 1993/001227 | 1/1993 |
| WO | WO 1993/011231 | 6/1993 |
| WO | WO 1993/012227 | 6/1993 |
| WO | WO 1994/025585 | 11/1994 |
| WO | WO 1998/022120 | 5/1998 |
| WO | WO 1998/024884 | 6/1998 |
| WO | WO 2000/046147 | 8/2000 |
| WO | WO 2000/070087 | 11/2000 |
| WO | WO 2001/009187 | 2/2001 |
| WO | WO 2001/014424 | 3/2001 |
| WO | WO 2002/043478 | 6/2002 |
| WO | WO 2002/064084 | 8/2002 |
| WO | WO 2007/059782 | 5/2007 |
| WO | WO 2010/106127 | 9/2010 |
| WO | WO 2010/115843 | 10/2010 |
| WO | WO 2011/013034 | 2/2011 |

OTHER PUBLICATIONS

Rudikoff et al. Single amino acid substitution altering antigen-binding specificity. Proc Natl Acad Sci USA. Mar. 1982;79(6):1979-83.*

Vajdos et al. Comprehensive functional maps of the antigen-binding site of an anti-ErbB2 antibody obtained with shotgun scanning mutagenesis. J Mol Biol. Jul. 5, 2002;320(2):415-28.*

Adams, G.P. et al. (1998) "*Prolonged in vivo Tumour Retention of a Human Diabody Targeting the Extracellular Domain of Human HER2/neu,*" Brit. J. Cancer 77(9):1405-1412.

Ahmad, Z.A. et al. (2012) "*scFv Antibody: Principles and Clinical Application,*" Clin. Dev. Immunol. 2012:980250.

Alt, M. et al. (1999) "*Novel Tetravalent and Bispecific IgG-like Antibody Molecules Combining Single-Chain Diabodies with the Immunoglobulin □1 Fc or CH3 Region,*" FEBS Lett. 454:90-94.

Altschul, S.F. (1991) "*Amino Acid Substitution Matrices from an Information Theoretic Perspective,*" J. Mol. Biol. 219: 555-565.

Andorfer, C. et al. (2003) "*Hyperphosphorylation and Aggregation of Tau in Mice Expressing Normal Human Tau Isoforms,*" J. Neurochem. 86:582-590.

Asuni, A.A. et al. (2006) "*Tau-Based Immunotherapy for Dementia,*" Alzheimer's & Dementia 2(3):S40-S41 Feb. 5, 2004.

Asuni, A.A. et al. (2007) "*Immunotherapy Targeting Pathological Tau Conformers in a Tangle Mouse Model Reduces Brain Pathology with Associated Functional Improvements,*" J. Neurosci. 27:9115-9129.

Barderas, R. et al. (2008) "*Affinity Maturation of Antibodies Assisted by in Silico Modeling,*" Proc. Natl. Acad. Sci. (USA) 105(26):9029-9034.

Basurto-Islas, G. et al. (2008) "Accumulation of Aspartic Acid(421)- and Glutamic Acid(391-Cleaved Tau in Neurofibrillary Tangles Correlates with Progression in Alzheimer's Disease," J Neuropathol Exp Neurol 67(5):169-179.

Bekris, L.M. et al. (2010) "*Genetics of Alzheimer Disease,*" J. Geriatr. Psychiatry Neurol. 23(4):213-227.

Benvenisty N. et al., "*Direct Introduction of Genes into Rates and Expression of the Genes,*" Proc. Natl. Acad. Sci. (USA) 83: 9551-9555.

Bhaskar, S. et al. (2010) "*Multifunctional Nanocarriers for Diagnostics, Drug Delivery and Targeted Treatment Across Blood-Brain Barrier: Perspectives on Tracking and Neuroimaging,*" Part. Fibre Toxicol. 7(3):1-25.

Bi, M. et al. (2011) "*Tau-Targeted Immunization Impedes Progression of Neurofibrillary Histopathology in Aged P301L Tau Transgenic Mice,*" PLoS One. 6:e26860.

Bibl, M. et al. (2012) "*Neurochemical Biomarkers in Alzheimer's Disease and Related Disorders,*" Ther Adv Neurolog Disorders 5(6):455-476.

Bickel, U. et al. (2001) "*Delivery of Peptides and Proteins Through the Blood-Brain Barrier,*" Adv. Drug Deliv. Rev. 46:247-279.

Bird, R.E. et al. (1988) "*Single-Chain Antigen-Binding Proteins,*" Science 242:423-426.

Bitter, G.A. et al. (1987) "*Expression and Secretion Vectors for Yeast,*" Methods Enzymol. 153, 516-544 (1987).

Blennow, K. et al. (2010) "*Cerebrospinal Fluid and Plasma Biomarkers in Alzheimer Disease,*" Nat. Rev. Neurol. 6: 131-144.

Boado, R.J. et al. (2010) "*IgG-Single Chain Fv Fusion Protein Therapeutic for Alzheimer's Disease: Expression in CHO cells and Pharmacokinetics and Brain Delivery in the Rhesus Monkey,*" Biotechnol. Bioeng. 105:627-635.

Boimel, M. et al. (2010) "*Efficacy and Safety of Immunization with Phosphorylated Tau Against Neurofibrillary Tangles in Mice,*" Exp. Neurol. 224, 472-485.

Bostrom, J. et al. (2009) "*Improving Antibody Binding Affinity and Specificity for Therapeutic Development,*" Methods Mol. Biol. 525:353-376.

Boutajangout, A. et al. (2010) "*Immunotherapy Targeting Pathological Tau Prevents Cognitive Decline in a New Tangle Mouse Model,*" J. Neurosci. 30:16559-16566.

Boutajangout, A. et al. (2011) "*Passive Immunization Targeting Pathological Phospho-Tau Protein in a Mouse Model Reduces Functional Decline and Clears Tau Aggregates From the Brain,*" J. Neurochem. 118:658-667.

Boutajangout, A. et al. (2011) "*Passive Tau Immunotherapy Diminishes Functional Decline and Clears Tau Aggregates in Mouse Model of Tauopahty,*" Alzheimer's & Dementia 6(4):S578:P3-427 (1 page).

Budson, A.E. et al. (2012) "*New Criteria for Alzheimer Disease and Mild Cognitive Impairment: Implications for the Practicing Clinician,*" Neurologist 18(6):356-363.

Calignon A et al. (2010) "*Caspase Activation Precedes and Leads to Tangles,*" Nature 464:1201-1205.

Carrillo, M.C. et al. (2013) "*Revisiting the Framework of the National Institute on Aging-Alzheimer's Association Diagnostic Criteria,*" Alzheimers Dement. 9(5):594-601.

Carter, P. et al. (1992) "*Humanization of an Anti-p185her2 Antibody for Human Cancer Therapy,*" Proc. Natl. Acad. Sci. (U.S.A.) 89:4285-4289.

Castillo-Carranza, D.L. et al. (2014) "*Passive Immunization with Tau Oligomer Monoclonal Antibody Reverses Tauopathy Phenotypes without Affecting Hyperphosphorylated Neurofibrillary Tangles,*" J. Neurosci. 34:4260-4272.

(56) References Cited

OTHER PUBLICATIONS

Castillo-Carranza, D.L. et al. (2014) "Specific Targeting of Tau Oligomers in Htau Mice Prevents Cognitive Impairment and Tau Toxicity Following Injection With Brain-Derived Tau Oligomeric Seeds," J. Alzheimers. Dis. 40:S97-S111.
Chai, X. et al. (2011) "Passive Immunization With Anti-Tau Antibodies in Two Transgenic Models: Reduction of Tau Pathology and Delay of Disease Progression," J. Biol Chem. 286:34457-34467.
Chen, J. et al. (1993) "B Cell Development in Mice that Lack One or Both Immunoglobulin Kappa Light Chain Genes," EMBO J. 12, 821-830.
Chen, J. et al. (1993) "Immunoglobulin gene rearrangement in B cell deficient mice generated by targeted deletion of the JH locus," International Immunology 5:647-656.
Chien, D.T. (2014) "Early Clinical PET Imaging Results with the Novel PHF-Tau Radioligand [F18]-T808," J. Alzheimers. Dis. 38:171-184.
Chien, D.T. et al. (2013) "Early Clinical PET Imaging Results with the Novel PHF-Tau Radioligand [F-18]-T807," J. Alzheimers. Dis. 34:457-468 (1 page Abstract Only).
Chothia, C. et al. (1987) "Canonical Structures for the Hypervariable Regions of Immunoglobulins," J. Mol. Biol. 196:901-917.
Clarivate Analytics, Database WPI 1-14, Week 199245, Thomson Scientific, London, GB; An 1992-369428 XP002778304 & JP H04 270300 A (Mitsubishi Kasei); (1992) (2 pages).
Co, M. S. et al. (1991) "Humanized Antibodies for Antiviral Therapy," Proc. Natl. Acad. Sci. (U.S.A.) 88:2869-2873.
Co, M.S. et al. (1992) "Chimeric and Humanized Antibodies with Specificity for the CD33 Antigen," J. Immunol. 148:1149-1154.
Congdon, E. E. et al. (2013) "Antibody Uptake into Neurons Occurs Primarily via Clathrin-dependent Fcgamma Receptor Endocytosis and Is a Prerequisite for Acute Tau Protein Clearance," J. Biol Chem. 288:35452-35465.
Congdon, E.E. (2014) "Harnessing the Immune System for Treatment and Detection of Tau Pathology," J. Alzheimers Dis. 40:S113-S121.
Corsaro, C.M. et al. (1981) "Enhancing the efficiency of DNA-mediated gene transfer in mammalian cells," Somatic Cell Genetics 7(5):603-616.
D'Abramo, C. et al. (2013) "Tau Passive Immunotherapy in Mutant P301L Mice: Antibody Affinity versus Specificity," PLoS One 8:e62402.
Davis, J. et al. (2004) "Early-Onset and Robust Cerebral Microvascular Accumulation of Amyloid Beta-Protein in Transgenic Mice Expressing Low Levels of a Vasculotropic Dutch/Iowa Mutant Form of Amyloid Beta-Protein Precursor," J Biol Chem 279:20296-20306.
Dincq, S. et al. (2001) "Expression and Purification of Monospecific and Bispecific Recombinant Antibody Fragments Derived From Antibodies That Block the CD80/CD86-CD28 Costimulatory Pathway," Protein Express. Purificat. 22(1):11-24.
Eddy, S.R. (2004) "Where Did the BLOSUM62 Alignment Score Matrix Come From?," Nature Biotechnol. 22(8):1035-1036.
EPO-Provided Machine Translation of JP2916297B B2 Jul. 5, 1999 (1992) (prepared (2017) (7 pages).
Eurasian Patent Search Report Appln No. 201171397 (dated 2012) (4 pages).
Evans et al. (1995) "Rapid expression of an anti-human C5 chimeric Fab utilizing a vector that replicates in COS and 293 cells" J. Immunol. Meth. 184, 123-138.
Extended Search Report EP 17197129.4 (dated Mar. 12, 2018) pp. 1-7.
Fagan, A.M. et al. (2010) "Upcoming Candidate Cerebrospinal Fluid Biomarkers of Alzheimer's Disease," Biomarkers Med 6(4):455-476.
Finlay, W.J. et al. (2009) "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J. Mol. Biol. 388(3):541-558.
Fisher, A. et al. (2009) "Efficient Isolation of Soluble Intracellular Single-Chain Antibodies Using the Twin Arginine Translocation Machinery," J. Mol. Biol. 385(1):299-311.
Fishwild, D.M. et al (1996) "High-avidity human IgGK monoclonal antibodies from a novel strain of minilocus transgenic mice," Nature Biotechnol. 14, 845-851.
Fodero-Tavoletti, M. T. et al. (2011) "18F-THK523: A Novel In Vivo Tau Imaging Ligand for Alzheimer's Disease," Brain 134:1089-1100.
Fodero-Tavoletti, M. T. et al. (2014) "Assessing THK523 Selectivity for Tau Deposits in Alzheimer's Disease and Non-Alzheimer's Disease Tauopathies," Alzheimer's Res. Ther. 6:11.
Fraser, K.J. et al. (1972) "Specific Cleavage Between Variable and Constant Domains of Rabbit Antibody Light Chains by Dilute Acid Hydrolysis," Biochemistry 11(26):4974-4977.
GenBank Accession No. EAW93567 (Dec. 18, 2006).
Glaser, S.M. et al. (1992) "Antibody Engineering by Codon-Based Mutagenesis in a Filamentous Phage Vector System," J. Immunology 149:3903-3913.
Gonzales, N.R. et al. (2004) "SDR Grafting of a Murine Antibody Using Multiple Human Germline Templates to Minimize Its Immunogenicity," Mol. Immunol. 41:863-872.
Gorman, S. D. et al. (1991) "Reshaping a Therapeutic CD4 Antibody" Proc. Natl. Acad. Sci. (U.S.A.) 88:4181-4185.
Gu, J. et al. (2013) "Two Novel Tau Antibodies Targeting the 396/404 Region are Primarily Taken Up by Neurons and Reduce Tau Protein Pathology," J. Biol. Chem. 288(46):33081-33095.
Gustchina, E. et al. (2009) "Affinity Maturation by Targeted Diversification of the CDR-H2 Loop of a Monoclonal Fab Derived From a Synthetic Naïve Human Antibody Library and Directed Against the Internal Trimeric Coiled-Coil of Gp41 Yields a Set of Fabs With Improved HIV-1 Neutralization Potency and Breadth," Virology 393(1):112-119.
Hackel, B.J. et al. (2010) "Stability and CDR Composition Biases Enrich Binder Functionality Landscapes," J. Mol. Biol. 401(1):84-96.
Hales, C.M. et al. (2013) "From Frontotemporal Lobar Degeneration Pathology to Frontotemporal Lobar Degeneration Biomarkers," Int. Rev. Psychiatry 25:210-220.
Hanes, et al. (1997) "New advances in microsphere-based single-dose vaccines," Advanced Drug Delivery Reviews 28:97-119.
Harada, R., et al. (2013) "Comparison of the Binding Characteristics of [18F]THK-523 and Other Amyloid Imaging Tracers to Alzheimer's Disease Pathology," Eur. J. Nucl. Med. Mol. Imaging 40:125-132.
Harding, F., et al. (1995) "Class Switching in Human Immunoglobulin Transgenic Mice," Ann. N. Y. Acad. Sci. 764 536-546.
Hasegawa, M. et al. (1993) "Characterization of Two Distinct Monoclonal Antibodies to Paired Helical Filaments: Further Evidence for Fetal-Type Phosphorylation of the Tau in Paired Helical Filaments," J. Neurochem. 60(6):2068-2077.
Henikoff, J.G. et al. (1992) "Amino acid substitution matrices from protein blocks," Proc. Natl. Acad. Sci. (USA) 89:10915-10919.
Hervé, F. et al. (2008) "CNS Delivery via Adsorptive Transcytosis," AAPS J. 10(3):455-472.
Hoffmann R. et al. (1997) "Unique Alzheimer's Disease Paired Helical Filaments Specific Epitopes Involve Double Phosphorylation at Specific Sites," Biochemistry 36(26):8114-8124.
Hollinger, P. et al. (1993) "Diabodies: Small Bivalent and Bispecific Antibody Fragments," Proc. Natl. Acad. Sci. (U.S.A.) 90(14):6444-6448.
Holt L.J. et al. (2003) "Domain antibodies: proteins for therapy," Trends Biotechnol. 21(11):484-490.
Huang, L. et al. (2013) "Single-Chain Fragment Variable Passive Immunotherapies for Neurodegenerative Diseases," Int. J. Mol. Sci. 14(9):19109-19127.
Huhalov, A. et al. (2004) "Engineered Single Chain Antibody Fragments for Radioimmunotherapy," Q. J. Nucl. Med. Mol. Imaging 48(4):279-288.
Husain, M.M. (2005) "Clinical Diagnosis and Management of Alzheimer's Disease," Neuroimag. Clin. N. Am. 15(4):767-777.
Hussein, A.H. et al. (2007) "Construction and Characterization of Single-Chain Variable Fragment Antibodies Directed against the

(56) References Cited

OTHER PUBLICATIONS

*Bordetella pertussis Surface Adhesins Filamentous Hemagglutinin and Pertactin,*" Infect. Immun. 75(11):5476-5482.

Huston, J.S. et al. (1988) "*Protein Engineering of Antibody Binding Sites: Recovery of Specific Activity in an Anti-Digoxin Single-Chain Fv Analogue Produced in Escherichia coli,*" Proc. Natl. Acad. Sci. (U.S.A.) 85:5879-5883.

International Search Report PCT/US2010/038184 (WO 2010/144711) (dated 2011) (7 pages).

International Search Report PCT/US2015/039205 (WO 2016/007414) (dated 2015) (4 pages).

Jevsevar, S. et al. (2010) "*PEGylation of Therapeutic Proteins,*" Biotechnol. J. 5(1):113-228.

Johnson, G.V.W. et al. (2004) "*Tau Phosphorylation in Neuronal Cell Fraction and Dysfunction,*" J Cell Sci 117(24):5721-5729.

Jones, A.R. et al. (2007) "*Blood-Brain Barrier Transport of Therapeutics via Receptor-Mediation,*" Pharm. Res. 24(9):1759-1771.

Kandimalla, K.K. et al. (2006) "*Physiological and Biophysical Factors That Influence Alzheimer's Disease Amyloid Plaque Targeting of Native and Putrescine Modified Human Amyloid Beta40,*" J. Pharmacol. Exp. Ther. 318:17-25.

Karlin, S. et al. (1990) "*Methods for Assessing the Statistical Significance of Molecular Sequence Features by Using General Scoring Schemes,*" Proc. Natl. Acad. Sci. (USA) 87:2264-2268.

Kaur, S. et al. (2012) "*Recent Trends in Antibody-Based Oncologic Imaging,*" Cancer Lett. 315(2):97-111.

Kettleborough, C. A. et al. (1991) "*Humanization of a Mouse Monoclonal Antibody by CDR-Grafting: The Importance of Framework Residues on Loop Conformation,*" Protein Engineering 4:773-783.

Kfoury, N. et al. (2012) "*Trans-cellular Propagation of Tau Aggregation by Fibrillar Species,*" J. Biol. Chem. 287:19440-19451.

Knopman, D.S. et al. (2001) "*Practice Parameter: Diagnosis of Dementia (An Evidence-Based Review) Report of the Quality Standards Subcommittee of the American Academy of Neurology,*" Neurology 56:1143-1153.

Krause, J.C. et al. (2011) "*An Insertion Mutation That Distorts Antibody Binding Site Architecture Enhances Function of a Human Antibody,*" MBio. 2(1) pii: e00345-10. doi: 10.1128/mBio.00345-10.

Krishnamurthy, P.K. et al. (2009) "*Immunotherapy Targeting Alzheimer's Phospho-Tau Epitope Within the Microtubule Binding Region of Tau Clears Pathological Tau and Prevents Functional Decline in a Mouse Model of Tauopathy,*" Alzheimer's & Dementia: The Journal of the Alzheimer's Association 5(4):P112 Feb. 5, 2001 (1 page).

Krishnamurthy, P.K. et al. (2011) "*Mechanistic Studies of Antibody-Mediated Clearance of Tau Aggregates Using an Ex Vivo Brain Slice Model,*" Front. Psychiatry 2:59.

Krishnaswamy S. et al. (2014) "*Antibody-Derived in vivo Imaging of Tau Pathology,*" J. Neurosci. 34:16835-16850.

Krishnaswamy, S. et al. (2009) "*Cloning Antifungal Single Chain Fragment Variable Antibodies by Phage Display and Competitive Panning Elution,*" Anal. Biochem. 395:16-24.

Krishnaswamy, S. et al. (2011) "*Isolation and Characterization of Recombinant Single Chain Fragment Variable Anti-Idiotypic Antibody Specific to Aspergillus fumigatus Membrane Protein,*" J. Immunol. Methods 366:60-68.

Kuan, C.T. et al. (2010) "*Affinity Matured Anti-Glycoprotein NMB Recombinant Immunotoxins Targeting Malignant Gliomas and Melanomas,*" Int. J. Cancer 10.1002/ijc.25645.

Kufer, P. et al. (2004) "*A Revival of Bispecific Antibodies,*" Trends Biotechnol. 22(5):238-244.

Kurth, M. et al. (1993) "*Site-Specific Conjugation of a Radioiodinated Phenethylamine Derivative to a Monoclonal Antibody Results in Increased Radioactivity Localization in Tumor,*" J. Med. Chem. 36(9):1255-1261.

Lajoie, J.M. et al. (2015) "*Targeting Receptor-Mediated Transport for Delivery of Biologics Across the Blood-Brain Barrier,*" Annu Rev. Pharmacol. Toxicol. 55:613-631.

Langer, R. et al. (1990) "*New Methods of Drug Delivery,*" Science 249:1527-1533.

Le Gall, F. et al. (1999) "*Di-, Tri- and Tetrameric Single Chain Fv Antibody Fragments Against Human CD19: Effect of Valency on Cell Binding,*" FEBS Letters 453(1):164-168.

Lemere, C.A. et al. (2010) "*Can Alzheimer Disease Be Prevented by Amyloid-Beta Immunotherapy?,*" Nat. Rev. Neurol. 6:108-119.

Lewis, J. et al. (2000) "*Neurofibrillary Tangles, Amyotrophy and Progressive Motor Disturbance in Mice Expressing Mutant (P301L) Tau Protein,*" Nat. Genet. 25, 402-405.

Lindegren, S. et al. (1998) "*Chloramine-T in High-Specific-Activity Radioiodination of Antibodies Using N-Succinimidyl-3-(Trimethylstannyl)Benzoate as an Intermediate,*" Nucl. Med. Biol. 25(7):659-665.

LoBuglio, A.F. et al. (1989) "*Mouse/Human Chimeric Monoclonal Antibody in Man: Kinetics and Immune Response,*" Proc. Natl. Acad. Sci. (U.S.A.) 86:4220-4224.

Lonberg, N. et al. (1994) "*Antigen-specific human antibodies from mice comprising four distinct genetic modifications,*" Nature 368:856-859.

Lonberg, N. et al. (1995) "*Human antibodies from transgenic mice*", Intern. Rev. Immunol. 13:65-93.

Maeda, H. et al. (1991) "*Construction of Reshaped Human Antibodies with HIV-Neutralizing Activity,*" Hum. Antibod. Hybridomas 2:124-134.

Maggio, J.E. et al. (1992) "*Reversible in Vivo Growth of Alzheimer Disease b-Amyloid Plaques by Deposition of Labeled Amyloid Peptide,*" Proc Natl Acad Sci U.S.A. 89:5462-5466.

Maruyama, M.H. et al. (2013) "*Imaging of Tau Pathology in a Tauopathy Mouse Model and in Alzheimer Patients Compared to Normal Controls,*" Neuron 79:1094-1108.

Mason, N.S. et al. (2013) "*Positron Emission Tomography Radioligands for In Vivo Imaging of ABeta Plaques,*" J. Labelled Comp. Radiopharm. 56:89-95.

Mathupala, S.P. et al. (2009) "*Delivery of Small-Interfering RNA (siRNA) to the Brain,*" Expert Opin. Ther. Pat. 19(2):137-140.

Montgomery, D.L. et al. (2009) "*Affinity Maturation and Characterization of a Human Monoclonal Antibody Against HIV-1 gp41,*" mAbs 1(5):462-474.

Moosmann, A. et al. (2014) "*Purification of PEGylated Proteins, with the Example of PEGylated Lysozyme and PEGylated scFv,*" Methods Mol. Biol. 1129:527-538.

Müller, M.R. et al. (2012) "*Improving the Pharmacokinetic Properties of Biologics by Fusion to an Anti-HSA Shark VNAR Domain,*" mAbs. 4(6):673-685.

Novak, M. (1994) "*Truncated Tau Protein as a New Marker for Alzheimer's Disease,*" Acta Virologica 38:173-189.

Novak, M. (2009) "*Tau Vaccine Active Immunization with Misfolded Tau Protein Attenuates Tau Pathology in the Transgenic Rat Model of Tauopathy,*" Alzheimers & Dementia 5(4)Supp:1-2.

Novak, M. et al. (1993) "*Molecular Characterization of the Minimal Protease Resistant Tau Unit of the Alzheimer's Disease Paired Helical Filament,*" EMBO J 12(1):365-370.

Okamura, N. et al. (2005) "*Quinoline and Benzimidazole Derivatives: Candidate Probes for In Vivo Imaging of Tau Pathology in Alzheimer's Disease,*" J. Neurosci. 25:10857-10862.

Okamura, N. et al. (2014) "*Non-Invasive Assessment of Alzheimer's Disease Neurofibrillary Pathology Using 18F-THK5105 PET,*" Brain 137:1762-1771.

Olafsen, T. et al. (2010) "*Antibody Vectors for Imaging,*" Semin. Nucl. Med. 40:167-181.

Ono, M. et al. (2011) "*Rhodanine and Thiohydantoin Derivatives for Detecting Tau Pathology in Alzheimer's Brains,*" ACS Chem. Neurosci. 2:269-275.

Pardridge, W.M. (2102) "*Drug Transport Across the Blood-Brain Barrier,*" J. Cereb. Blood Flow Metab. 32(11):1959-1972.

Park, S.-Y. et al. (2005) "*The Generation of 17 kDa Neurotoxic Fragment: An Alternative Mechanism by Which Tau Mediates Beta-Amyloid-Induced Neurodegeneration,*" J Neurosci 25(22):5365-5375.

Pedersen, J.T. et al. (2015) "*Tau Immunotherapy for Alzheimer's Disease,*" Trends Mol. Med. Apr. 3, 2015. pii: S1471-4914(15)00058-1; pp. 1-9.

(56) References Cited

OTHER PUBLICATIONS

Perez, M. et al. (2001) "*In Vitro Assembly of Tau Protein: Mapping the Regions Involved in Filament Formation*," Biochemistry 40:5983-5991.

Piszkiewicz, D. et al. (1970) "*Anomalous Cleavage of Aspartyl-Proline Peptide Bonds During Amino Acid Sequence Determinations*," Biochem. Biophys. Res. Commun. 40(5):1173-1178.

Poulsen, K. et al. (1972) "*An Active Derivative of Rabbit Antibody Light Chain Composed of the Constant and the Variable Domains Held Together Only by a Native Disulfide Bond*," Proc. Natl. Acad. Sci. (U.S.A.) 69(9):2495-2499).

Rao, K.S. et al. (2009) "*Targeting Anti-HIV Drugs to the CNS*," Expert Opin. Drug Deliv. 6(8):771-784.

Rea, D.W. et al. (1990) "*Site-specifically radioiodinated antibody for targeting tumors*," Cancer Res. 50(3 Suppl):857s-861s.

Revets, H. et al. (2005) "*Nanobodies as Novel Agents for Cancer Terapy*," Expert Opin Biol Ther. 5(1):111-124.

Richard, J.P. et al. (2003) "*Cell-Penetrating Peptides. A Reevaluation of the Mechanism of Cellular Uptake*," J. Biol. Chem. 278:585-590.

Riechmann, L. et al. (1988) "*Reshaping Human Antibodies for Therapy*," Nature 332:323-327.

Rosenmann, H. et al. (2006) "*Tauopahy-Like Abnormalities and Neurologic Deficits in Mice Immunized with Neuronal Tau Protein*," Arch Neurol 63:1459-1467.

Rudikoff, S. et al. (1982) "*Single Amino Acid Substitution Altering Antigen-Binding Specificity*," Proc. Natl. Acad. Sci. (USA) 79(6):1979-1983.

Sarazin, M. et al. (2012) "*Clinical and Research Diagnostic Criteria for Alzheimer's Disease*," Neuroimaging Clin. N. Amer. 22(1):23-32.

Sato, K. et al. (1993) "*Reshaping a human antibody to inhibit the interleukin 6-dependent tumor cell growth*," Cancer Res. 53:851-856.

Schakowski, F. et al. (2001) "*A novel minimal-size vector (MIDGE) improves transgene expression in colon carcinoma cells and avoids transfection of undesired DNA*," Mol Ther 3, 793-800.

Schenk, D. et al. (1999) "*Immunization With Amyloid-☐ Attenuates Alzheimer-Disease-Like Pathology in the PDAPP Mouse*," Nature 400:173-177.

Schier et al. (1996) "*Isolation of Picomolar Affinity Anti-c-erbB-2 Single-chain Fv by Molecular Evolution of the Complementarity Determining Regions in the Center of the Antibody Binding Site*," J. Mol. Bio. 263:551-567.

Sigurdsson, E.M. (2008) "*Immunotherapy Targeting Pathological Tau Protein in Alzheimer's Disease and Related Tauopathies*," J Alzheimers Dis 15(2):157-168.

Sigurdsson, E.M. (2009) "*Tau-Focused Immunotherapy for Alzheimer's Disease and Related Tauopathies*," Curr Alzheimer Res 6:446-450.

Sigurdsson, E.M. et al. (2000) "*In Vivo Reversal of Amyloid-☐ Lesions in Rat Brain*," J Neuropathology and Neurology 59(1):11-17.

Sigurdsson, E.M. et al. (2008) "*Tau Immunotherapy Prevents Cognitive Decline and Clears Pathological Tau in a Tangle Mouse Model*," Alzheimer's & Dementia: The Journal of the Alzheimer's Association 4(4):T191-T192 (2 pages).

Small, G.W. et al. (1997) "*Diagnosis and Treatment of Alzheimer Disease and Related Disorders. Consensus Statement of the American Association for Geriatric Psychiatry, the Alzheimer's Association, and the American Geriatrics Society*," JAMA 278(16):1363-1371.

Soto, C et al. (1996) "*Inhibition of Alzheimer's Amyloidosis by Peptides that Prevent ☐-Sheet Conformation*," Biochem Biophys Res Com 226(3):672-680.

Steidl, S. et al. (2008) "*In Vitro Affinity Maturation of Human GM-CSF Antibodies by Targeted CDR-Diversification*," Mol. Immunol. 46(1):135-144.

Stork, R. et al. (2008) "*N-Glycosylation as Novel Strategy to Improve Pharmacokinetic Properties of Bispecific Single-Chain Diabodies*," J. Biol. Chem. 283:7804-7812.

Supplemental Search Report EP 10786852.3 PCT/US2010/038184 (dated Oct. 9, 2013) pp. 1-16.

Sykes, K.F. et al. (1999) "*Linear expression elements: a rapid, in vivo, method to screen for gene functions*," Nat. Biotechnol. 12, 355-359.

Taniguchi, T. et al. (2005) "*Effects of Different Anti-Tau Antibodies on Tau Fibrogenesis: RTA-1 and RTA-2 Counteract Tau Aggregation*," FEBS Lett 579(6):1399-1404.

Taylor, L.D. et al. (1992) *A transgenic mouse that expresses a diversity of human sequence heavy and light chain immunoglobulins*, Nucleic Acids Res. 20 (23), 6287-6295.

Taylor, L.D. et al. (1994) "*Human immunoglobulin transgenes undergo rearrangement, somatic mutation and class switching in mice that lack endogenous IgM*," Int. Immunol. 6(4): 579-591.

Tempest, P.R. et al. (1991) "*Reshaping a Human Monoclonal Antibody to Inhibit Human Respiratory Syncytial Virus Infection in vivo*," Nature BioTechnol 9:266-271.

Temsamani, J. et al. (2004) "*The Use of Cell-Penetrating Peptides for Drug Delivery*," Drug Discov. Today 9:1012-1019.

Theunis, C. et al. (2013) "*Efficacy and Safety of a Liposome-Based Vaccine Against Protein Tau, Assessed in Tau.P301L Mice That Model Tauopathy*," PLoS One. 8:e72301.

Troquier et al. (2010) "*Immunotherapy Targeting Tau*," The Biology and Pathology of Tau and its Role in Toauopahies, Biochemical Society, Cambridge, UK, Jan. 7-8, 2010 P016 (Abstract ePub Dec. 2009).

Troquier, L. et al. (2012) "*Targeting Phospho-Ser422 by Active Tau Immunotherapy in the THY-Tau22 Mouse Model: A Suitable Therapeutic Approach*," Curr. Alzheimer Res. 9: 397-405.

Tuaillon et al. (1994), "*Biased utilization of DHQ52 and JH4 gene segments in a human Ig transgenic minilocus is independent of antigenic selection*," J. Immunol. 152: 2912-2920.

Tuma, P.L. et al. (2003) "*Transcytosis: Crossing Cellular Barriers*," Physiol. Rev. 83:871-932.

Van Heeke, G. et al. (1989), "*Expression of Human Asparagine Synthetase in Escherichia coli*," J Biol Chem 264(10):5503-5509.

Verghese, P.B. et al. (2011) "*Apolipoprotein E in Alzheimer's Disease and Other Neurological Disorders*," Lancet Neurol. 10(3):241-252.

Verhoeyen, M. et al. (1988) "*Reshaping Human Antibodies: Grafting an Antilysozyme Activity*," Science 239:1534-1536.

Villemagne, V.L. et al. (2014) "*In Vivo Evaluation of a Novel Tau Imaging Tracer for Alzheimer's Disease*," Eur. J. Nucl. Med. Mol. Imaging 41:816-826.

Wadia, J.S. et al. (2004) "*Transducible TAT-HA Fusogenic Peptide Enhances Escape of TAT-Fusion Proteins After Lipid Raft Macropinocytosis*," Nat. Med. 10:310-315.

Wang, Y.Y. et al. (2009) "*Receptor-Mediated Therapeutic Transport Across the Blood-Brain Barrier*," Immunotherapy 1(6):983-993.

Ward, E.S. et al (1989) "*Binding activities of a repertoire of single immunoglobulin variable domains secreted from Escherichia coli*," Nature 341, 544-546.

Weiner et al. (2013)*The Alzheimer's Disease Neuroimaging Initiative: A Review of Papers Published Since Its Inception*, Alzheimers Dement. 9(5): e11 1-e194.

Wengenack, T.M. et al. (2000) "*Targeting Alzheimer Amyloid Plaques in Vivo*," Nature Biotechnol 18:868-872.

Whitlow, M. et al. (1993) "*An Improved Linker for Single-Chain Fv With Reduced Aggregation and Enhanced Proteolytic Stability*," Protein Eng. 6:989-995.

Wigler, M. et al (1978) "*Biochemical transfer of single-copy eucaryotic genes using total cellular DNA as donor*," Cell 14:725-731.

Winter, G. et al. (1994) "*Making Antibodies by Phage Display Technology*," Annu Rev. Immunol. 12.433-455.

Written Opinion of the International Searching Authority PCT/US2010/038184 (WO 2010/144711) (dated 2011) (5 pages).

Written Opinion of the International Searching Authority PCT/US2015/039205 (WO 2016/007414) (dated 2015) (11 pages).

(56) References Cited

OTHER PUBLICATIONS

Wu, H. et al. (1998) "*Stepwise in vitro affinity maturation of Vitaxin, an alphav beta3-specific humanized mAb*," Proc. Natl. Acad. Sci. (U.S.A.) 95:6037-6042.

Xia, C.F. et al. (2013) "*[(18)F]T807, A Novel Tau Positron Emission Tomography Imaging Agent for Alzheimer's Disease*," Alzheimers Dement. 9:666-676.

Xiong, C.-Y. et al. (2006) "*Development of Tumor Targeting Anti-MUC-1 Multimer: Effects of di-scFv Unpaired Cysteine Location on PEGylation and Tumor Binding*," Protein Engineering Design and Selection 19(8):359-367.

Yanamandra, K. et al. (2013) "*Anti-Tau Antibodies That Block Tau Aggregate Seeding in vitro Markedly Decrease Pathology and Improve Cognition in vivo*," Neuron 80:402-414.

Yelton et al. (1995) "*Affinity maturation of the BR96 anti-carcinoma antibody by codon-based mutagenesis*," J. Immunology 155:1994-2004.

Zhang, W. et al. (2012) "*A Highly Selective and Specific PET Tracer for Imaging of Tau Pathologies*," J. Alzheimers. Dis. 31:601-612 (1 page Abstract Only).

Zilka et al. (2008) "*Chaperone-Like Antibodies Targeting Misfolded Tau Protein: New Vistas in the Immunotherapy of Neurodegenerative Foldopathies*," J Alzheimers Disease 15:169-179.

Zou, Y.-R. et al. (1993) "*Gene targeting in the Ig kappa locus: efficient generation of lambda chain-expressing B cells, independent of gene rearrangements in Ig kappa*," EMBO J. 12(3):811-820.

\* cited by examiner

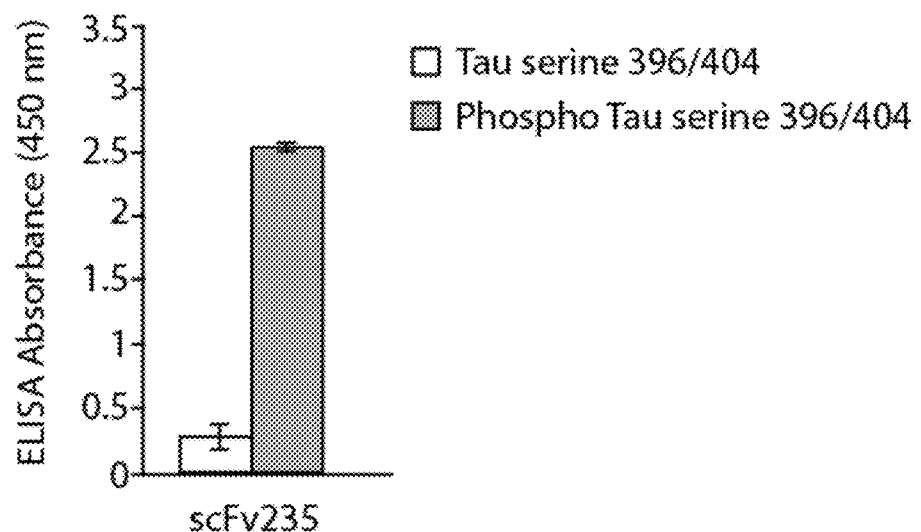
Figure 2A
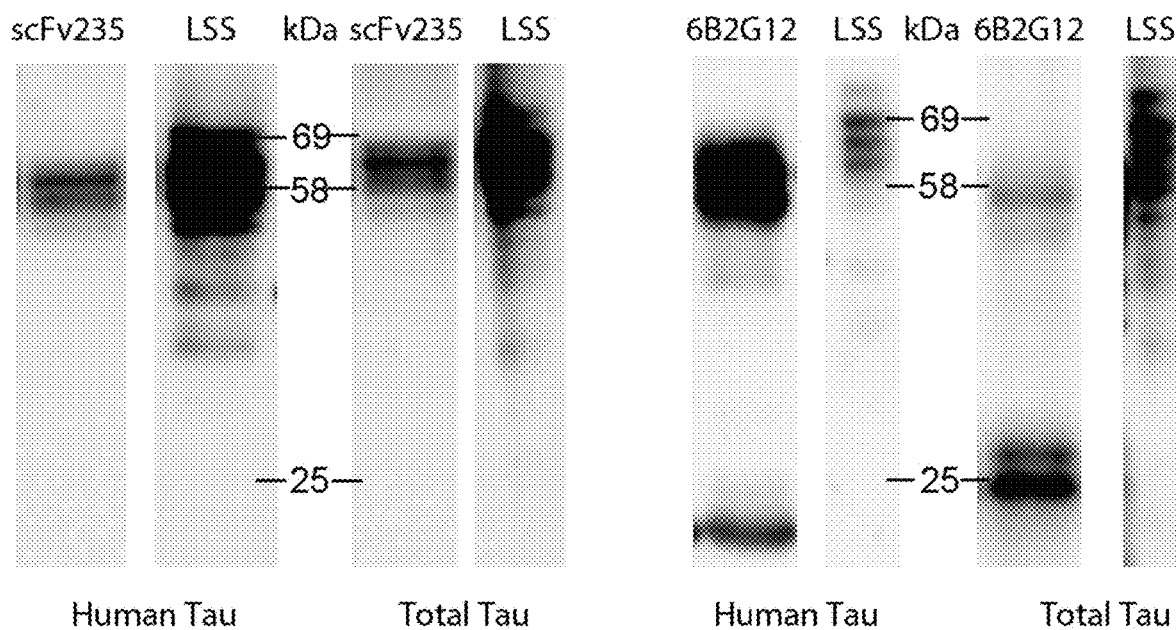
Figure 2B
Figure 2C

Row 1: ScFv235 binds to pathological tau on Alzheimer's disease human brain sections

| Nucleus | scFv235 | PHF1 | Merge |

Row 2: ScFv235 has limited binding to control human brain sections

| Nucleus | scFv235 | PHF1 | Merge |

A47-22 months

| Nucleus | scFv235 | Tau5 | Merge |

B32-23 months

| Nucleus | scFv235 | MC1 | Merge |

B32-23 months

| Nucleus | scFv235 | PHF1 | Merge |

B32-23 months

| Nucleus | scFv235 | EEA1 | Merge |

A47-22 months

| Nucleus | scFv235 | Rab7 | Merge |

B32-23 months

| Nucleus | scFv235 | LC3 | Merge |

A47-22 months

| Nucleus | scFv235 | P62 | Merge |

A47-22 months

| Nucleus | scFv235 | Iba-1 | Merge |

A52-9 months

| Nucleus | 6B2G12 | Tau5 | Merge |

A50-9 months

| Nucleus | 6B2G12 | MC1 | Merge |

A50-9 months

| Nucleus | 6B2G12 | PHF1 | Merge |

A50-9 months

| Nucleus | 6B2G12 | EEA1 | Merge |

A50-9 months

| Nucleus | 6B2G12 | Rab7 | Merge |

A50-9 months

| Nucleus | 6B2G12 | LC3 | Merge |

A52-9 months

| Nucleus | 6B2G12 | P62 | Merge |

P301L #F6

P301L #F6 htau/PS1 #A47 htau/PS1 #A47

Wild-Type #R1

Wild-Type #R1

TAU IMAGING LIGANDS AND THEIR USES IN THE DIAGNOSIS AND TREATMENT OF TAUOPATHY

CROSS-REFERENCE TO RELATED APPLICATIONS

This Application is a continuation of, and claims priority to, U.S. patent application Ser. No. 15/324,141 (which was filed Jan. 5, 2017 and issued on Nov. 20, 2018 as U.S. Pat. No. 10,132,818), which application is a § 371 Application of PCT/US2015/039205 (filed Jul. 6, 2015, now lapsed), which application claims priority to U.S. Provisional Patent Appln. Ser. No. 62/021,897 (filed on Jul. 8, 2014; now lapsed), each of which application is hereby incorporated by reference herein in its entirety.

STATEMENT REGARDING FEDERALLY SPONSORED RESEARCH OR DEVELOPMENT

This invention was made with government support under Grant Nos. NS077239, AG032611 and AG020197 awarded by the National Institutes of Health (NIH). The government has certain rights in the invention.

REFERENCE TO SEQUENCE LISTING

This application includes one or more Sequence Listings pursuant to 37 C.F.R. 1.821 et seq., which are disclosed in computer-readable media (file name: SIG-09-0927-WO-PCT_Sequence_Listing_ST25.txt, created on Jul. 3, 2015, and having a size of 28,918 bytes), which file is herein incorporated by reference in its entirety.

FIELD OF THE INVENTION

The present invention relates to antibody-based probes (including single domain antibody fragment, scFv molecules, antibodies, antibody fragments, diabodies, and the epitope-binding domains thereof) that are capable of immunospecifically and selectively binding to a phospho-serine-containing epitope of Tau, such as, for example, Tau-phospho-serine 396/404 peptide. Such imaging ligands are useful to detect pathological Tau protein conformer if present in a biological sample, especially in conjunction with the diagnosis of Alzheimer's disease or other tauopathy, and thus provide a diagnostic for Alzheimer's disease and other Tau pathologies. The scFv molecules of the present invention have utility as diagnostic markers for, Alzheimer's disease and related tauopathies and as pharmaceutical compositions for the treatment of such conditions.

BACKGROUND OF THE INVENTION

Alzheimer's disease is the most common form of dementia affecting more than 20 million people worldwide.

Diagnosis of the disease, in particular at an early point, is troublesome and difficult and there exists a need for accurate diagnosis of tauopathies such as Alzheimer's disease. Antibody detection of abnormal Tau in cerebrospinal fluid has shown some promise (Blennow et al. "Cerebrospinal Fluid And Plasma Biomarkers In Alzheimer Disease," Nat. Rev. Neurol. 6, 131-144 (2010) and Weiner et al. "The Alzheimer's Disease Neuroimaging Initiative: A Review Of Papers Published Since Its Inception," Alzheimers. Dement. 9, e111-e194 (2013)).

Over the years, antibody detection of phospho-Tau protein in cerebrospinal fluid has shown some utility for diagnosis of Alzheimer's disease (Blennow et al. "Cerebrospinal Fluid And Plasma Biomarkers In Alzheimer Disease," Nat. Rev. Neurol. 6, 131-144 (2010); Lewis, J. et al. "Neurofibrillary Tangles, Amyotrophy And Progressive Motor Disturbance In Mice Expressing Mutant (P301L) Tau Protein," Nat. Genet. 25, 402-405; Weiner, M. W. et al. (2013) "The Alzheimer's Disease Neuroimaging Initiative: A Review Of Papers Published Since Its Inception," Alzheimers. Dement. 9: e111-e194), suggesting that further development in this arena is warranted (see, Congdon, E. E. (2014) "Harnessing The Immune System For Treatment And Detection Of Tau Pathology," J. Alzheimers. Dis. 40: S 113-S121). However, CSF Tau levels in other tauopathies are usually not altered compared to controls (Theunis, C. et al. "Efficacy And Safety Of A Liposome-Based Vaccine Against Protein Tau, Assessed In Tau.P301L Mice That Model Tauopathy," PLoS. One. 8, e72301 (2013); Hales, C. M. et al. (2013) "From Fronto-temporal Lobar Degeneration Pathology To Frontotemporal Lobar Degeneration Biomarkers," Int. Rev. Psychiatry 25:210-220), and imaging dyes may not detect pathological Tau in all tauopathies (Fodero-Tavoletti, M. T. et al. (2014) "Assessing THK523 Selectivity For Tau Deposits In Alzheimer's Disease And Non-Alzheimer's Disease Tauopathies," Alzheimers. Res. Ther. 6:11). Imaging these Tau lesions in concert with amyloid-β (Aβ) is more likely to lead to accurate diagnosis as the regional pattern of Tau aggregates differs between the different tauopathies. Furthermore, all of them except Alzheimer's disease are in part defined by lack of Aβ deposition. In vivo imaging of Aβ plaques using compounds that bind well to β-sheets is already in clinical use (Mason, N. S. et al. (2013) "Positron Emission Tomography Radioligands For In Vivo Imaging Of ABeta Plaques," J. Labelled Comp. Radiopharm. 56:89-95). Several such dye-based Tau-binding ligands have been identified recently in preclinical studies and some of those are being evaluated (Fodero-Tavoletti, M. T. et al. (2014) "Assessing THK523 Selectivity For Tau Deposits In Alzheimer's Disease And Non-Alzheimer's Disease Tauopathies," Alzheimers. Res. Ther. 6:11; Fodero-Tavoletti, M. T. et al. (2011) "18F-THK523: A Novel In Vivo Tau Imaging Ligand For Alzheimer's Disease," Brain 134:1089-1100; Zhang, W. et al. (2012) "A Highly Selective And Specific PET Tracer For Imaging Of Tau Pathologies," J. Alzheimers. Dis. 31:601-612; Chien, D. T. et al. (2013) "Early Clinical PET Imaging Results With The Novel PHF-Tau Radioligand [F-18]-T807," J. Alzheimers. Dis. 34:457-468; Maruyama, M. H. et al. (2013) "Imaging Of Tau Pathology In A Tauopathy Mouse Model And In Alzheimer Patients Compared To Normal Controls," Neuron 79:1094-1108; Okamura, N. et al. (2005) "Quinoline And Benzimidazole Derivatives: Candidate Probes For In Vivo Imaging Of Tau Pathology In Alzheimer's Disease," J. Neurosci. 25:10857-10862; Harada, R., et al. (2013) "Comparison Of The Binding Characteristics Of [18F]THK-523 And Other Amyloid Imaging Tracers To Alzheimer's Disease Pathology," Eur. J. Nucl. Med. Mol. Imaging 40:125-132; Ono, M. et al. (2011) "Rhodanine And Thiohydantoin Derivatives For Detecting Tau Pathology In Alzheimer's Brains," ACS Chem. Neurosci. 2:269-275; Xia, C. F. et al. (2013) "[(18) F]T807, A Novel Tau Positron Emission Tomography Imaging Agent For Alzheimer's Disease," Alzheimers. Dement. 9:666-676; Chien, D. T. (2014) "Early Clinical PET Imaging Results With The Novel PHF-Tau Radioligand [F18]-T808," J. Alzheimers. Dis. 38:171-184; Villemagne, V. L. et al. (2014) "In Vivo Evaluation Of A Novel Tau Imaging Tracer For Alzheimer's Disease," Eur. J. Nucl. Med. Mol. Imaging 41:816-826; Okamura, N. et al. (2014) *"Non-Invasive Assessment Of Alzheimer's Disease Neurofibrillary Pathology Using* 18*F-THK*5105 *PET,"* Brain 137:1762-1771). The hope and promise for Tau based ligands is that they will be better than Aβ ligands to monitor the status and progression of neurodegeneration. Antibody-based probes are likely to provide greater specificity for detecting Tau lesions. In particular, smaller antibody fragments that bind to Tau are attractive as ligands for in vivo imaging to detect Tau lesions in patients with Alzheimer's disease or other tauopathies.

Within the cancer field, therapeutic antibodies have routinely been co-developed as imaging agents, and several such antibodies and Fab molecules are FDA approved for tumor imaging (Kaur, S. et al. *"Recent Trends In Antibody-Based Oncologic Imaging,"* Cancer Lett. 315, 97-111 (2012)).

The present inventors have found antibody-derived imaging ligands that provide excellent specificity for detecting Tau lesions, and in particular smaller single-chain variable antibody fragments (scFv molecules) which are attractive for in vivo imaging of Tau aggregates. It is envisaged that these antibody-derived imaging ligands can be useful in monitoring disease progression of Tau pathology, the efficacy of Tau-targeting therapies, and to identify Aβ negative tauopathies.

SUMMARY OF THE INVENTION

The present invention relates to antibody-based probes (including single domain antibody fragment, scFv molecules, antibodies, antibody fragments, diabodies, and the epitope-binding domains thereof) that are capable of immunospecifically and selectively binding to a phospho-serine-containing epitope of Tau, such as, for example, Tau-phospho-serine 396/404 peptide. Such imaging ligands are useful to detect pathological Tau protein conformer if present in a biological sample, especially in conjunction with the diagnosis of Alzheimer's disease or other tauopathy, and thus provide a diagnostic for Alzheimer's disease and other Tau pathologies. The scFv molecules of the present invention have utility as diagnostic markers for, Alzheimer's disease and related tauopathies and as pharmaceutical compositions for the treatment of such conditions.

In detail, the invention concerns a binding molecule that is capable of immunospecifically binding to a phosphorylated Tau peptide having an amino acid sequence consisting of the amino acid sequence of the Tau 396/404 peptide (SEQ ID NO:7): TDHGAEIVYKS SPVVSGDTS SPRHL, wherein the serine residues at positions 11 and 19 thereof (shown underlined) are phosphorylated, wherein the binding molecule is additionally capable of immunospecifically binding to phosphorylated Tau with greater selectivity than to non-phosphorylated Tau.

The invention also pertains to the embodiment of such a binding molecule wherein the molecule is an antibody or comprises an epitope-binding fragment thereof. The invention further pertains to the embodiment of any of such binding molecules wherein the binding molecule comprises such an epitope-binding fragment, and more particularly wherein the molecule is an isolated CDR, a single domain antibody fragment, an scFv or a diabody. The invention particularly pertains to the embodiment of any of such binding molecules wherein upon peripheral injection into a recipient, the binding molecule substantially co-localizes with a Tau aggregate.

The invention also pertains to the embodiment of such binding molecules wherein the epitope-binding fragment comprises any one, any two, any three, any four, any five or all six of:
(a) a Light Chain CDR1 having the amino acid sequence of SEQ ID NO:12;
(b) a Light Chain CDR2 having the amino acid sequence of SEQ ID NO:13;
(c) a Light Chain CDR3 having the amino acid sequence of SEQ ID NO:14;
(d) a Heavy Chain CDR1 having the amino acid sequence of SEQ ID NO:15;
(e) a Heavy Chain CDR2 having the amino acid sequence of SEQ ID NO:16; and/or
(f) a Heavy Chain CDR3 having the amino acid sequence of SEQ ID NO:17.

The invention also pertains to the embodiment of such binding molecules wherein the binding molecule is scFv235 (SEQ ID NO:18).

The invention also pertains to the embodiment of any of such binding molecules which is detectably labeled, and especially, any of such binding molecules wherein the detectable label is a fluorescent label, a chemoluminescent label, a paramagnetic label, a radioisotopic label or an enzyme label The invention also pertains to the use of any of the above-described binding molecules for detecting or measuring the presence or amount of the phosphorylated Tau protein in the brain, or in a biological fluid (e.g., cerebrospinal fluid, blood, serum, plasma, etc.) of a recipient subject. The invention particularly pertains to such a use, the use wherein the detection or measurement comprises in vivo or ex vivo imaging of the binding molecule bound to the phosphorylated Tau protein, and more particularly, wherein the detection or measurement is for diagnosing Alzheimer's disease or another tauopathy of a subject.

The invention also pertains to an in vivo medicament for the treatment of Alzheimer's disease or another tauopathy of a subject, wherein the medicament comprises the binding molecule of any of claims 1-8 in an amount effective to treat the Alzheimer's disease or other tauopathy, and one or more carriers, diluents and/or stabilizers.

The invention also pertains to the use of such an in vivo medicament for the treatment of Alzheimer's disease or another tauopathy of the subject.

The invention particularly pertains to the above-recited uses, wherein the subject is a human.

The invention also pertains to a kit for detecting or measuring the presence or amount of the phosphorylated Tau protein in the brain of a subject, or for diagnosing Alzheimer's disease or another tauopathy in a subject, wherein the kit comprises any of the above-recited binding molecules.

The invention further pertains to any of the above-recited uses, or to any of the above-recited medicament, or to any of the above-recited kits, wherein the tauopathy is selected from the group comprising frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

BRIEF DESCRIPTION OF THE DRAWINGS

FIGS. 2A-2E: scFv235 binds selectively to phospho-Tau epitope and to Tau protein in Alzheimer's brain homogenate.

FIG. 2A shows that scFv235 selectively binds to phospho-Tau-serine 396/404 (P-Ser396/404) epitope in ELISA compared to its non-phospho equivalent epitope (Ser396/404).

FIG. 2B shows that scFv235 specifically binds to Tau of Alzheimer's disease brain homogenate. Incubation of a brain homogenate from an individual with Alzheimer's disease with scFv235 results in the immunoprecipitation of Tau bands in the range of 50-70 kDa. Western blots with CP27 (human Tau) and polyclonal total Tau antibody (Dako) showed similar results with no other bands detected. For comparison, a low speed supernatant (LSS) of the brain homogenate is shown in an adjacent lane from the same blot with several additional Tau positive bands.

FIG. 2C: Incubation of a brain homogenate from an individual with Alzheimer's disease with 6B2G12 results in the immunoprecipitation of Tau bands in the range of 50-70 kDa as well as degradation fragments in the range of 20-30 kDa. Western blots with CP27 (human Tau) and polyclonal total Tau antibody (Dako) showed greater detection of intact Tau with CP27 and smaller Tau fragments with Dako Tau. For comparison, a low speed supernatant (LSS) of the brain homogenate is shown in an adjacent lane from the same blot with several additional Tau positive bands.

FIG. 2D: Shows the results of differential staining for four human brain sections. Row 1: brain section from Alzheimer's disease individual AD-1; Row 2: brain section from Alzheimer's disease individual AD-2; Row 3: brain section from Pick's disease individual; Row 4: brain section from healthy control individual. Column A: section stained with Hoechst to show nuclei; Column B: section stained with scFv235; Column C: section stained with PHF1; Column D: sections merged to show localization (see arrows). Staining of human brain sections with scFv235 revealed extensive neuronal staining that showed partial localization with PHF1 staining. Very limited staining was observed in control human tissue. Scale bar=20 μm.

FIG. 2E: Shows that scFv 235 binds to pathological Tau on Alzheimer's disease human brain sections, but exhibits limited binding to control human brain sections.

FIG. 3A: Intracarotid Imaging. Images recorded prior to injection (Column A) and at specified intervals (Column B, Column C and Column D) post-injection. Row 1: images of P301L (12 months old) transgenic mouse, injected with scFv235 tagged with near infrared dye (680 nm) and imaged before injection (Column A), and at 38 minutes (Column B), 82 minutes (Column C) and 220 minutes (Column D) post-injection. Signal is detected throughout the body with highest intensity in the brain that slowly decreases over time. Brain signal peaked at 35-38 min (1714% above pre-injection baseline signal), and remained strong at 82 and 330 minutes post-injection (1675% and 1468%, respectively). Row 2: images from an scFv235-injected htau/PS1 (22 months) transgenic mouse, recorded before injection, and at 37 minutes (Column B), 65 minutes (Column C) and 176 minutes (Column D) post-injection. Again, the most intense signal was detected in the brain and it gradually decreased over time. Brain signal peaked at 37 minutes (1443% above pre-injection baseline signal), and remained strong at 65 and 176 minutes post-injection (1144% and 1093%, respectively). Row 3: images of scFv235-injected wt (9 months) mouse, before injection and at 37 minutes (Column B), 75 minutes (Column C) and 265 minutes (Column D) post-injection. Very limited brain signal was detected post-injection with no signal in periphery. Row 4: images of 6B2G12-injected P301L (10 months) transgenic mouse, recorded before injection and at 37 minutes (Column B), 170 minutes (Column C) and 291 minutes (Column D) post-injection. Signal is strongest in the brain and gradually decreases over time, with similar signal obtained from 20-95 minutes post-injection (600-632% above baseline value), with a modest reduction at the depicted 170 and 291 minutes (497% and 431%, respectively). Row 5: images of 6B2G12-injected wt mouse (8 months), recorded before injection and at 37 minutes (Column B), 90 minutes (Column C) and 225 minutes (Column D) post-injection. Virtually no signal is detected. The scale bar shows maximum pixel intensity, whereas the region of interest (ROI) is total radiant efficiency (TRE) of summed pixel intensity.

FIG. 3B: Quantitative analysis of IVIS (in vivo Imaging System) brain signal over time after intracarotid injection: Highest signal was detected in P301L mice injected with scFv235. The older mice (11 and 12 months) had total radiant efficiency (TRE) peak at 2.23E+11 and 2.64E+11 respectively, whereas the younger mice (3 and 8 months) had lower peak signals (1.88E+11 and 1.86E+11 respectively). The same P301L model (7-10 months) had strong but lesser brain signal after 6B2G12 injection, ranging from 2.20E+11 to 1.16E+11. Similar signal intensity was observed in an old scFv235-injected htau/PS1 mouse (22 months; peak at 1.40E+11) but limited in a 7 months old htau/PS1 mouse, which was confirmed to lack Tau pathology. Wt mice (12-13 months) and one htau mouse (13 months) had low signal at all time points and had no Tau pathology. Injection of the fluorescent-tag alone in an old htau/PS1 mouse (23 months) and a P301L mouse (7 months) gave a higher brain signal than in wt mice, injected with scFv235 or antibody, but it was substantially less than in any of the tauopathy mice injected with scFv235 or 6B2G12. These two dye injected mice were confirmed to have extensive Tau pathology (see FIG. 4B).

FIG. 3C: Intravenous Imaging. Images recorded prior to injection (Column A) and at specified intervals (Column B, Column C and Column D) post-injection. Row 1: images of P301L (13 months old) transgenic mouse, injected with scFv235 tagged with near infrared dye (680 nm) and imaged before injection (Column A), and at 18 minutes (Column B), 210 minutes (Column C) and 11520 minutes (day 8) (Column D) post-injection. Peak brain signal was detected at 18 min (1754% above pre-injection baseline), with lesser signal at 210 min (18% reduction from peak signal), that had substantially subsided at 8 days (43% reduction). Row 2: images from an Tg-SwDI Aβ plaque mouse (12 months) recorded before injection, and at 25 minutes (Column B), 60 minutes (Column C) and 11520 minutes (day 8) (Column D)

post-injection. Very limited brain signal was detected post-injection with no signal in periphery. Row 3: images of 6B2G12-injected P301L (7 months) transgenic mouse, before injection and at 25 minutes (Column B), 120 minutes (Column C) and 11520 minutes (day 8) (Column D) post-injection. Brain signal was strong at 25 minutes (1211% above pre-injection baseline), peaked at 35 minutes (1445%), with lesser signal at 120 minutes (11% reduction from peak signal) and was much weaker by 8 and 12 days (67% and 70% reduction, respectively). Row 4: images of 6B2G12 injected Tg-SwDI mouse (12 months), recorded before injection and at 25 minutes (Column B), 180 minutes (Column C) and 11520 minutes (day 8) (Column D) post-injection. Very limited brain signal was detected post-injection with no signal in periphery.

Figure 3A:
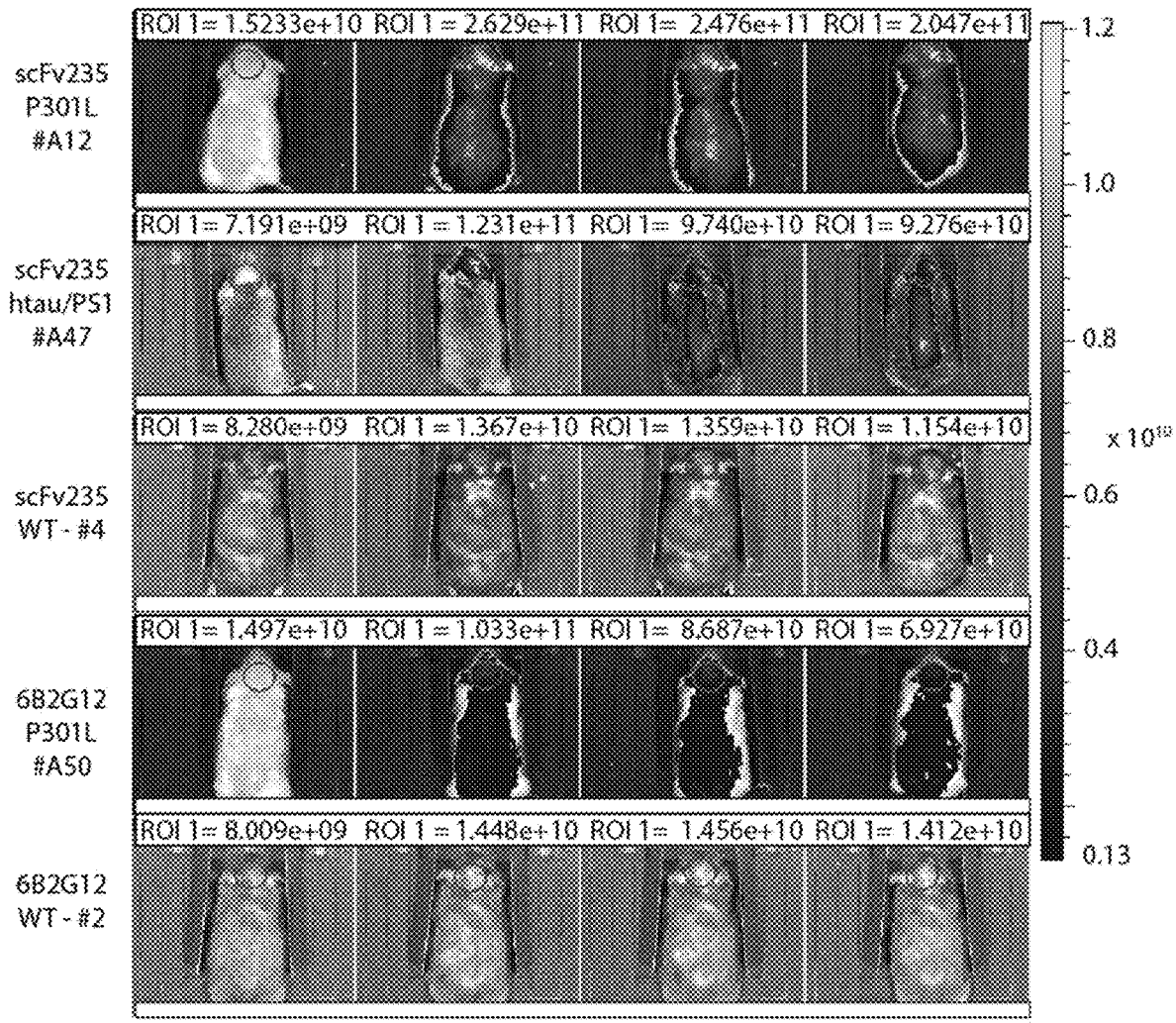
FIGS. 3A-3D: In vivo imaging of Tau inclusions in P301L, htau/PS1, htau, Tg-SwDI and wild-type mice after intracarotid or intravenously injected fluorescently labeled scFv235 or 6B2G12. Representative images from various groups are shown in different panels.
Figure 3B:
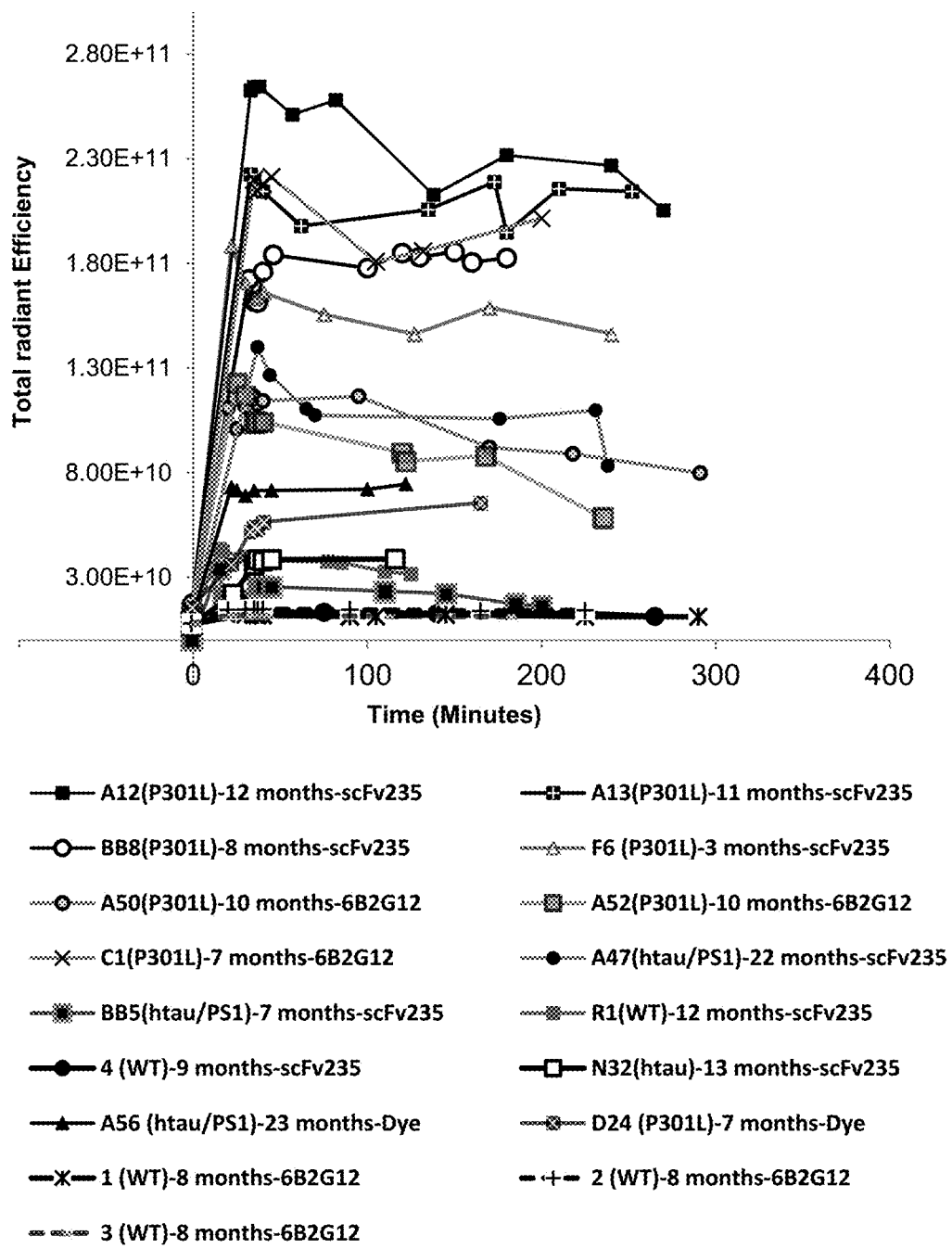
Figure 3C:
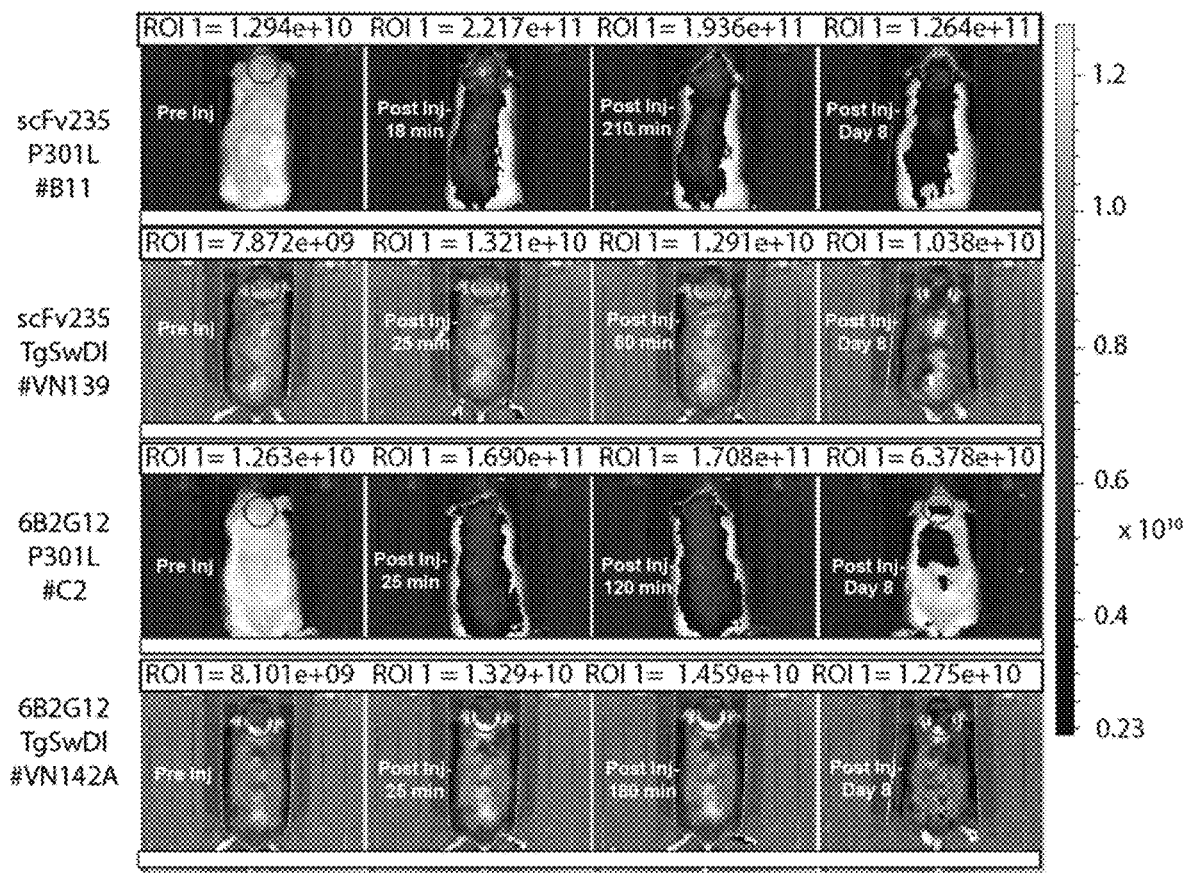
Figure 3D:
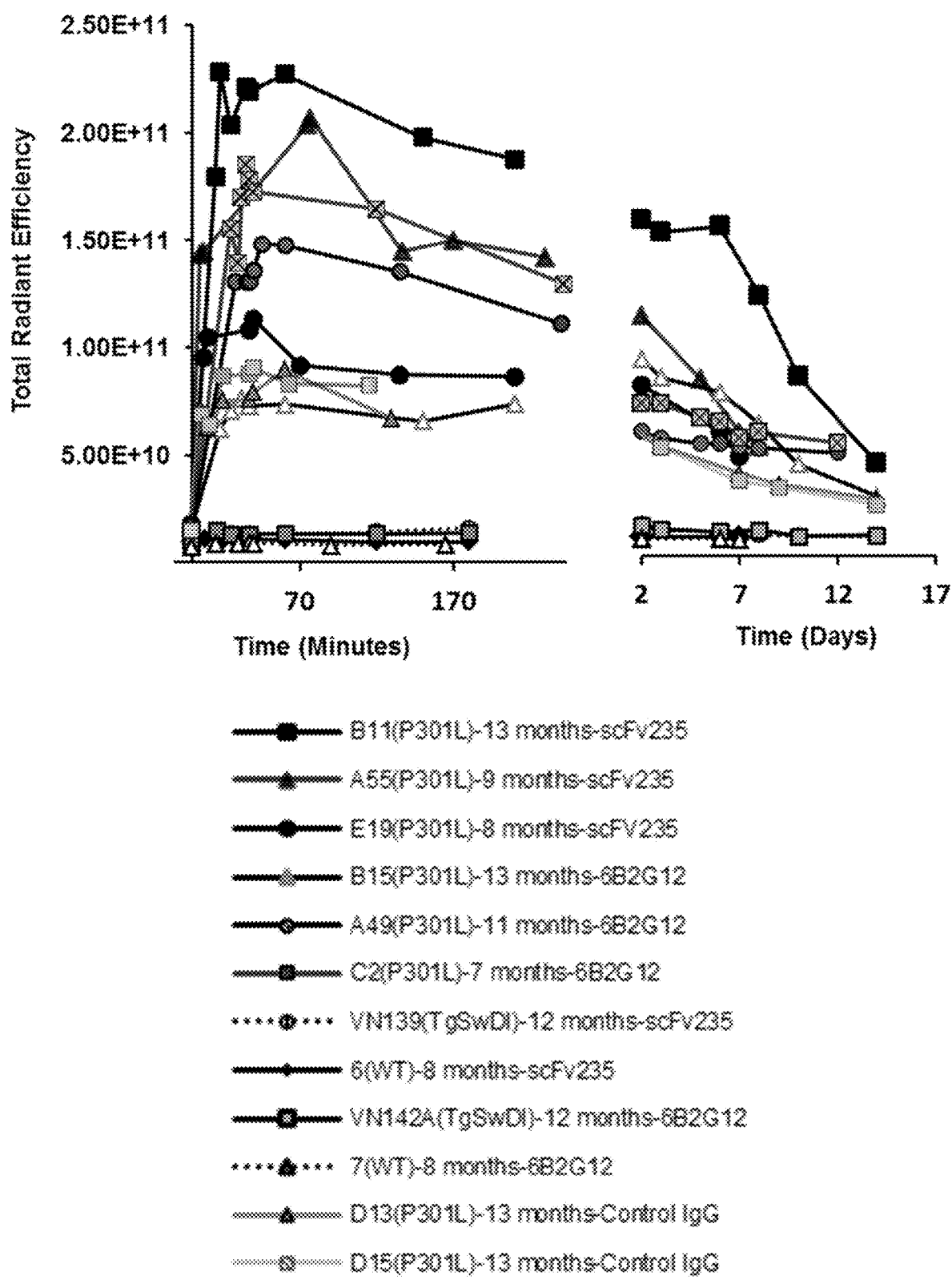

FIG. 3D: Quantitative analysis of IVIS brain signal over time after intravenous injection: scFv235 and 6B2G12 were injected into P301L mice. These mice could be imaged at earlier time points post-injection than the intracarotid injected mice as the latter route requires longer postoperative care to prevent bleeding. Peak signal was generally obtained within the first hour post-injection, depending on the animal, at similar intervals for all probes. Overall signal was substantially higher for scFv235 and 6B2G12 compared to control IgG, even though the IgG injected mice had the most robust Tau pathology (see Table 6). One 6B2G12 injected mouse (B15) had comparable IVIS signal to the IgG injected mice but more modest Tau pathology. The signal gradually subsided over 14 days at different rates for individual P301L mice. Very limited signal was detected at all time points in injected Tg-SwDI or wt mice with either probe.

FIGS. 4A-4D: Co-localization of injected scFv235 and 6B2G12 with intraneuronal Tau protein, markers of endosomes-autophagosomes-lysosomes and microglia. Brains were removed 3-4 hours following intracarotid injection and IVIS imaging, fixed, sectioned coronally and stained for: (1) Tau with Tau5 (total Tau), MC1 (conformational), PHF1 (phospho-Tau), and (2) early endosomes (EEA1); (3) late endosomes/lysosomes (Rab 7); and (4) autophagosomes (LC3, P62). Sections were also stained with microglia (Iba-1).

Figure 4A:
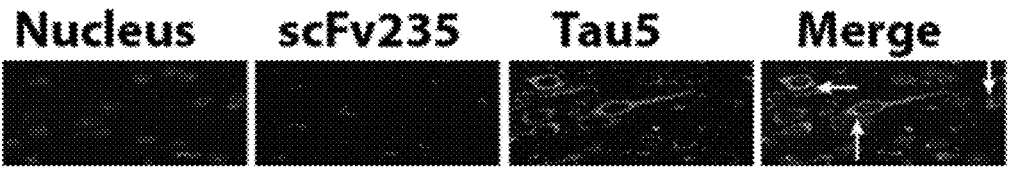
Figure 4A:
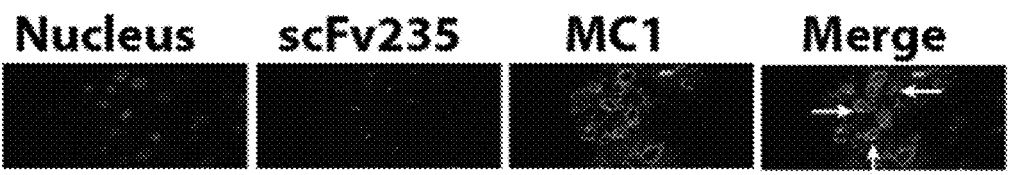
Figure 4A:
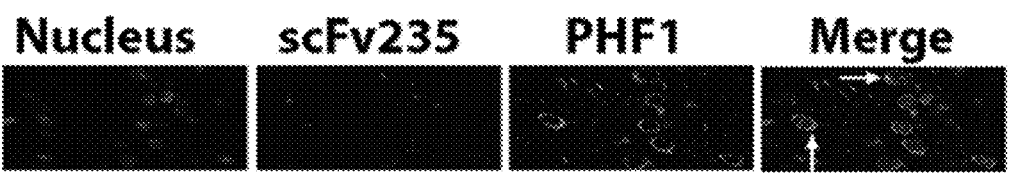
Figure 4A:
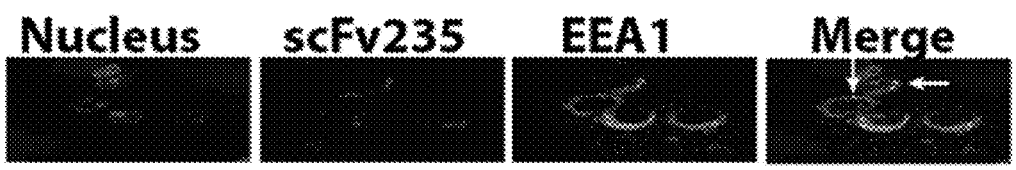
Figure 4A:
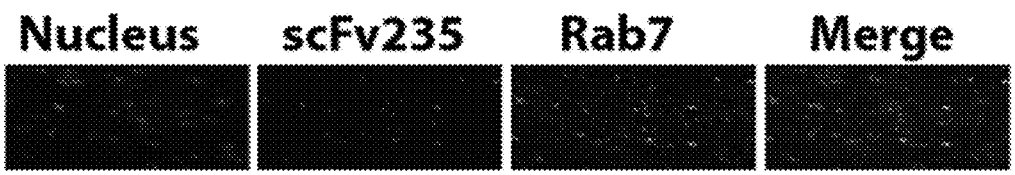
Figure 4A:
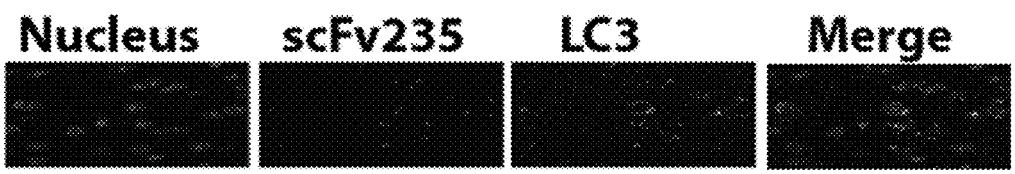
Figure 4A:
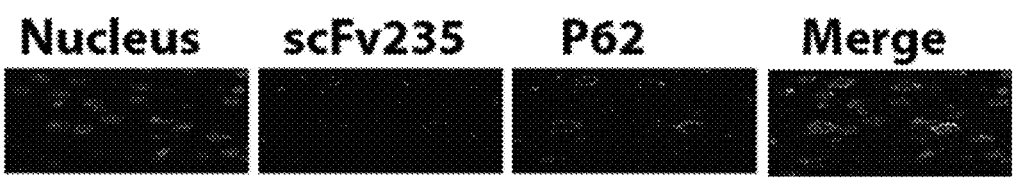

FIG. 4A: scFv235-injected P301L mice (Rows 1-2, 4 and 7: mouse "A12;" Row 3: mouse "BBB;" Rows 5-6: mouse "A13") were imaged to identify nuclei (Column A), imaged with scFV235 (Column B), imaged to show PHF1 (Column C), and a merged image was created (Column D). Images showed partial co-localization with MC1, Tau5, and PHF1, and complete co-localization with Rab7, EEA1, LC3 and P62.

Figure 4B:
Figure 4B:
Figure 4B:
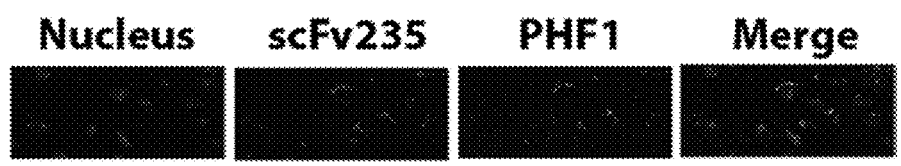
Figure 4B:
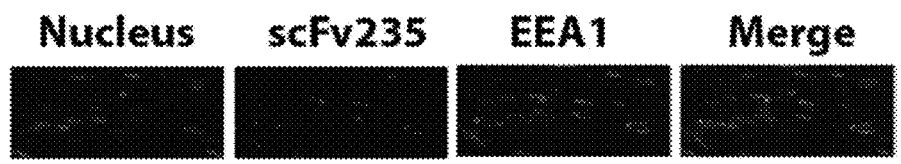
Figure 4B:
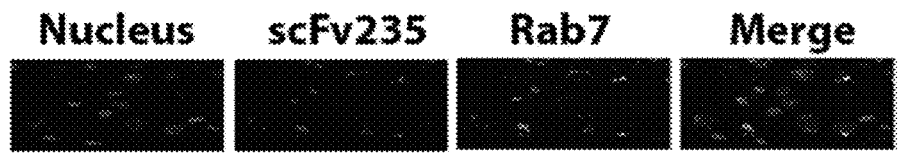
Figure 4B:
Figure 4B:
Figure 4B:
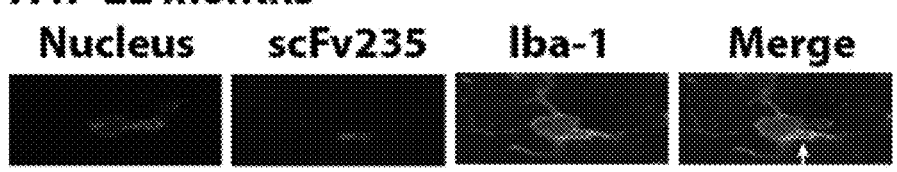

FIG. 4B: scFv235-injected htau/PS1 mice (Rows 1, 5, 7-8: mouse "A47;" Rows 2-4 and 6: mouse "B32") were imaged to identify nuclei (Column A), imaged with scFV235 (Column B), imaged to show PHF1 (Column C), and a merged image was created (Column D). Images showed partial co-localization of the injected scFv235 with MC1, Tau5, and Iba-1 (not shown) and complete co-localization with PHF1, Rab7, EEA1, LC3 and P62 antibodies.

Figure 4C:
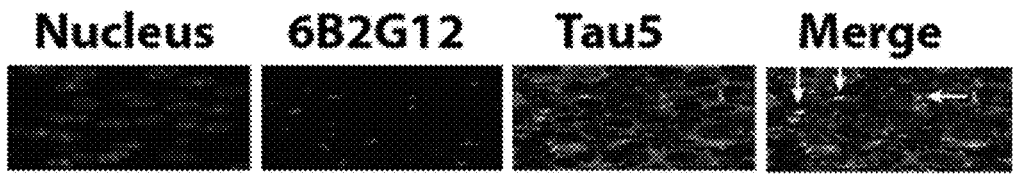
Figure 4C:
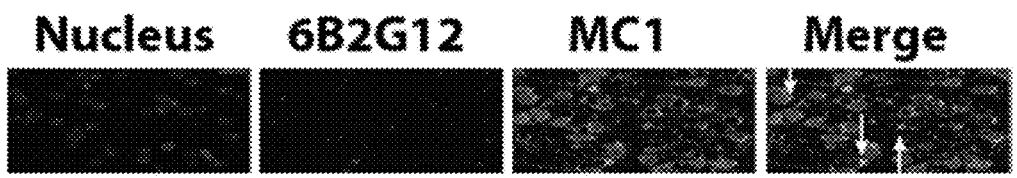
Figure 4C:
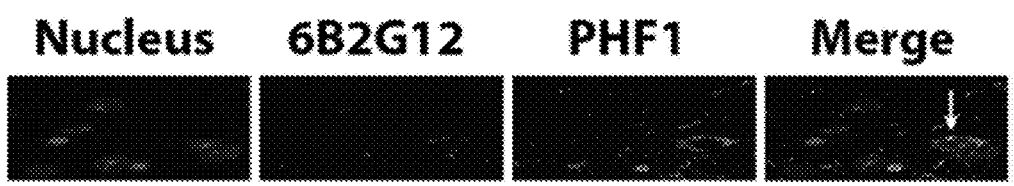
Figure 4C:
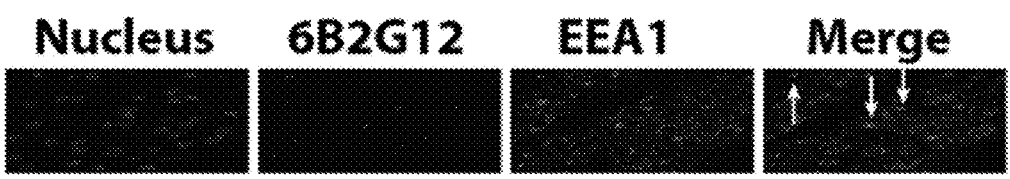
Figure 4C:
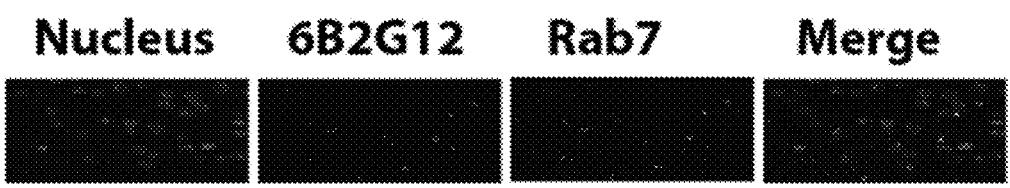
Figure 4C:
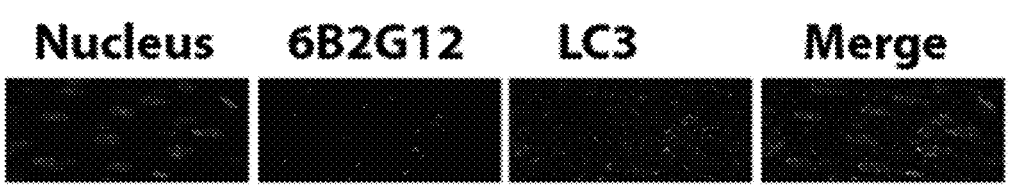
Figure 4C:
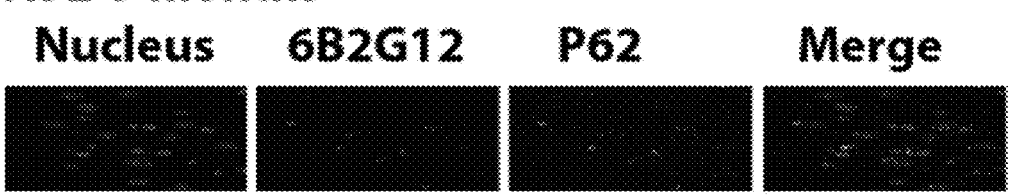

FIG. 4C: 6B2G12-injected P301L mice (Rows 1 and 7: mouse "A52;" Rows 2-6: mouse "A50") were imaged to identify nuclei (Column A), imaged with scFV235 (Column B), imaged to show PHF1 (Column C), and a merged image was created (Column D).

Images showed partial co-localization with MC1, Tau5, PHF1, Rab7, EEA1, LC3 and 62.

Figure 4D:
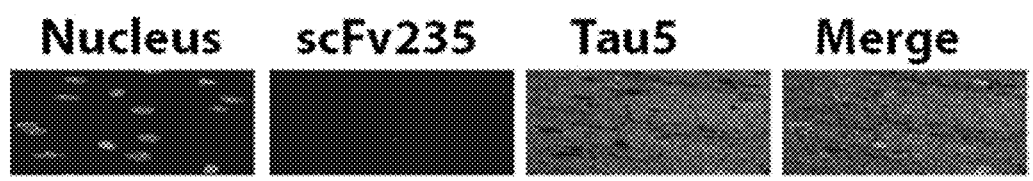
Figure 4D:
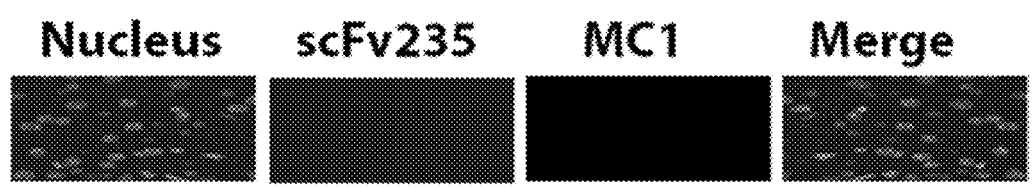
Figure 4D:
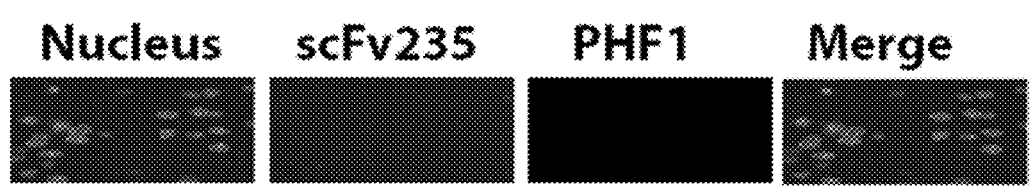
Figure 4D:
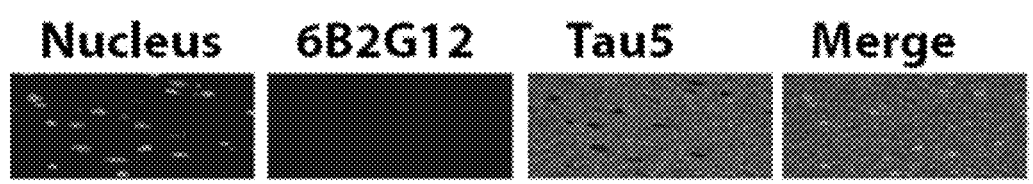
Figure 4D:
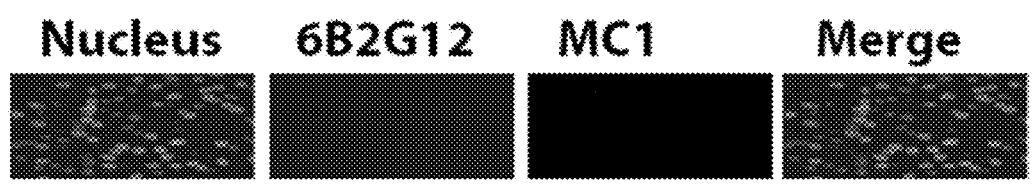
Figure 4D:
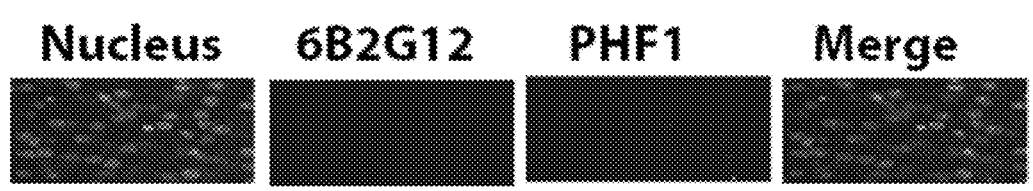

FIG. 4D: Wt mice injected with scFv235 (Rows 1-3) or 6B2G12 (Rows 4-6) were imaged to identify nuclei (Column A), imaged with scFV235 (Column B), imaged to show PHF1 (Column C), and a merged image was created (Column D). Images showed limited signal from the antibody fragment and limited staining with the antibody markers except for normal Tau detected with Tau5. Nuclei are stained blue with Hoechst nuclear stain. Scale bar=10 μm. Arrows point at some of the neurons with partial co-localization. No arrows were used when there was complete co-localization.

Figure 5:
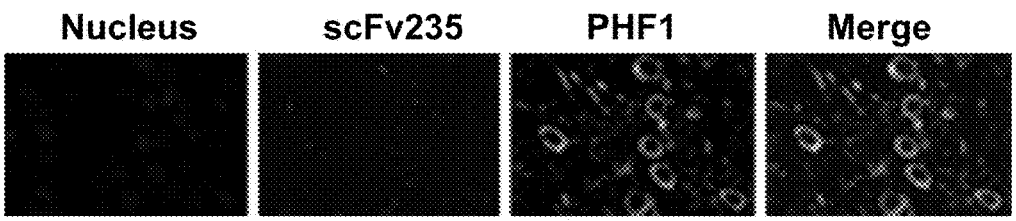
Figure 5:
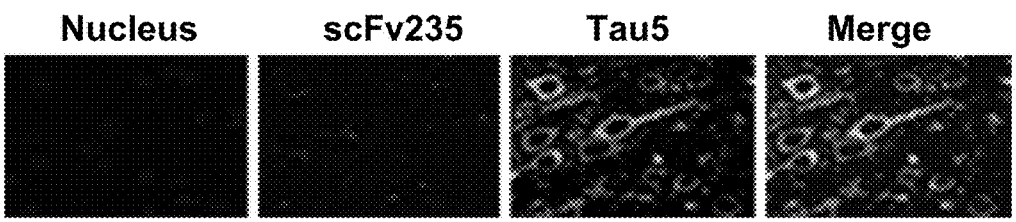
Figure 5:
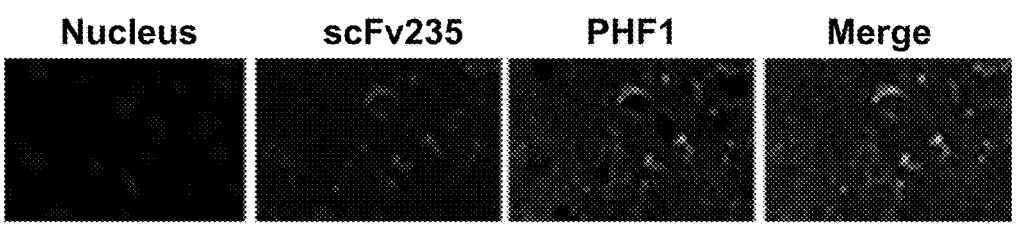
Figure 5:
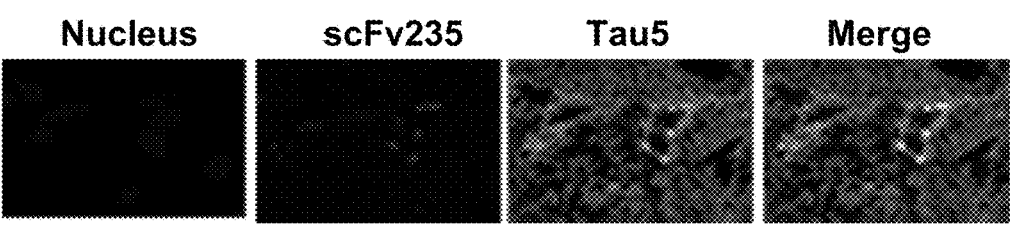
Figure 5:
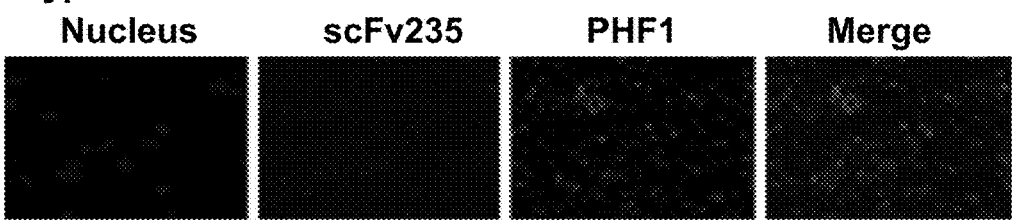
Figure 5:
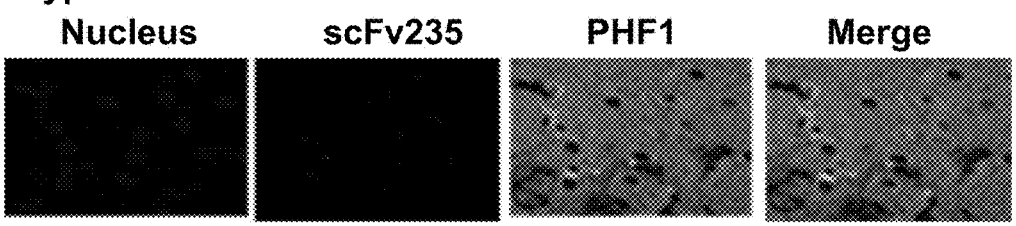
Figure 6A:
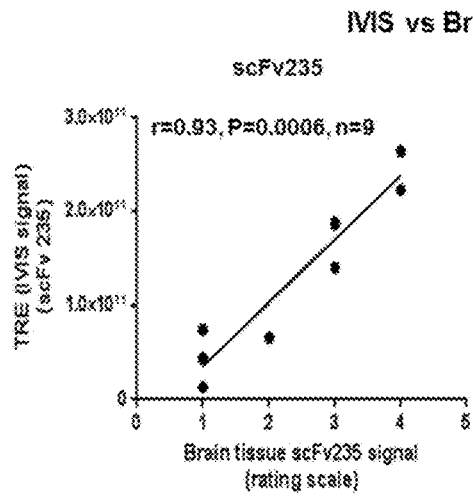
Figure 6B:
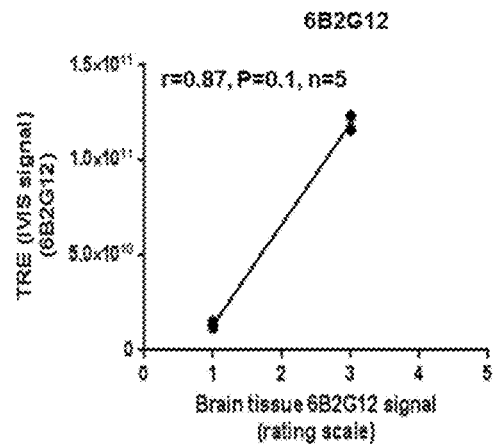
Figure 6C:
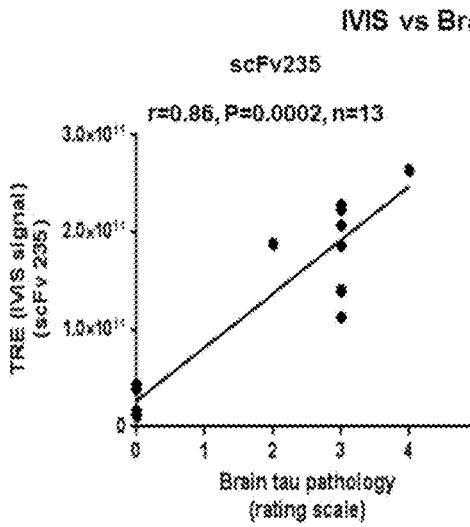
Figure 6D:
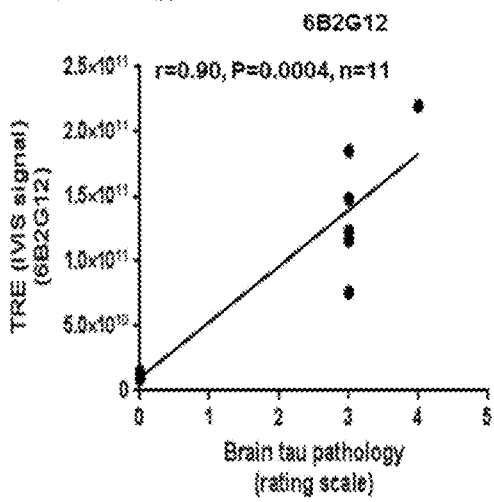
Figure 6E:
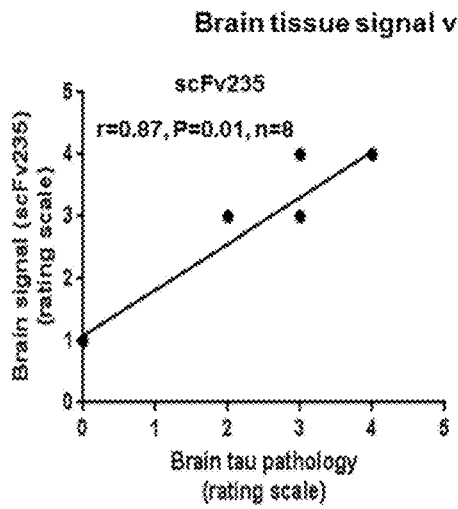
Figure 6F:
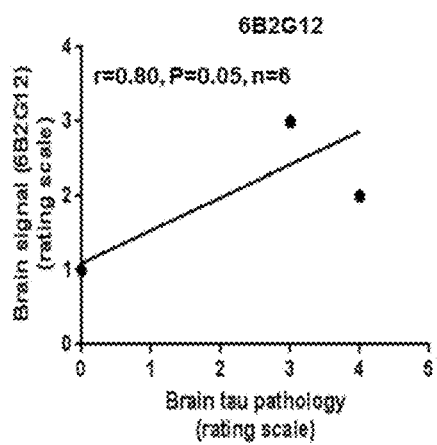

FIG. 5 shows that scFv235 co-localized with pathological Tau within brain neurons following intracarotid injection in P301L (F6) and htau/PS1 (A47) tangle mice, but did not have detectable uptake in control wild-type mice (R1).

FIGS. 6A-6F show the excellent correlation that was observed of IVIS signal with (FIGS. 6A-6B) brain tissue probe signal (scFv235: r=0.98, 6B2G12: r=0.87) and with (FIGS. 6C-6D) Tau pathology (scFv235: r=0.94, 6B2G12: r=0.75). The brain tissue probe signal correlated as well nicely with (FIGS. 6E-6F) brain Tau pathology (scFv235: r=0.99, 6B2G12: r=0.97).

DETAILED DESCRIPTION OF THE INVENTION

The present invention relates to antibody-based probes (including single domain antibody fragment, scFv molecules, antibodies, antibody fragments, diabodies, and the epitope-binding domains thereof) that are capable of immunospecifically and selectively binding to a phospho-serine-containing epitope of Tau, such as, for example, Tau-phospho-serine 396/404 peptide. Such imaging ligands are useful to detect pathological Tau protein conformer if present in a biological sample, especially in conjunction with the diagnosis of Alzheimer's disease or other tauopathy, and thus provide a diagnostic for Alzheimer's disease and other Tau pathologies. The scFv molecules of the present invention have utility as diagnostic markers for, Alzheimer's disease and related tauopathies and as pharmaceutical compositions for the treatment of such conditions.

The antibody-based probes of the present invention provide greater specificity than β-sheet dyes for detecting Tau lesions in patients with AD or other tauopathies. In particular, smaller antibody fragments that bind to Tau are attractive as ligands for in vivo imaging. Their smaller size compared to antibodies leads to better access to Tau aggregates. Another advantage is their relatively rapid clearance from the circulation compared to unmodified antibodies that have longer half-lives. Within the cancer field, therapeutic antibodies have routinely been co-developed as imaging agents, and several such antibodies and Fab's or smaller diabodies and scFv molecules with better pharmacokinetic properties approved or proposed as tumor imaging agents (see, Kaur, S. et al. (2012) "*Recent Trends In Antibody-Based Oncologic Imaging,*" Cancer Lett. 315:97-111; Olafsen, T. et al. (2010) "*Antibody Vectors For Imaging,*" Semin. Nucl. Med. 40:167-181).

I. Tau and the Preferred Immunogenic Tau Peptides of the Present Invention

As used herein, the term "Tau" is synonym with the Tau protein and refers to any of the Tau protein isoforms (identified in for example UniProt as P10636, 1-9). The amino acid numbering of Tau is given with respect to SEQ ID NO: 1 as shown below, Met being amino acid 1. "P-Tau" refers to a Tau protein that has been phosphorylated at one or more serine or threonine residues. For example P-Ser 396/404 refers to a polypeptide of Tau that comprises the amino acid sequence of SEQ ID NO:1 wherein serine residues 396 and 404 are phosphorylated:

SEQ ID NO: 1:
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIINK

KLDLSNVQSK CGSKDNIKHV PGGGSVQIVY KPVDLSKVTS

KCGSLGNIHH KPGGGQVEVK SEKLDFKDRV QSKIGSLDNI

THVPGGGNKK IETHKLTFRE NAKAKTDHGA EIVYKSPVVS

GDTSPRHLSN VSSTGSIDMV DSPQLATLAD EVSASLAKQG L

Tau is a soluble microtubule-associated protein that is dynamically phosphorylated and dephosphorylated by a host of kinase enzymes during the cell cycle. Tau's ability to stabilize microtubules is dependent on the extent of its phosphorylation. In its dephosphorylated form, the protein is able to interact with tubulin to stabilize microtubules and promote tubulin assembly into microtubules (which form the cytoskeleton of the cell and are the major constituents of the mitotic spindles that pull apart eukaryotic chromosomes in mitosis). In its phosphorylated form, Tau is able to dissociate from microtubules, thereby permitting mitosis to occur. The phosphorylation of Tau acts thus as a direct microtubule association-dissociation switch within the neuron (Pedersen, J. T. et al. (2015) "*Tau Immunotherapy For Alzheimer's Disease*," Trends Mol. Med. 2015 Apr. 3. pii: S1471-4914 (15)00058-1; pages 1-9, hereby incorporated by reference herein in its entirety).

Hyperphosphorylation of Tau can result in the formation of insoluble self-assembling "tangles," referred to herein as "Tau aggregates," of paired helical filaments and straight filaments. Such Tau aggregates may be intracellular (e.g., intraneuronal), but may also form outside of the cells. The presence of Tau aggregates impairs Tau's ability to stabilize microtubules and thus leads to microtubule disassembly, dendritic spinal collapse, and the degeneration of axons. Normal Tau contains, on average two phosphorylated sites; the hyperphosphorylated Tau filaments average seven to eight phosphorylated sites. Hyperphosphorylated Tau is the main constituent of the intracellular neurofibrillary tangles that are a main hallmark of Alzheimer's Disease.

II. The Preferred Antibodies and Epitope-Binding Fragments of the Present Invention As used herein, the term "antibody" refers to an intact immunoglobulin as well as a molecule having an epitope-binding fragment thereof. Naturally occurring antibodies typically comprise a tetramer which is usually composed of at least two heavy (H) chains and at least two light (L) chains. Each heavy chain is comprised of a heavy chain variable region (abbreviated herein as VH) and a heavy chain constant region, usually comprised of three domains (CH1, CH2 and CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable region (abbreviated herein as VL) and a light chain constant region (CL). Light chains include kappa chains and lambda chains. The heavy and light chain variable region is typically responsible for antigen recognition, while the heavy and light chain constant region may mediate the binding of the immunoglobulin to host tissues or factors, including various cells of the immune system (e.g., effector cells) and the first component (Clq) of the classical complement system. The VH and VL regions can be further subdivided into regions of hypervariability, termed "complementarity determining regions," that are interspersed with regions of more conserved sequence, termed "framework regions" (FR). Each VH and VL is composed of three CDR Domains and four FR Domains arranged from amino-terminus to carboxy-terminus in the following order: FR1-CDR1-FR2-CDR2-FR3-CDR3-FR4. The variable regions of the heavy and light chains contain a binding domain that interacts with an antigen. Of particular relevance are antibodies and their epitope-binding fragments that have been "isolated" so as to exist in a physical milieu distinct from that in which it may occur in nature or that have been modified so as to differ from a naturally occurring antibody in amino acid sequence.

Fragments of antibodies (including Fab and (Fab)$_2$ fragments) that exhibit epitope-binding ability can be obtained, for example, by protease cleavage of intact antibodies. More preferably, such fragments will be single domain antibody fragments, scFv molecules, and the epitope-binding domains of antibodies, etc., that are formed using recombinant techniques. For example, although the two domains of the Fv fragment, VL and VH, are encoded by separate genes, such gene sequences or their encoding cDNA can be joined, using recombinant methods, by a flexible linker (typically of about 10, 12, 15 or more amino acid residues) that enables them to be made as a single protein chain in which the VL and VH regions associate to form monovalent epitope-binding molecules (known as single-chain Fv (scFv) molecules; see e.g., Bird et al., (1988) Science 242:423-426; and Huston et al. (1988) Proc. Natl. Acad. Sci. (U.S.A.) 85:5879-5883). Alternatively, by employing a flexible linker that is too short (e.g., less than about 9 residues) to enable the VL and VH regions of a single polypeptide chain to associate together, one can form a bispecific antibody, diabody, or similar molecule (in which two such polypeptide chains associate together to form a bivalent epitope-binding molecule) (see for instance PNAS USA 90(14), 6444-8 (1993) for a description of diabodies). Single domain antibody fragments possess only one variable domains (e.g., VL or VH). Examples of the epitope-binding fragments encompassed within the present invention include (i) Fab' or Fab fragments, a monovalent fragment consisting of the VL, VN, CL and CH1 domains, or a monovalent antibody as described in WO2007059782; (ii) F(ab')$_2$ fragments, bivalent fragments comprising two Fab fragments linked by a disulfide bridge at the hinge region; (iii) Fd fragments consisting essentially of the VH and CH1 domains; (iv) Fv fragments consisting essentially of a VL and VH domain, (v) dAb fragments (Ward et al., Nature 341, 544-546 (1989)), which consist essentially of a VH domain and also called domain antibodies (Holt et al; Trends Biotechnol. 2003 November; 2i(11): 484-90); (vi) camelid or nanobodies (Revets et al; Expert Opin Biol Ther. 2005 January; 5_(1): 1 11-24) and (vii) isolated complementarity determining regions (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3, IgG4, IgD, IgA, IgE, or IgM) that is encoded by heavy chain constant region genes. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of an anti-Tau antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1, κ.

Such antibody fragments are obtained using conventional techniques known to those of skill in the art. For example, F(ab')2 fragments may be generated by treating antibody with pepsin. The resulting F(ab')2 fragment may be treated to reduce disulfide bridges to produce Fab' fragments. Fab fragments may be obtained by treating an IgG antibody with papain; Fab' fragments may be obtained with pepsin digestion of IgG antibody. An F(ab') fragment may also be produced by binding Fab' described below via a thioether bond or a disulfide bond. A Fab' fragment is an antibody fragment obtained by cutting a disulfide bond of the hinge region of the F(ab')2. A Fab' fragment may be obtained by treating an F(ab')2 fragment with a reduc-ing agent, such as dithiothreitol. Antibody fragment may also be generated by expression of nucleic acids encoding such fragments in recombinant cells (see for instance Evans et al., J. Immunol. Meth. 184, 123-38 (1995)). For example, a chimeric gene encoding a portion of an F(ab')2 fragment could include DNA sequences encoding the CH1 domain and hinge region of the H chain, followed by a translational stop codon to yield such a truncated antibody fragment molecule. Suitable fragments capable of binding to a desired epitope may be readily screened for utility in the same manner as an intact antibody.

In one embodiment, such antibody fragments are a monovalent antibody, preferably a monovalent antibody as described in PCT Publication WO 2007/059782 (which is incorporated herein by reference in its entirety) having a deletion of the hinge region. Such an antibody may be constructed by a method comprising: i) providing a nucleic acid construct encoding the light chain of said monovalent antibody, said construct comprising a nucleotide sequence encoding the VL region of a selected antigen specific anti alpha-synuclein antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulfide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the antibody is a monovalent antibody, which comprises:
(i) a variable region of an antibody of the invention as described herein or an antigen binding part of the said region, and
(ii) a CH region of an immunoglobulin or a fragment thereof comprising the CH2 and CH3 regions, wherein the CH region or fragment thereof has been modified such that the region corresponding to the hinge region and, if the immunoglobulin is not an IgG4 subtype, other regions of the CH region, such as the CH3 region, do not comprise any amino acid residues, which are capable of forming disulfide bonds with an identical CH region or other covalent or stable non-covalent inter-heavy chain bonds with an identical CH region in the presence of polyclonal human IgG.

In a further embodiment, the heavy chain of the monovalent antibody has been modified such that the entire hinge has been deleted.

In another further embodiment, the sequence of said monovalent antibody has been modified so that it does not comprise any acceptor sites for N-linked glycosylation.

As used herein, an antibody or an epitope-binding fragment thereof is said to "immunospecifically" bind a region of another molecule (i.e., an epitope) if it reacts or associates more frequently, more rapidly, with greater duration and/or with greater affinity or avidity with that epitope relative to alternative epitopes. It is also understood by reading this definition that, for example, an antibody or an epitope-binding fragment thereof that specifically binds to a first target may or may not specifically or preferentially bind to a second target.

As used herein, the term "binding" in the context of the binding of an antibody or binding fragment thereof to a predetermined antigen typically refers to binding with an affinity corresponding to a $K_D$ of about $10^{-7}$ M or less, such as about $10^{-8}$ M or less, such as about $10^{-9}$ M or less when determined by, for instance, surface plasmon resonance (SPR) technology in a BIAcore 3000 instrument (preferably using the antibody as the ligand and the antigen as the analyte), and which binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$k_d$" (sec$^{-1}$ or 1/s), as used herein, refers to the dissociation rate constant of a particular antibody-antigen interaction. Said value is also referred to as the $k_{off}$ value. The term "$k_a$" (M$^{-1}$×sec$^{-1}$ or 1/M), as used herein, refers to the association rate constant of a particular antibody-antigen interaction. The term "$K_D$" (M), as used herein, refers to the dissociation equilibrium constant of a particular antibody-antigen interaction. The term "$K_A$" (M$^{-1}$ or 1/M), as used herein, refers to the association equilibrium constant of a particular antibody-antigen interaction and is obtained by dividing the $k_a$ by the $k_d$.

As used herein, an antibody or an epitope-binding fragment thereof is said to "selectively" bind to a phosphorylated peptide epitope if it immunospecifically binds to such epitope with higher affinity than it binds (if it binds at all) to a non-phosphorylated peptide epitope having the same amino acid sequence. Most preferably, such higher affinity will be at least 10-fold higher, at least 30-fold higher, at least 100-fold higher, at least 300-fold higher, at least 1,000-fold higher, at least 3,000-fold higher, or at least 10,000-fold higher. scFv235 "selectively" binds to the phosphorylated P-Ser396/404 peptide relative to the non-phosphorylated peptide (exhibiting a "selectivity" of about 4,000-fold). The extent of "selectivity" of an antibody, or of an epitope-binding fragment thereof, for phosphorylated Tau is determined by comparing, via ELISA or Biacore, the affinity with which an scFv of such antibody immunospecifically binds to a non-phosphorylated target Tau peptide and to a phosphorylated variant thereof.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former, but not the latter, is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, the term "epitope-binding fragment of an antibody" means a fragment of an antibody capable of immunospecifically binding to an epitope. An epitope-binding fragment may contain 1, 2, 3, 4, 5 or all 6 of the CDR Domains of such antibody and, although capable of immunospecifically binding to such epitope, may exhibit an immunospecificity, affinity or selectivity toward such epitope that differs from that of such antibody. Preferably, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino-terminus and a carboxyl terminus (e.g., a diabody, an Fab fragment, an Fab$_2$ fragment, etc.).

The antibodies of the present invention, and their Tau epitope-binding fragments will preferably be "humanized," particularly if employed for therapeutic purposes. The term "humanized" refer to a chimeric molecule, generally prepared using recombinant techniques, having an antigen binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild type (e.g., fully human) or they may be modified to contain one or more amino acid substitutions not found in the human antibody whose sequence has served as the basis for humanization. Humanization lessens or eliminates the likelihood that a constant region of the molecule will act as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Speci-*

*ficity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody. The ability to humanize an antigen is well known (see, e.g., U.S. Pat. Nos. 5,225,539; 5,530,101; 5,585,089; 5,859,205; 6,407,213; 6,881,557).

In one embodiment, the antibody of the invention is a human antibody. Suitable human antibodies may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice.".

The HuMAb mouse contains a human immunoglobulin gene minilocus that encodes unrearranged human heavy variable and constant (μ and Y) and light variable and constant (K) chain immunoglobulin sequences, together with targeted mutations that inactivate the endogenous μ and K chain loci (Lonberg, N. et al., Nature 368, 856-859 (1994)). Accordingly, such mice exhibit reduced expression of mouse IgM or IgK and in response to immunization, the introduced human heavy and light chain transgenes, undergo class switching and somatic mutation to generate high affinity human IgG, κ monoclonal antibodies (Lonberg, N. et al. (1994), supra; reviewed in Lonberg, N., Handbook of Experimental Pharmacology 113, 49-101 (1994), Lonberg, N. and Huszar, D., Intern. Rev. Immunol. Vol. 13 65-93 (1995) and Harding, F. and Lonberg, N., Ann. N. Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424).

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756, 687, 5,750,172 and 5,741,957.

In some antibodies only part of a CDR, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable Regions Of Immunoglobulins*," J. Mol. Biol. 196:901-917), by molecular modeling and/or empirically, or as described in Gonzales, N. R. et al. (2004) "*SDR Grafting Of A Murine Antibody Using Multiple Human Germline Templates To Minimize Its Immunogenicity*," Mol. Immunol. 41:863-872. In such humanized antibodies at positions in which one or more donor CDR residues is absent or in which an entire donor CR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to ROR1, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

The invention thus contemplates the use of guided or random mutagenesis to identify improved CDRs.

In the context of the present invention, conservative substitutions may be defined by substitutions within the classes of amino acids reflected in one or more of the following three tables:

Amino Acid Residue Classes For Conservative Substitutions:

TABLE 2

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |

TABLE 2-continued

| | |
|---|---|
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues:

TABLE 4

| | |
|---|---|
| Alcohol Group-Containing Residues | S and T |
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |

TABLE 1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | -1 | -2 | -2 | 0 | -1 | -1 | 0 | -2 | -1 | -1 | -1 | -1 | -2 | -1 | +1 | 0 | -3 | -2 | 0 |
| R | -1 | +5 | 0 | -2 | -3 | +1 | 0 | -2 | 0 | -3 | -2 | +2 | -1 | -3 | -2 | -1 | -1 | -3 | -2 | -3 |
| N | -2 | 0 | +6 | +1 | -3 | 0 | 0 | 0 | +1 | -3 | -3 | 0 | -2 | -3 | -2 | +1 | 0 | -4 | -2 | -3 |
| D | -2 | -2 | +1 | +6 | -3 | 0 | +2 | -1 | -1 | -3 | -4 | -1 | -3 | -3 | -1 | 0 | -1 | -4 | -3 | -3 |
| C | 0 | -3 | -3 | -3 | +9 | -3 | -4 | -3 | -3 | -1 | -1 | -3 | -1 | -2 | -3 | -1 | -1 | -2 | -2 | -1 |
| Q | -1 | +1 | 0 | 0 | -3 | +5 | +2 | -2 | 0 | -3 | -2 | +1 | 0 | -3 | -1 | 0 | -1 | -2 | -1 | -2 |
| E | -1 | 0 | 0 | +2 | -4 | +2 | +5 | -2 | 0 | -3 | -3 | +1 | -2 | -3 | -1 | 0 | -1 | -3 | -2 | -2 |
| G | 0 | -2 | 0 | -1 | -3 | -2 | -2 | +6 | -2 | -4 | -4 | -2 | -3 | -3 | -2 | 0 | -2 | -2 | -3 | -3 |
| H | -2 | 0 | +1 | -1 | -3 | 0 | 0 | -2 | +8 | -3 | -3 | -1 | -2 | -1 | -2 | -1 | -2 | -2 | +2 | -3 |
| I | -1 | -3 | -3 | -3 | -1 | -3 | -3 | -4 | -3 | +4 | +2 | -3 | +1 | 0 | -3 | -2 | -1 | -3 | -1 | +3 |
| L | -1 | -2 | -3 | -4 | -1 | -2 | -3 | -4 | -3 | +2 | +4 | -2 | +2 | 0 | -3 | -2 | -1 | -2 | -1 | +1 |
| K | -1 | +2 | 0 | -1 | -3 | +1 | +1 | -2 | -1 | -3 | -2 | +5 | -1 | -3 | -1 | 0 | -1 | -3 | -2 | -2 |
| M | -1 | -1 | -2 | -3 | -1 | 0 | -2 | -3 | -2 | +1 | +2 | -1 | +5 | 0 | -2 | -1 | -1 | -1 | -1 | +1 |
| F | -2 | -3 | -3 | -3 | -2 | -3 | -3 | -3 | -1 | 0 | 0 | -3 | 0 | +6 | -4 | -2 | -2 | +1 | +3 | -1 |
| P | -1 | -2 | -2 | -1 | -3 | -1 | -1 | -2 | -2 | -3 | -3 | -1 | -2 | -4 | +7 | -1 | -1 | -4 | -3 | -2 |
| S | +1 | -1 | +1 | 0 | -1 | 0 | 0 | 0 | -1 | -2 | -2 | 0 | -1 | -2 | -1 | +4 | +1 | -3 | -2 | -2 |
| T | 0 | -1 | 0 | -1 | -1 | -1 | -1 | -2 | -2 | -1 | -1 | -1 | -1 | -2 | -1 | +1 | +5 | -2 | -2 | 0 |
| W | -3 | -3 | -4 | -4 | -2 | -2 | -3 | -2 | -2 | -3 | -2 | -3 | -1 | +1 | -4 | -3 | -2 | +11 | +2 | -3 |
| Y | -2 | -2 | -2 | -3 | -2 | -1 | -2 | -3 | +2 | -1 | -1 | -2 | -1 | +3 | -3 | -2 | -2 | +2 | +7 | -1 |
| V | 0 | -3 | -3 | -3 | -1 | -2 | -2 | -3 | -3 | +3 | +1 | -2 | +1 | -1 | -2 | -2 | 0 | -3 | -1 | +4 |

TABLE 4-continued

| | |
|---|---|
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody,*" MBio. 2(1) pii: e00345-10. doi: 10.1128/mBio.00345-10; Kuan, C. T. et al. (2010) "*Affinity Matured Anti-Glycoprotein NMB Recombinant Immunotoxins Targeting Malignant Gliomas And Melanomas,*" Int. J. Cancer 10.1002/ijc.25645; Hackel, B. J. et al. (2010) "*Stability And CDR Composition Biases Enrich Binder Functionality Landscapes,*" J. Mol. Biol. 401(1):84-96; Montgomery, D. L. et al. (2009) "*Affinity Maturation And Characterization Of A Human Monoclonal Antibody Against HIV-1 gp41,*" MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth,*" Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions,*" J. Mol. Biol. 388(3):541-558; Bostrom, J. et al. (2009) "*Improving Antibody Binding Affinity And Specificity For Therapeutic Development,*" Methods Mol. Biol. 525:353-376; Steidl, S. et al. (2008) "*In Vitro Affinity Maturation Of Human GM-CSF Antibodies By Targeted CDR-Diversification,*" Mol. Immunol. 46(1):135-144; and Barderas, R. et al. (2008) "*Affinity Maturation Of Antibodies Assisted By In Silico Modeling,*" Proc. Natl. Acad. Sci. (USA) 105(26):9029-9034.

The term "transgenic non-human animal" refers to a non-human animal having a genome comprising one or more human heavy and/or light chain transgenes or tran-schromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-Tau antibody when immunized with Tau antigen and/or cells expressing Tau. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO 02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

The use of the antibodies of the present invention, or their epitope-binding fragments, as Tau imaging probes has great potential due to their specificity. Because of the general impermeability of the blood-brain barrier, smaller single-chain variable antibody fragments (scFv molecules) have been found to be preferred as in vivo imaging ligands to detect Tau lesions. scFv molecules are formed as a fusion protein of the variable regions of the heavy (H) and light chain (L) domains of an antibody, connected to one another via a short linker peptide of from about 10 to about 25 amino acid residues. The linker is usually rich in glycine for flexibility (e.g., GGGGSGGGGSGGGGS (SEQ ID NO:2) (Fisher, A. et al. (2009)"*Efficient Isolation Of Soluble Intracellular Single-Chain Antibodies Using The Twin-Arginine Translocation Machinery,*" J. Mol. Biol. 385(1):299-311; Bird, R. E. et al. (1988) "*Single-Chain Antigen-Binding Proteins,*" Science 242:423-426; Huston, J. S. et al. (1988) "*Protein Engineering Of Antibody Binding Sites: Recovery Of Specific Activity In An Anti-Digoxin Single-Chain Fv Analogue Produced In Escherichia coli,*" Proc. Natl. Acad. Sci. (U.S.A.) 85:5879-5883), as well as serine or threonine for solubility, and can either connect the N-terminus of the Heavy Chain Variable Domain with the C-terminus of the Light Chain Variable Domain VL, or vice versa (Huang, L. et al. (2013) "*Single-Chain Fragment Variable Passive Immunotherapies For Neurodegenerative Diseases,*" Int. J. Mol. Sci. 14(9):19109-19127; Ahmad, Z. A. et al. (2012) "*scFv Antibody: Principles And Clinical Application,*" Clin. Dev. Immunol. 2012:980250; Huhalov, A. et al. (2004) "*Engineered Single Chain Antibody Fragments For Radioimmunotherapy,*" Q. J. Nucl. Med. Mol. Imaging 48(4):279-288). An example of such a linker is GSTSGS-GKPGSGEGSTKG (SEQ ID NO:3) (Whitlow, M. et al. (1993) "*An Improved Linker For Single-Chain Fv With Reduced Aggregation And Enhanced Proteolytic Stability,*" Protein Eng. 6:989-995). A particularly preferred linker for the present invention has the amino acid sequence (SEQ ID NO:4): SSGGGGSGGGGGSSRSS.

In order to facilitate purification and/or recovery, the scFv may include a poly histidine ("His-Tag") (e.g., (SEQ ID NO:5) HHHHHH). The imidazole side chains of the histidine residues of the His-Tag can engage in reversible coordinative bonds to certain transition metal ions, such as $Co^{2+}$, $Zn^{2+}$ and especially $Ni^{+2}$. Thus, when His-tagged scFv molecules are applied to a matrix containing such metal ions, they specifically bind to the matrix, while most untagged proteins do not. The scFv may additionally or alternatively include an "HA-Tag" such as (SEQ ID NO:6) GAYPYDVPDYAS. Human influenza hemagglutinin (HA) is a surface glycoprotein required for the infectivity of the human virus. The HA-tag is derived from the human influenza hemagglutinin (HA) surface glycoprotein, and permits detection of the scFv using an anti-HA-Tag antibody (Millipore).

scFv molecules may be expressed directly or as a fusion protein that is linked to an N-terminal leader peptide that is cleaved in order to yield the scFv (see, e.g., Huston, J. S. et al. (1988) "*Protein Engineering Of Antibody Binding Sites: Recovery Of Specific Activity In An Anti-Digoxin Single-Chain Fv Analogue Produced In Escherichia coli,*" Proc. Natl. Acad. Sci. (U.S.A.) 85:5879-5883). For example, the scFv may be fused to the modified trp LE leader peptide (MLE)), and cleaved away by acid cleavage of the Asp-Pro peptide bond (Piszkiewicz, D. et al. (1970) "*Anomalous Cleavage Of Aspartyl-Proline Peptide Bonds During Amino Acid Sequence Determinations,*" Biochem. Biophys. Res. Commun. 40(5):1173-1178; Fraser, K. J. et al. (1972) "*Specific Cleavage Between Variable And Constant Domains Of Rabbit Antibody Light Chains By Dilute Acid Hydrolysis,*" Biochemistry 11(26):4974-4977; Poulsen, K. et al. (1972) "*An Active Derivative Of Rabbit Antibody Light Chain Composed Of The Constant And The Variable Domains Held Together Only By A Native Disulfide Bond,*" Proc. Natl. Acad. Sci. (U.S.A.) 69(9):2495-2499).

In a further embodiment, an scFv can be linked to another scFv (which may be the same or different) in order to form a bivalent molecule. This can be done by producing a single peptide chain with two VH and two VL regions, yielding tandem scFv molecules (Xiong, C.-Y. et al. (2006) "*Development Of Tumor Targeting Anti-MUC-1 Multimer: Effects Of di-scFv Unpaired Cysteine Location On PEGylation And Tumor Binding,*" Protein Engineering Design and Selection 19(8):359-367; Kufer, P. et al. (2004) "*A Revival Of Bispecific Antibodies,*" Trends in Biotechnology 22(5):238-244). Alternatively, by forming an scFv whose Heavy Chain Variable Domain is separated from its Light Chain Variable Domain by a linker that is too short to permit such domains to complex with one another and form an epitope-binding site, one can force two scFv molecules to dimerize as a diabody (Hollinger, P. et al. (1993) "*Diabodies": Small Bivalent And Bispecific Antibody Fragments,*" Proc. Natl. Acad. Sci. (U.S.A.) 90(14):6444-6448). Diabodies have been shown to have dissociation constants up to 40-fold lower than corresponding scFv molecules, meaning that they have a much higher affinity to their target. Consequently, diabody drugs could be dosed much lower than other therapeutic antibodies and are capable of highly specific targeting of tumors in vivo (Adams, G. P. et al. (1998) "*Prolonged in vivo Tumour Retention Of A Human Diabody Targeting The Extracellular Domain Of Human HER2/neu,*" Brit. J. Cancer 77(9):1405-1412). Still shorter linkers (one or two amino acids) lead to the formation of trimers, so-called triabodies or tribodies. Tetrabodies have also been produced. They exhibit an even higher affinity to their targets than diabodies (Le Gall, F. et al. (1999) "*Di-, Tri-And Tetrameric Single Chain Fv Antibody Fragments Against Human CD19: Effect Of Valency On Cell Binding,*" FEBS Letters 453(1):164-168). All of these formats can be composed from variable scFv molecules so as to form dimers, trimers, etc. having specificity for two or more different epitopes (i.e., bi-specific diabodies, etc.) (Dincq, S. et al. (2001) "*Expression And Purification Of Monospecific And Bispecific Recombinant Antibody Fragments Derived From Antibodies That Block The CD80/CD86-CD28 Costimulatory Pathway,*" Protein Express. Purificat. 22(1):11-24).

As discussed below, suitable scFv molecules were isolated from libraries of scFv molecules that had been generated from Tau antibody hybridomas using a combinatorial phage display technology (see, for example, U.S. Pat. Nos. 5,565,332; 5,580,717; 5,733,743; 6,265,150; and Winter, G. et al. (1994) "*Making Antibodies By Phage Display Technology,*" Annu. Rev. Immunol. 12.433-455). Numerous phospho-Tau-selective scFv molecules were identified and their reactivity toward Tau confirmed by immunoprecipitation, staining of human and mouse tauopathy tissue as well as affinity assays. Peripheral injection of these scFv molecules resulted in a strong in vivo brain signal in transgenic tauopathy mice but not in wild-type or amyloid-β plaque mice. The imaging signal was shown to correlate very well with co-localization of the probe with intraneuronal Tau aggregates. Both were associated with markers of endosomes, autophagosomes and lysosomes, suggesting their interaction in these degradation pathways. Such specific antibody-derived imaging probes have great potential as diagnostic markers for AD and related tauopathies.

Such efforts led to the isolation of preferred anti-phospho-Tau 396,404 antibody 6B2G12, which was elicited against a peptide having the amino acid sequence (SEQ ID NO:7): TDHGAEIVYKS SPVVSGDTS SPRHL, which corresponds to amino acid residues 386-408 of Tau protein (SEQ ID NO:1), The underlined serine residues at positions 11 and 19 of SEQ ID NO:7 (corresponding to positions 396 and 404 of Tau (SEQ ID NO:1)) are phosphorylated. The employed immunogen contained this peptide, modified to contain an N-terminal cysteine residue that was conjugated to keyhole limpet hemocyanin (KLH).

The Light Chain Variable Domain of antibody 6B2G12 has the amino acid sequence (SEQ ID NO:8) (CDRs are underlined):

```
ELDVQMTQTP LTLSVTIGQP ASISCKSSQS LLYSNGKTYL

NWLLQRPGQS PKRLIYLVSK LDSGVPDRFT GSGSGTDFTL

KISRVEAEDL GVYYCVQGTH SPLTFGAGTK LELK
```

The Heavy Chain Variable Domain of antibody 6B2G12 has the amino acid sequence (SEQ ID NO:9) (CDRs are underlined):

```
LEVQLQQSGP ELVKPGASVK ISCKTSEYTF TEYTKHWVKQ

SHGKSLEWIG SINPNNGDTY YNQKFTDKAT LTVDKSSTTA

SMELRSLTFE DSAVYYCAMG DSAWFAYWGQ GTLVTVS
```

This antibody was used to form the scFv molecule: scFv235.

The Light Chain Variable Domain of scFv235 has the amino acid sequence (SEQ ID NO:10) (CDRs are underlined and the difference from the parental antibody is shown in italics):

```
ELDVVMTQTP LTLSVTIGQP ASISCKSSQS LLYSNGKTYL

NWLLQRPGQS PKRLIYLVSK LDSGVPDRFT GSGSGTDFTL

KISRVEAEDL GVYYCVQGTH SPLTFGAGTK LELK
```

The Heavy Chain Variable Domain of scFv235 has the amino acid sequence (SEQ ID NO:11) (CDRs are underlined):

```
LEVQLQQSGP ELVKPGASVK ISCKTSEYTF TEYTKHWVKQ

SHGKSLEWIG SINPNNGDTY YNQKFTDKAT LTVDKSSTTA

SMELRSLTFE DSAVYYCAMG DSAWFAYWGQ GTLVTVS
```

Thus, the Light Chain Variable Domain CDR1 of scFv235 and antibody 6B2G12 both have the amino acid sequence (SEQ ID NO:12): KSSQSLLYSNGKTYLN.

The Light Chain Variable Domain CDR2 of scFv235 and antibody 6B2G12 both have the amino acid sequence (SEQ ID NO:13): LVSKLDS.

The Light Chain Variable Domain CDR3 of scFv235 and antibody 6B2G12 both have the amino acid sequence (SEQ ID NO:14): VQGTHSPLT.

The Heavy Chain Variable Domain CDR1 of scFv235 and antibody 6B2G12 both have the amino acid sequence (SEQ ID NO:15): EYTFTEYTKH.

The Heavy Chain Variable Domain CDR2 of scFv235 and antibody 6B2G12 both have the amino acid sequence (SEQ ID NO:16): SINPNNGDTYYNQKFTD.

The Heavy Chain Variable Domain CDR3 of scFv235 and antibody 6B2G12 both have the amino acid sequence (SEQ ID NO:17): GDSAWFAY.

The complete sequence of scFv235 is (SEQ ID NO:18):

```
ELDVVMTQTP LTLSVTIGQP ASISCKSSQS LLYSNGKTYL

NWLLQRPGQS PKRLIYLVSK LDSGVPDRFT GSGSGTDFTL

KISRVEAEDL GVYYCVQGTH SPLTFGAGTK LELKSSGGGG

SGGGGGGSSR SSLEVQLQQS GPELVKPGAS VKISCKTSEY

TFTEYTKHWV KQSHGKSLEW IGSINPNNGD TYYNQKFTDK

ATLTVDKSST TASMELRSLT FEDSAVYYCA MGDSAWFAYW

GQGTLVTVSA
``` wherein amino acid residues 1-114 are the amino acid residues of the Light Chain Variable Domain of scFv235 (SEQ ID NO:10), amino acid residues 115-132 are the amino acid residues of the linker (SEQ ID NO:4), amino acid residues 133-249 are the amino acid residues of the Heavy Chain Variable Domain of scFv235 (SEQ ID NO:11).

In a preferred embodiment, scFv235 is prepared as a fusion protein that includes an N-terminal leader peptide portion having the amino acid sequence (SEQ ID NO:19): IQEEFKMKKTAIAIAVALAGFATVAQAA, and/or a C-terminal sequence peptide portion. The C-terminal sequence peptide portion may include: an antibody constant domain, such as (SEQ ID NO:20): AKTTPPSVTSGQAGQ (Hussein, A. H. et al. (2007) "*Construction and Characterization of Single-Chain Variable Fragment Antibodies Directed against the Bordetella pertussis Surface Adhesins Filamentous Hemagglutinin and Pertactin*," Infect. Immun. 75(11): 5476-5482), a His-Tag, such as (SEQ ID NO:5): HHHHHH), and/or an HA-Tag such as (SEQ ID NO:6): GAYPYDVPDYAS, or any combination or sub-combination thereof, and in any order. A preferred C-terminal peptide portion has the amino acid sequence (SEQ ID NO:21): AKTTPPSVTSGQAGQHHHHHHGAYPYDVPDYAS, and thus includes (in the N-terminus to C-Terminus direction) SEQ ID NO:20, SEQ ID NO:5, and SEQ ID NO:6.

Thus, in a preferred embodiment, the scFv235 fusion protein will comprise the amino acid sequence of any of SEQ ID Nos:22-26 (in which the N-terminal and/or C-Terminal peptide portions of the ScFv fusion are underlined):

(a fusion of SEQ ID NOs: 19 and 18):
SEQ ID NO: 22

IQEEFKMKKT AIAIAVALAG FATVAQAAEL DVVMTQTPLT
LSVTIGQPAS ISCKSSQSLL YSNGKTYLNW LLQRPGQSPK
RLIYLVSKLD SGVPDRFTGS GSGTDFTLKI SRVEAEDLGV

-continued

YYCVQGTHSP LTFGAGTKLE LKSSGGGGSG GGGGGSSRSS
LEVQLQQSGP ELVKPGASVK ISCKTSEYTF TEYTKHWVKQ
SHGKSLEWIG SINPNNGDTY YNQKFTDKAT LTVDKSSTTA
SMELRSLTFE DSAVYYCAMG DSAWFAYWGQ GTLVTVSA (a fusion of SEQ ID NOs: 18 and 20):
SEQ ID NO: 23

ELDVVMTQTP LTLSVTIGQP ASISCKSSQS LLYSNGKTYL
NWLLQRPGQS PKRLIYLVSK LDSGVPDRFT GSGSGTDFTL
KISRVEAEDL GVYYCVQGTH SPLTFGAGTK LELKSSGGGG
SGGGGGGSSR SSLEVQLQQS GPELVKPGAS VKISCKTSEY
TFTEYTKHWV KQSHGKSLEW IGSINPNNGD TYYNQKFTDK
ATLTVDKSST TASMELRSLT FEDSAVYYCA MGDSAWFAYW
GQGTLVTVSA AKTTPPSVTS GQAGQ

(a fusion of SEQ ID NOs: 18 and 21):
SEQ ID NO: 24

ELDVVMTQTP LTLSVTIGQP ASISCKSSQS LLYSNGKTYL
NWLLQRPGQS PKRLIYLVSK LDSGVPDRFT GSGSGTDFTL
KISRVEAEDL GVYYCVQGTH SPLTFGAGTK LELKSSGGGG
SGGGGGGSSR SSLEVQLQQS GPELVKPGAS VKISCKTSEY
TFTEYTKHWV KQSHGKSLEW IGSINPNNGD TYYNQKFTDK
ATLTVDKSST TASMELRSLT FEDSAVYYCA MGDSAWFAYW
GQGTLVTVSA KTTPPSVTSG QAGQHHHHHH GAYPYDVPDY AS

(a fusion of SEQ ID NOs: 19, 18 and 20):
SEQ ID NO: 25

IQEEFKMKKT AIAIAVALAG FATVAQAAEL DVVMTQTPLT
LSVTIGQPAS ISCKSSQSLL YSNGKTYLNW LLQRPGQSPK
RLIYLVSKLD SGVPDRFTGS GSGTDFTLKI SRVEAEDLGV
YYCVQGTHSP LTFGAGTKLE LKSSGGGGSG GGGGGSSRSS
LEVQLQQSGP ELVKPGASVK ISCKTSEYTF TEYTKHWVKQ
SHGKSLEWIG SINPNNGDTY YNQKFTDKAT LTVDKSSTTA
SMELRSLTFE DSAVYYCAMG DSAWFAYWGQ GTLVTVSAAK
TTPPSVTSGQ AGQ

(a fusion of SEQ ID NOs: 19, 18 and 21):
SEQ ID NO: 26

IQEEFKMKKT AIAIAVALAG FATVAQAAEL DVVMTQTPLT
LSVTIGQPAS ISCKSSQSLL YSNGKTYLNW LLQRPGQSPK
RLIYLVSKLD SGVPDRFTGS GSGTDFTLKI SRVEAEDLGV
YYCVQGTHSP LTFGAGTKLE LKSSGGGGSG GGGGGSSRSS
LEVQLQQSGP ELVKPGASVK ISCKTSEYTF TEYTKHWVKQ
SHGKSLEWIG SINPNNGDTY YNQKFTDKAT LTVDKSSTTA
SMELRSLTFE DSAVYYCAMG DSAWFAYWGQ GTLVTVSAAK
TTPPSVTSGQ AGQHHHHHHG AYPYDVPDYA S

Although scFv are able to transit across the blood-brain barrier, various ancillary approaches may be used to further promote such transit (Huang, L. et al. (2013) "*Single-Chain*

*Fragment Variable Passive Immunotherapies For Neurodegenerative Diseases,*" Int. J. Mol. Sci. 14(9):19109-19127).

A limited set of proteins and peptides are transported across the blood-brain barrier via receptor-mediated transcytosis (Hervé, F. et al. (2008) "*CNS Delivery Via Adsorptive Transcytosis,*" AAPS J. 10(3):455-472), the three best-studied ligands being insulin, iron-transferrin and LDL-cholesterol (Bickel, U. et al. (2001) "*Delivery Of Peptides And Proteins Through The Blood-Brain Barrier,*" Adv. Drug Deliv. Rev. 46:247-279; Tuma, P. L. et al. (2003) "*Transcytosis: Crossing Cellular Barriers,*" Physiol. Rev. 83:871-932). Thus, transport of an scFv across the blood-brain barrier can be promoted by fusing the scFv to an antibody, or an epitope-binding fragment thereof, that is immunospecific for a receptor of such ligands (e.g., the human insulin receptor (HIR), the transferrin receptor (TfR), low density lipoprotein receptor-related proteins 1 (LRP1) and 2 (LRP2), non-toxic diphtheria toxin receptor/Heparin binding epidermal growth factor-like growth factor, etc). The resulting fusion protein can be transported across the blood-brain barrier through its binding to the receptor (Boado, R. J. et al. (2010) "*IgG-Single Chain Fv Fusion Protein Therapeutic For Alzheimer's Disease: Expression In CHO cells And Pharmacokinetics And Brain Delivery In The Rhesus Monkey,*" Biotechnol. Bioeng. 105:627-635; Jones, A. R. et al. (2007) "*Blood-Brain Barrier Transport Of Therapeutics Via Receptor-Mediation,*" Pharm. Res. 24(9):1759-1771; Wang, Y. Y. et al. (2009) "*Receptor-Mediated Therapeutic Transport Across The Blood-Brain Barrier,*" Immunotherapy 1(6):983-993; Lajoie, J. M. et al. (2015) "*Targeting Receptor-Mediated Transport For Delivery Of Biologics Across The Blood-Brain Barrier,*" Annu. Rev. Pharmacol. Toxicol. 55:613-631; Pardridge, W. M. (2102) "*Drug Transport Across The Blood-Brain Barrier,*" J. Cereb. Blood Flow Metab. 32(11):1959-1972; Bhaskar, S. et al. (2010) "*Multifunctional Nanocarriers For Diagnostics, Drug Delivery And Targeted Treatment Across Blood-Brain Barrier: Perspectives On Tracking And Neuroimaging,*" Part. Fibre. Toxicol. 7:3 pp. 1-25).

The scFv may be augmented to contain a polycationic peptide that facilitates adsorptive-mediated transcytosis. Suitable polycationic peptides include hexamethylene-diamine, putrescine, spermidine and spermine (Hervé, F. et al. (2008) "*CNS Delivery Via Adsorptive Transcytosis,*" AAPS J. 10(3):455-472; Kandimalla, K. K. et al. (2006) "*Physiological And Biophysical Factors That Influence Alzheimer's Disease Amyloid Plaque Targeting Of Native And Putrescine Modified Human Amyloid Beta40,*" J. Pharmacol. Exp. Ther. 318:17-25). The scFv may be augmented to comprise polycationic groups via treatment that amidates some or all of its carboxylic groups (i.e., the carboxy-terminal group, or the carboxylic side chains of glutamate or aspartate residue(s) of the scFv).

Alternatively, the scFv may be augmented to contain a cell-penetrating peptide ("CPP") (Rao, K. S. et al. (2009) "*Targeting Anti-HIV Drugs To The CNS,*" Expert Opin. Drug Deliv. 6(8):771-784; Mathupala, S. P. et al. (2009) "*Delivery Of Small-Interfering RNA (siRNA) To The Brain,*" Expert Opin. Ther. Pat. 19(2):137-140; Hervé, F. et al. (2008) "*CNS Delivery Via Adsorptive Transcytosis,*" AAPS J. 10(3):455-472). Such peptides include the HIV-1 trans-activating transcriptional activator (TAT) peptide, the Herpes Simplex Virus type-1 transcription factor (HSV VP-22) peptide, antennapedia and penetratin (Wadia, J. S. et al. (2004) "*Transducible TAT-HA Fusogenic Peptide Enhances Escape Of TAT-Fusion Proteins After Lipid Raft Macropinocytosis,*" Nat. Med. 10:310-315; Richard, J. P. et al. (2003) "*Cell-Penetrating Peptides. A Reevaluation Of The Mechanism Of Cellular Uptake,*" J. Biol. Chem. 278:585-590; Temsamani, J. et al. (2004) "*The Use Of Cell-Penetrating Peptides For Drug Delivery,*" Drug Discov. Today 9:1012-1019).

III. Uses of the Antibodies and Antibody Fragments of the Present Invention

The present invention relates to the use of Tau-immunospecific, phospho-Tau-selective, antibodies or Tau-immunospecific, phospho-Tau-selective binding fragments thereof to diagnose and/or treat Alzheimer's disease or tauopathy in a subject patient. With respect to such diagnostic utility, such uses may involve detecting, in the subject (i.e., in vivo), the presence of a pathological Tau conformer using the 6B2G12 antibody of the present invention, or an epitope-binding fragment thereof (especially scFv235), that has preferably been detectably labeled (such molecules being collectively referred to herein as the diagnostic molecules of the present invention). Alternatively, such uses may involve detecting the presence of a pathological Tau conformer ex vivo (e.g., in a biopsy sample, or post-mortem) using the diagnostic molecules of the present invention.

In one embodiment, such Tau-immunospecific, phospho-Tau-selective, antibodies or Tau-immunospecific, phospho-Tau-selective binding fragments may be humanized antibodies.

With respect to such therapeutic utility, such uses may involve the administration of a therapeutically effective amount of the 6B2G12 antibody of the present invention, or of an epitope-binding fragment thereof (especially scFv235) to a patient having one or more symptoms of Alzheimer's disease or such tauopathy, and thus in need of such therapy, or it may involve the administration of a prophylactically effective amounts of the 6B2G12 antibody of the present invention, or of an epitope-binding fragment thereof (especially scFv235) to a patient not exhibiting such symptoms, or exhibiting symptoms of mild dementia or pre-tauopathy that is indicative of incipient Alzheimer's disease or tauopathy, such molecules being collectively referred to herein as the therapeutic molecules of the present invention.

As described supra, the preferred scFv antibody (scFv235) has specificity for P-Ser 396/404, however, scFv molecules having specificity for other Tau peptide(s), for example, those described in US 2008/0050383, may be used in concert with scFv235.

The term "tauopathy," as used herein, encompasses any neurodegenerative disease that involves the pathological aggregation of the microtubule protein Tau within the brain. Accordingly, in addition to both familial and sporadic Alzheimer's disease, the tauopathies of the present invention include, without limitation, frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

IV. Production of the Tau-Binding Molecules of the Present Invention

The Tau-binding molecules of the present invention are preferably produced via the recombinant expression of a nucleic acid molecule that encodes their constituent polypeptide chain(s). The invention thus accordingly also relates to an expression vector encoding such one or more polypeptide chains of an antibody of the invention or a fragment thereof.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-Tau antibody-encoding nucleic acid is comprised in a naked DNA or RNA vector, including, for example, a linear expression element (as described in, for instance, Sykes, K. F. and Johnston S. A. (1999) "*Linear Expression Elements: A Rapid, in vivo, Method To Screen For Gene Functions,*" Nat. Biotechnol. 12:355-359), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski, F. et al. (2001) "*A Novel Minimal-Size Vector (MIDGE) Improves Transgene Expression In Colon Carcinoma Cells And Avoids Transfection Of Undesired DNA,*" Mol. Ther. 3, 793-800 (2001)), or as a precipitated nucleic acid vector construct, such as a $CaPO_4$-precipitated construct (as described in, for instance, WO 00/46147, Benvenisty, N. and Reshef, L. (1986) "*Direct Introduction Of Genes Into Rats And Expression Of The Genes,*" Proc. Natl. Acad. Sci. (U.S.A.) 83:9551-9555, Wigler, M. et al. (1978) "*Biochemical Transfer Of Single-Copy Eucaryotic Genes Using Total Cellular DNA As Donor,*" Cell 14, 725 (1978), and Corsaro, C. M. and Pearson, M. L. (1981) "*Enhancing The Efficiency Of DNA-Mediated Gene Transfer In Mammalian Cells,*" Somatic Cell Genetics 2:603-616). Such nucleic acid vectors and the usage thereof are well known in the art (see for instance U.S. Pat. Nos. 5,589,466 and 5,973,972).

In one embodiment, the vector is suitable for expression of an anti-Tau antibody or a Tau-binding fragment thereof in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison, Wis.) and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Bitter, G. A. et al. (1987) "*Expression And Secretion Vectors For Yeast,*" Methods Enzymol. 153:516-544).

In an expression vector of the invention, an anti-Tau antibody-encoding nucleic acid molecule (or a nucleic acid molecule encoding a Tau-binding fragment thereof) may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, which produces an antibody of the invention as defined herein or a bispecific molecule of the invention as defined herein. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of an anti-Tau antibody of the present invention or a Tau-binding fragment thereof. In another embodiment, the present invention provides a cell comprising a non-integrated nucleic acid, such as a plasmid, cosmid, phagemid, or linear expression element, which comprises a sequence coding for expression of an anti-Tau antibody of the present invention, or such fragment thereof.

In a further aspect, the invention relates to a method for producing an anti-Tau antibody of the present invention, said method comprising the steps of a) culturing a hybridoma or a host cell of the invention as described herein above, and b) purifying the antibody of the invention from the culture media.

In general, the produced anti-Tau antibodies and Tau-binding fragments thereof may be modified by inclusion of any suitable number of modified amino acids and/or associations with such conjugated substituents. Suitability in this context is generally determined by the ability to at least substantially retain anti-Tau selectivity and/or the anti-Tau specificity associated with the non-derivatized parent anti-Tau antibody. The inclusion of one or more modified amino acids may be advantageous in, for example, increasing polypeptide serum half-life, reducing polypeptide antigenicity, or increasing polypeptide storage stability. Amino acid (s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e. g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) *Protein Protocols On CD-Rom*, Humana Press, Totowa, N.J. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

As indicated above, when it is desired to increase the half-life of an administered therapeutic molecule of the present invention, such molecules may be formed to comprise carbohydrate moieties, such as polyoxyethylated polyols or polyethylene glycol (PEG) (e.g., a PEG with a molecular weight of between about 1,000 and about 40,000, such as between about 2,000 and about 20,000, e.g., about 3,000-12,000 g/mol) (Moosmann, A. et al. (2014) *"Purification Of PEGylated Proteins, With The Example Of PEGylated Lysozyme and PEGylated scFv,"* Methods Mol. Biol. 1129:527-538; Jevsevar, S. et al. (2010) *"PEGylation Of Therapeutic Proteins,"* Biotechnol. J. 5:113-228), or through glycosylation or by adding or associating proteins such as human serum albumin (Müller, M. R. et al. (2012) *"Improving The Pharmacokinetic Properties Of Biologics By Fusion To An Anti-HSA Shark VNAR Domain,"* MAbs. 4(6):673-685; Stork, R. et al. (2008) *"N-Glycosylation As Novel Strategy To Improve Pharmacokinetic Properties Of Bispecific Single-Chain Diabodies,"* J. Biol. Chem. 283: 7804-7812; Alt, M. et al. (1999) *"Novel Tetravalent And Bispecific IgG-like Antibody Molecules Combining Single-Chain Diabodies With The Immunoglobulin Gammal Fc or CH3 Region,"* FEBS Lett. 454:90-94; Peters T. et al. (1985) *"Serum Albumin,"* Adv. Protein Chem. 37:161-245). Illustrative polymers and methods to attach them to peptides, are known, (see, for example, U.S. Pat. Nos. 4,766,106; 4,179,337; 4,495,285 and 4,609,546).

V. Pharmaceutical Compositions of the Present Invention

The Tau-binding molecules of the present invention are often administered as pharmaceutical compositions comprising an active therapeutic agent and a variety of other pharmaceutically acceptable components. See REMINGTON: THE SCIENCE AND PRACTICE OF PHARMACY ($21^{st}$ Edition) (2005) (Troy, D. B. et al. (Eds.) Lippincott Williams & Wilkins (Publs.), Baltimore Md.), which is hereby incorporated by reference in its entirety. The preferred form depends on the intended mode of administration and therapeutic application. The compositions can also include, depending on the formulation desired, pharmaceutically acceptable, non-toxic carriers, excipients, diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition, and which are vehicles commonly used to formulate pharmaceutical compositions for animal or human administration. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on antigen binding.

The pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or nonaqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

For parenteral administration, agents of the present invention are typically formulated as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention can be administered in the form of a depot injection or implant preparation which can be formulated in such a manner as to permit a sustained release of the active ingredient. An exemplary composition comprises scFv235 at about 5 mg/mL, formulated in aqueous buffer consisting of 50 mM L-histidine, 150 mM NaCl, adjusted to pH 6.0 with HCl.

Typically, compositions are thus prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, G. et al. (1990) "*New Methods of Drug Delivery*," Science 249:1527-1533; Langer, G. et al. (1997) "*New Advances In Microsphere-Based Single-Dose Vaccines*," Advanced Drug Delivery Reviews 28:97-119 (1997), which are hereby incorporated by reference in their entirety). Additional formulations suitable for other modes of administration include oral, intranasal, and pulmonary formulations, suppositories, and transdermal applications.

VI. Administration of the Pharmaceutical Compositions of the Present Invention

The molecules of the present invention can be administered by parenteral, topical, oral or intranasal means for prophylactic and/or therapeutic treatment. Intramuscular injection (for example, into the arm or leg muscles) and intravenous infusion are preferred methods of administration of the molecules of the present invention. In some methods, such molecules are administered as a sustained release composition or device, such as a Medipad™ device (Elan Pharm. Technologies, Dublin, Ireland). In some methods, the molecules of the present invention are injected directly into a particular tissue where deposits have accumulated, for example intracranial injection.

In one embodiment, a pharmaceutical composition of the present invention is administered parenterally. The phrases "parenteral administration" and "administered parenterally" as used herein denote modes of administration other than enteral and topical administration, usually by injection, and include epidermal, intravenous, intramuscular, intraarterial, intrathecal, intracapsular, intracranial, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection, subcutaneous and infusion. In one embodiment that pharmaceutical composition is administered by intravenous or subcutaneous injection or infusion.

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presented during development of the disease.

In therapeutic applications (i.e., in applications involving a patient who has been diagnosed as having Alzheimer's disease or other tauopathy) the therapeutic molecules of the present invention are administered to such patient in an amount sufficient to cure, treat, or at least partially arrest, the symptoms of the disease (as adduced by biochemical, histologic and/or behavioral assessment), including its complications and intermediate pathological phenotypes in development of the disease. In some embodiments, the administration of the therapeutic molecules of the present invention reduces or eliminates mild cognitive impairment in patients that have not yet developed characteristic Alzheimer's pathology.

Effective doses of the provided therapeutic molecules of the present invention, for the treatment of the above-described conditions may vary depending upon many different factors, including means of administration, target site, physiological state of the patient, other medications administered, and whether treatment is prophylactic or therapeutic. Treatment dosages are typically titrated to optimize their safety and efficacy. On any given day that a dosage is given, the dosage may range from about 0.0001 to about 100 mg/kg, and more usually from about 0.01 to about 5 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight A physician or veterinarian having ordinary skill in the art may readily determine and prescribe the effective amount of the pharmaceutical composition required. For example, the physician or veterinarian could start doses of the anti-Tau antibody or fragment employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

An exemplary treatment regime entails administration once per every two weeks or once a month or once every 3 to 6 months. In some methods, one, two or more antibodies (or epitope-binding fragments thereof) will be administered in conjunction with the administration of the therapeutic molecules of the present invention, in which case the dosage of each such administered molecule falls within the ranges indicated.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered such therapeutic molecule using a prophylactic dosage regime.

For therapeutic purposes, the molecules of the present invention are usually administered on multiple occasions. Intervals between single dosages (e.g., a bolus or infusion) can be weekly, monthly, or yearly. In some methods, dosage is adjusted to achieve a plasma concentration of 1-1000 µg/ml and in some methods 25-300 µg/ml. Alternatively, the therapeutic molecules of the present invention can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. scFv molecules generally have short serum half-lives.

Another aspect of the present invention is a combination therapy wherein an additional antibody, or an epitope-binding fragment thereof, recognizing the Tau protein, or an immunogenic epitope thereof, is administered in combination with a therapeutic molecule of the present invention. In the case of amyloidogenic diseases such as, Alzheimer's disease and Down's syndrome, immune modulation to clear amyloid-beta (Aβ) deposits is an emerging therapy. Immunotherapies targeting Aβ have consistently resulted in cognitive improvements. It is likely that Tau and Aβ pathologies are synergistic. Therefore, a combination therapy targeting the clearance of both pathologies at the same time may be more effective than targeting each individually. In the case of Parkinson's Disease and related neurodegenerative diseases, immune modulation to clear aggregated forms of the α-synuclein protein is also an emerging therapy. A combination therapy which targets the clearance of both Tau and α-synuclein proteins simultaneously may be more effective than targeting each individually.

VII. Utility of the Tau-Binding Molecules of the Present Invention

A. Diagnostic Utility

Detecting the presence of a pathological Tau conformer in a subject using a diagnostic molecule of the present invention can be achieved by obtaining a biological sample from the subject (e.g., blood, urine, cerebral spinal fluid), contacting the biological sample with said diagnostic antibody, and detecting binding of the diagnostic molecule to a pathological Tau protein conformer in the sample from the subject. Assays for carrying out the detection of a pathological Tau protein in a biological sample that may be readily adapted to the detection of the diagnostic molecules of the present invention are well known in the art and include, without limitation, ELISA, immunohistochemistry, Western blot.

Alternatively, detecting the presence of a pathological Tau protein conformer in a subject using a diagnostic molecule of the present invention can be achieved using in vivo imaging techniques. In vivo imaging involves administering to the subject the diagnostic antibody having antigenic specificity for a pathological Tau peptide and detecting binding of the diagnostic antibody reagent to the pathological Tau protein conformer in vivo.

The diagnostic molecules of the present invention can be administered by injection (e.g., intravenous injection, intracarotid injection, etc.) into the body of the patient, or directly into the brain by intracranial injection. The dosage of such molecule should be from about 0.0001 mg/kg to about 100 mg/kg, and more usually from about 0.01 mg/kg to about 5 mg/kg, of the host body weight. For example dosages can be about 1 mg/kg body weight or about 10 mg/kg body weight or within the range of about 1-10 mg/kg.

Typically, the diagnostic molecules of the present invention is labeled, although in some methods, the molecule may be unlabeled and a secondary labeling agent is used to bind to such molecule (coupled or conjugated either directly to the molecule or indirectly, through an intermediate (such as, for example, a linker known in the art) using techniques known in the art). The choice of label depends on the means of detection. For example, a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, is suitable for optical detection. Chemoluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels and radioisotopic labels can also be employed, and are preferably detected using Positron Emission Tomography (PET) or Single-Photon Emission Computed Tomography (SPECT). Radiolabels include, but are not limited to, bismuth ($^{213}$Bi), carbon ($^{11}$C, $^{13}$C, $^{14}$C), chromium ($^{51}$Cr), cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho), hydrogen ($^{3}$H), indium ($^{111}$In, $^{112}$In, $^{113}$In, $^{115}$In), iodine ($^{121}$I, $^{123}$I, $^{125}$I, $^{131}$I), iridium ($^{192}$Ir), iron ($^{59}$Fe), krypton ($^{81m}$Kr), lanthanum ($^{140}$La), lutetium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium(186Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y) and zinc ($^{65}$Zn); positron emitting metals using various positron emission tomographies, and non-radioactive paramagnetic metal ions (such as paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (0), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581; 4,735,210; 5,101,827; 5,102,990; RE 35,500; 5,648,471 and 5,697,902. For example, a radioisotope may be conjugated by a chloramine T method (Lindegren, S. et al. (1998) "*Chloramine-T In High-Specific-Activity Radioiodination Of Antibodies Using N-Succinimidyl-3-(Trimethylstannyl) Benzoate As An Intermediate*," Nucl. Med. Biol. 25(7):659-665; Kurth, M. et al. (1993) "*Site-Specific Conjugation Of A Radioiodinated Phenethylamine Derivative To A Monoclonal Antibody Results In Increased Radioactivity Localization In Tumor*," J. Med. Chem. 36(9):1255-1261; Rea, D. W. et al. (1990) "Site-specifically radioiodinated antibody for targeting tumors," Cancer Res. 50(3 Suppl):857s-861s).

Diagnosis is performed by comparing the number, size, and/or intensity of labeled pathological Tau conformers, Tau aggregates, and/or neurofibrillary tangles in a sample from the subject or in the subject, to corresponding baseline values. The base line values can represent the mean levels in a population of non-diseased individuals. Baseline values can also represent previous levels determined in the same subject.

The diagnostic methods described above can also be used to monitor a subject's response to therapy. In this embodiment, detecting the presence of pathological Tau in a subject is determined prior to the commencement of treatment. The level of pathological Tau in the subject at this time point is used as a baseline value. At various times during the course of treatment the detection of pathological Tau protein conformers, Tau aggregates, and/or neurofibrillary tangles is repeated, and the measured values thereafter compared with the baseline values. A decrease in values relative to baseline signals a positive response to treatment. Values can also increase temporarily in biological fluids as pathological Tau is being cleared from the brain.

The present invention is further directed to a kit for performing the above-described diagnostic and monitoring methods. Typically, such kits contain the diagnostic antibody of the present invention. The kit can also include a detectable label. The diagnostic antibody itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring pathological Tau protein in a biological sample, the antibodies of the kit may be supplied pre-bound to a solid phase, such as to the wells of a microtiter dish.

B. Therapeutic Utility

The presence of labeled anti-Tau antibodies or their Tau-binding fragments may be detected in vivo for diagnosis purposes. In one embodiment, such diagnosis comprises: a) administering to a subject an effective amount of such labeled molecule; b) waiting for a time interval following administration in order to allow the labeled molecule to concentrate at sites (if any) of aggregated Tau and to allow unbound labeled molecule to be cleared to a background level; c) determining a background level; and d) detecting such labeled molecule in the subject, such that detection of labeled molecule above the background level is indicative that the subject has a tauopathy, or is indicative of the severity of such tauopathy. In accordance with such embodiment, the antibody is labeled with an imaging moiety suitable for detection using a particular imaging system known to those skilled in the art. Background levels may be determined by various methods known in the art, including comparing the amount of labeled molecule detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

The term "treatment" or "treating" as used herein means ameliorating, slowing or reversing the progress or severity of a disease or disorder, or ameliorating, slowing or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," when applied to an antibody of the invention, refers to an amount sufficient, at dosages and for periods of time necessary, to achieve an intended biological effect or a desired therapeutic result including, without limitation, clinical results. The phrase "therapeutically effective amount" when applied to an antibody of the invention is intended to denote an amount of the antibody that is sufficient to ameliorate, palliate, stabilize, reverse, slow or delay the progression of a disorder or disease state, or of a symptom of the disorder or disease. In an embodiment, the method of the present invention provides for administration of the antibody in combinations with other compounds. In such instances, the "effective amount" is the amount of the combination sufficient to cause the intended biological effect.

As indicated above, one aspect of the present invention relates to a method of preventing or treating Alzheimer's disease or other tauopathy in a subject via the administration of an effective amount of antibody 6B2G12 or of an epitope-binding fragment thereof (especially scFv235) to prevent or treat such Alzheimer's disease or other tauopathy. Such administration may be provided in order to promote the clearance of Tau aggregates from the brain of a subject or may be provided in order to slow a tangle-related behavioral phenotype in a subject. Additionally, such administration may be provided prophylactically in order to delay, impede, attenuate or prevent the onset of Alzheimer's disease, or other tauopathy associated with the neurofibrillary tangle. An amount adequate to accomplish therapeutic or prophylactic treatment is defined, respectively, as a therapeutically effective dose or a prophylactically effective dose. In both prophylactic and therapeutic regimes, agents are usually administered in several dosages until a sufficient immune response has been achieved. Typically, the immune response is monitored and repeated dosages are given if the immune response starts to wane. A therapeutically effective or prophylactically effective dose of such an antibody or epitope-binding fragment thereof may vary according to factors such as the disease state, age, sex, and weight of the individual, and the ability of the molecule to elicit a desired response in the subject. A therapeutically effective amount is also one in which any toxic or detrimental effects of the antibody or antibody portion are outweighed by the therapeutically beneficial effect.

Patients amenable to treatment include individuals having Alzheimer's disease or such other tauopathy who show clinically recognized symptoms or indications of such conditions, as well as patients not presently showing symptoms of such conditions. Although Alzheimer's disease is definitively diagnosed only post-mortem biopsy, individuals suffering from Alzheimer's disease are clinically diagnosed using the "*Alzheimer's Disease and Related Disorders Association*" ("ADRDA") Criteria (Carrillo, M. C. et al. (2013) "*Revisiting The Framework Of The National Institute On Aging-Alzheimer's Association Diagnostic Criteria*," Alzheimers Dement. 9(5):594-601; Budson, A. E. et al. (2012) "*New Criteria For Alzheimer Disease And Mild Cognitive Impairment: Implications For The Practicing Clinician*," Neurologist 18(6):356-363; Sarazin, M. et al. (2012) "*Clinical And Research Diagnostic Criteria For Alzheimer's Disease*," Neuroimaging Clin. N. Amer. 22(1):23-32; Husain, M. M. (2005) "*Clinical Diagnosis And Management Of Alzheimer's Disease*," Neuroimaging Clin. N. Amer. 15(4):767-777; Small, G. W. et al. (1997) "*Diagnosis And Treatment Of Alzheimer Disease And Related Disorders. Consensus Statement Of The American Association For Geriatric Psychiatry, The Alzheimer's Association, And The American Geriatrics Society*," JAMA 278(16):1363-1371). Such individuals can alternatively be distinguished from those having diseases or conditions that are un-related to Alzheimer's disease or other tauopathy by the presence of correlated risk factors (i.e., one or more factors that have been found to possess greater than 50% coincidence with Alzheimer's disease or such other tauopathy). Such correlated risk factors include the finding that a patient has had relatives who have experienced Alzheimer's disease or such other tauopathy, or present a family history of hypercholesterolemia or atherosclerosis. Such correlated risk factors particularly include the finding that a patient possesses one or more genetic or biochemical markers that have been correlated with (i.e., found to possess greater than 50% coincidence with) the occurrence of such actual disease. Examples of such genetic markers of risk toward Alzheimer's disease include correlated mutations in the APP gene, for example, mutations at position 717 and positions 670 and 671 of the APP gene (referred to as the Hardy and Swedish mutations respectively). Other suitable markers of known genetic risk include correlated mutations in the presenilin genes (PS1 and PS2) and in the ApoE4 gene (Bekris, L. M. et al. (2010) "*Genetics of Alzheimer Disease*," J. Geriatr. Psychiatry Neurol. 23(4):213-227).

Such PS1 mutations include the substitutions: R35Q; A79V; V82L; L85P; V89L; V94M; V96F; V97L; F105I; F105L; F105V; L113P; L113Q; Y115C; Y115D; Y115H; T116I; T116N; P117A; P117L; P117R; P117S; E120D; E120D; E120G; E120K; E123K; N135D; N135S; A136G; M139I; M139I; M139K; M139T; M139V; I143F; I143M; I143N; I143T; I143V; M146I; M146I; M146I; M146L; M146L; M146V; T147I; L153V; Y154C; Y154N; H163R; H163Y; W165C; W165G; L166H; L166P; L166R; S169L; S169P; S170F; L171P; L173F; L173W; L174M; L174R; F175S; F177L; F177S; S178P; G183V; E184D; V191A; G206A; G206D; G206S; G206V; G209E; G209R; G209V; S212Y; I213F; I213L; I213T; H214D; H214Y; G217D; G217R; L219F; L219P; Q222H; Q222R; Q223R; L226F; L226R; I229F; A231T; A231V; M233I; M233L; M233L; M233T; M233V; L235P; L235V; F237I; F237L; K239N; T245P; A246E; L248R; L250S; L250V; Y256S; A260V; V261F; V261L; L262F; C263F; C263R; P264L; G266S; P267L; P267S; R269G; R269H; L271V; V272A; E273A; T274R; R278I; R278K; R278S; R278T; E280A; E280G; L282F; L282R; L282V; P284L; P284S; A285V; L286P; L286V; T291P; E318G; R358Q; S365A; R377M; G378E; G378V; L381V; G384A; F386S; S390I; V391F; L392P; L392V; G394V; N405S; A409T; C410Y; V412I; L418F; L420R; L424F; L424H; L424R; L424V; A426P; A431E; A431V; A434C; L435F; P436Q; P436S; and I439S.

Such PS2 mutations include the substitutions: R29H; G34S; R62C; R62H; R71W; A85V; T122P; T122R; S130L; V139M; N141I; L143H; V148I; R163H; M174V; S175C; Y231C; Q228L; M239V; M230I; A252T; P334R; T430M; and D439A.

Such ApoE4 alleles include the ε4 allele, ε3 allele and ε2 allele (Verghese, P. B. et al. (2011) "*Apolipoprotein E In Alzheimer's Disease And Other Neurological Disorders*," Lancet Neurol. 10(3):241-252).

In addition, a number of diagnostic tests are available for identifying individuals who have Alzheimer's disease. These include measurement of CSF Tau and Aβ342 levels. Elevated Tau and decreased Aβ342 levels signify the presence of Alzheimer's disease.

In the case of Alzheimer's disease, virtually anyone is at risk of suffering from Alzheimer's disease. Therefore, the therapeutic molecules of the present invention can be administered prophylactically to the general population without the need for any assessment of the risk of the subject patient. The present methods are especially useful for the prophylactic treatment of individuals who do have a known genetic risk of Alzheimer's disease. In asymptomatic patients, treatment can begin at any age (e.g., 10, 20, 30). Usually, however, it is not necessary to begin treatment until a patient reaches 40, 50, 60, 70, 80 or 90 years of age. Treatment typically entails the administration of multiple dosages over a period of time. Treatment can be monitored by assaying antibody, or activated T-cell or B-cell responses to the therapeutic agent over time. If the response falls, a booster dosage is indicated. In the case of potential Down's syndrome patients, treatment can begin ante-natally by administering the therapeutic agent to the mother during pregnancy or shortly after the patient's birth.

The present invention provides:
1. A binding molecule that is capable of immunospecifically binding to phosphorylated Tau with more than 2000 fold greater selectivity than for non-phosphorylated Tau, wherein the molecule is an antibody or an epitope-binding fragment thereof
2. The embodiment of such binding molecule, wherein the molecule is an epitope-binding fragment of an antibody.
3. The embodiment of such epitope-binding fragment of an antibody, wherein the epitope-binding fragment of an antibody is an scFv or a diabody.
4. The embodiment of any of the above-described binding molecules, wherein the molecule immunospecifically binds to the Tau 396/404 peptide (SEQ ID NO:7): TDH-GAEIVYKS SPVVSGDTS SPRHL, wherein the serine residues at positions 11 and 19 thereof are phosphorylated.
5. The embodiment of any of the above-described binding molecules, wherein the epitope-binding fragment comprises one or more of:
   (a) a Light Chain CDR1 having the amino acid sequence of SEQ ID NO:12;
   (b) a Light Chain CDR2 having the amino acid sequence of SEQ ID NO:13;
   (c) a Light Chain CDR3 having the amino acid sequence of SEQ ID NO:14;
   (d) a Heavy Chain CDR1 having the amino acid sequence of SEQ ID NO:15;
   (e) a Heavy Chain CDR2 having the amino acid sequence of SEQ ID NO:16; or
   (f) a Heavy Chain CDR3 having the amino acid sequence of SEQ ID NO:17.
6. The embodiment of any of the above-described binding molecules, wherein the epitope-binding fragment comprises:
   (a) a Light Chain CDR1 having the amino acid sequence of SEQ ID NO:12;
   (b) a Light Chain CDR2 having the amino acid sequence of SEQ ID NO:13;
   (c) a Light Chain CDR3 having the amino acid sequence of SEQ ID NO:14;
   (d) a Heavy Chain CDR1 having the amino acid sequence of SEQ ID NO:15;
   (e) a Heavy Chain CDR2 having the amino acid sequence of SEQ ID NO:16; and
   (f) a Heavy Chain CDR3 having the amino acid sequence of SEQ ID NO:17.
7. The embodiment of the above-described binding molecule having
   (a) a Light Chain CDR1 having the amino acid sequence of SEQ ID NO:12;
   (b) a Light Chain CDR2 having the amino acid sequence of SEQ ID NO:13;
   (c) a Light Chain CDR3 having the amino acid sequence of SEQ ID NO:14;
   (d) a Heavy Chain CDR1 having the amino acid sequence of SEQ ID NO:15;
   (e) a Heavy Chain CDR2 having the amino acid sequence of SEQ ID NO:16; and
   (f) a Heavy Chain CDR3 having the amino acid sequence of SEQ ID NO:17,
   wherein the molecule is scFv235 (SEQ ID NO:18).
8. The embodiment of any of the above-described binding molecules, which is detectably labeled.
9. The embodiment of any of the above-described detectably labeled binding molecules, wherein the detectable label is a fluorescent label, a chemoluminescent label, a paramagnetic label, a radioisotopic label or an enzyme label.
10. (A) The embodiment of any of the above-described detectably labeled binding molecules for use in the manufacture of a medicament for detecting or measuring the presence or amount of the phosphorylated Tau protein in the brain of a recipient subject, or
    (B) the use of any of the above-described detectably embodiments of labeled binding molecules for detecting or measuring the presence or amount of the phosphorylated Tau protein in the brain of a recipient subject.
11. (A) The embodiment of any of the above-described detectably labeled binding molecules for use in the manufacture of a medicament for detecting or measuring the presence or amount of the phosphorylated Tau protein in the brain of a recipient subject, or
    (B) the use of any of the above-described embodiments of detectably labeled binding molecules for detecting or measuring the presence or amount of the phosphorylated Tau protein in the brain of a recipient subject; wherein the detection or measurement comprises in vivo imaging of the binding molecule bound to the phosphorylated Tau protein.
12. (A) The embodiment of any of the above-described detectably labeled binding molecules for use in the manufacture of a medicament for detecting or measuring the presence or amount of the phosphorylated Tau protein in the brain of a recipient subject, or
    (B) the use of any of the above-described embodiments of detectably labeled binding molecules for detecting or measuring the presence or amount of the phosphorylated Tau protein in the brain of a recipient subject; wherein the detection or measurement comprises ex vivo imaging of the binding molecule bound to the phosphorylated Tau protein.
13. (A) (1) The embodiment of any of the above-described binding molecules, which is detectably labeled; or
    (2) the embodiment of any of the above-described detectably labeled binding molecules, wherein the detectable label is a fluorescent label, a chemoluminescent label, a paramagnetic label, a radioisotopic label or an enzyme label;
    for use in the manufacture of a medicament for diagnosing Alzheimer's disease or another tauopathy of a subject; or (B) (1) the use of any of the above-described embodiments of detectably labeled binding molecules for diagnosing Alzheimer's disease or another tauopathy of a subject; or
  (2) the use of any of the above-described embodiments of detectably labeled binding molecules, wherein the detectable label is a fluorescent label, a chemiluminescent label, a paramagnetic label, a radioisotopic label or an enzyme label, for diagnosing Alzheimer's disease or another tauopathy of a subject.
14. (A) (1) The embodiment of any of the above-described binding molecules, which is detectably labeled; or
  (2) the embodiment of any of the above-described detectably labeled binding molecules, wherein the detectable label is a fluorescent label, a chemiluminescent label, a paramagnetic label, a radioisotopic label or an enzyme label;
  for use in the manufacture of a medicament for diagnosing Alzheimer's disease or another tauopathy of a subject; or
(B) (1) the use of any of the above-described embodiments of detectably labeled binding molecules for diagnosing Alzheimer's disease or another tauopathy of a subject; or
  (2) the use of any of the above-described embodiments of detectably labeled binding molecules, wherein the detectable label is a fluorescent label, a chemiluminescent label, a paramagnetic label, a radioisotopic label or an enzyme label, for diagnosing Alzheimer's disease or another tauopathy of a subject;
  wherein the medicament is an in vivo medicament that is administered to the subject.
15. (A) (1) The embodiment of any of the above-described binding molecules, which is detectably labeled; or
  (2) the embodiment of any of the above-described detectably labeled binding molecules, wherein the detectable label is a fluorescent label, a chemiluminescent label, a paramagnetic label, a radioisotopic label or an enzyme label;
  for use in the manufacture of a medicament for diagnosing Alzheimer's disease or another tauopathy of a subject; or
(B) (1) the use of any of the above-described embodiments of detectably labeled binding molecules for diagnosing Alzheimer's disease or another tauopathy of a subject; or
  (2) the use of any of the above-described embodiments of detectably labeled binding molecules, wherein the detectable label is a fluorescent label, a chemiluminescent label, a paramagnetic label, a radioisotopic label or an enzyme label, for diagnosing Alzheimer's disease or another tauopathy of a subject;
  wherein the medicament is incubated ex vivo with a biopsy sample of the subject.
16. The embodiment of any of such uses, wherein the tauopathy is selected from the group comprising frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

EXAMPLES

The following examples illustrate various methods for compositions in the diagnostic or treatment methods of the invention. The examples are intended to illustrate, but in no way limit, the scope of the invention.

Example 1

Isolation of scFv235 scFv molecules were generated from hybridoma clone 6B2G12 (raised against P-Ser396/404 of the Tau protein) (Congdon, E. E. et al. (2013) "*Antibody Uptake into Neurons Occurs Primarily via Clathrin-dependent Fcgamma Receptor Endocytosis and Is a Prerequisite for Acute Tau Protein Clearance*," J. Biol. Chem. 288:35452-35465; Gu, J. et al. (2013) "*Two Novel Tau Antibodies Targeting The 396/404 Region Are Primarily Taken Up By Neurons And Reduce Tau Protein Pathology*," J. Biol. Chem. 288(46):33081-33095). Briefly, the hybridoma cell line 6B2G12 was grown at 37° C. with 5% $CO_2$ in RPMI medium containing streptomycin (50 µg/ml) and Penicillin G (50 U/ml), and its mRNA was isolated and purified as per the protocol of an RNA isolation kit (Promega), and subsequently stored at −80° C. The first strand cDNA was constructed as per the protocol of a first strand cDNA synthesis kit (Takara kit (TAK6115A)).

Clones were screened for their ability to express scFv molecules that were immunospecific for the P-Ser396, 404 Tau epitope using peptides (Keck Foundation, Yale University) having the sequences of Tau-serine 396/404 (SEQ ID NO:27):

```
RENAKAKTDHGAEIVYKSPVVSGDTSPRHL
and

Figure 1A:
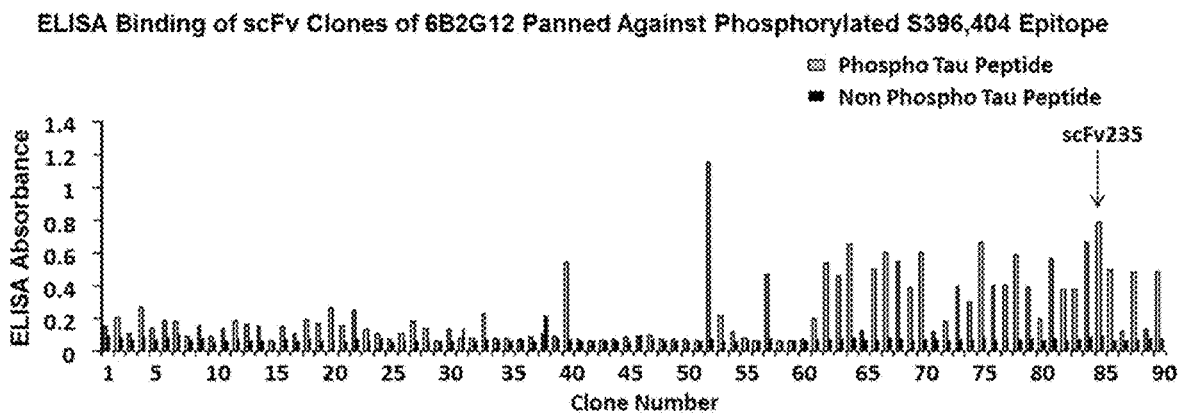
FIGS. 1A-1B show the binding of randomly selected scFv clones generated from antibody 6B2G12 (FIGS. 1A and 1B) to the non-phosphorylated epitope of SEQ ID NO:27 or the phosphorylated Tau epitope of SEQ ID NO:28. The clones of FIG. 1A were panned against the phosphorylated epitope (SEQ ID NO:28). The clones of FIG. 1B were panned against the non-phosphorylated epitope (SEQ ID NO:27).
Figure 1B:
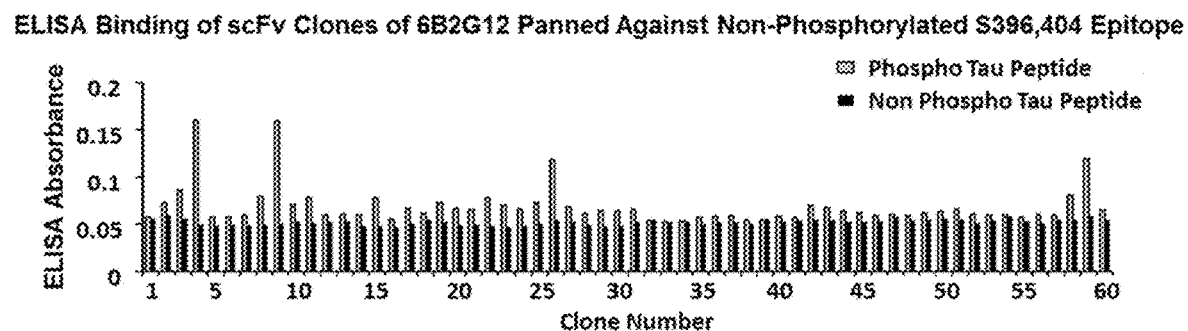

Tau-phospho-serine 396/404 (SEQ ID NO: 28):
RENAKAKTDHGAEIVYKSPVVSGDTSPRHL
``` wherein the underlined serine residues at positions 18 and 26 of SEQ ID NO:28 (corresponding to positions 396 and 404 of Tau (SEQ ID NO:1)) are phosphorylated. These peptides were also used for panning, ELISA and in Biacore for binding studies. Thousands of clones were generated, of which binding of randomly selected 90 clones is depicted in FIGS. 1A-1B. Among such selected scFv molecules was scFv235 (see FIG. 1A).

Production of Soluble Antibodies scFv were produced as described in Barbas, C. F., III et al. (2001) "*Phage Display: A Laboratory Manual*," Cold Spring Harbor Press, Cold spring Harbor, N.Y. Briefly, scFv235 was produced in competent non-suppressor *E. coli* cells (Top 10 cells, Invitrogen) in super broth (SB) medium (10 g MOPS, 30 g tryptone, 20 g yeast extract per liter) with 50 µg/ml of carbenicillin and 20 ml of 1M MgCl2 per liter. The culture was induced by adding 1 mM IPTG (isopropyl-β-D-thiogalactoside) and scFv235 was isolated from the pellet as described in Barbas, C. F., III et al. (2001).

Example 2

Characterization of scFv235

Figure 2D:
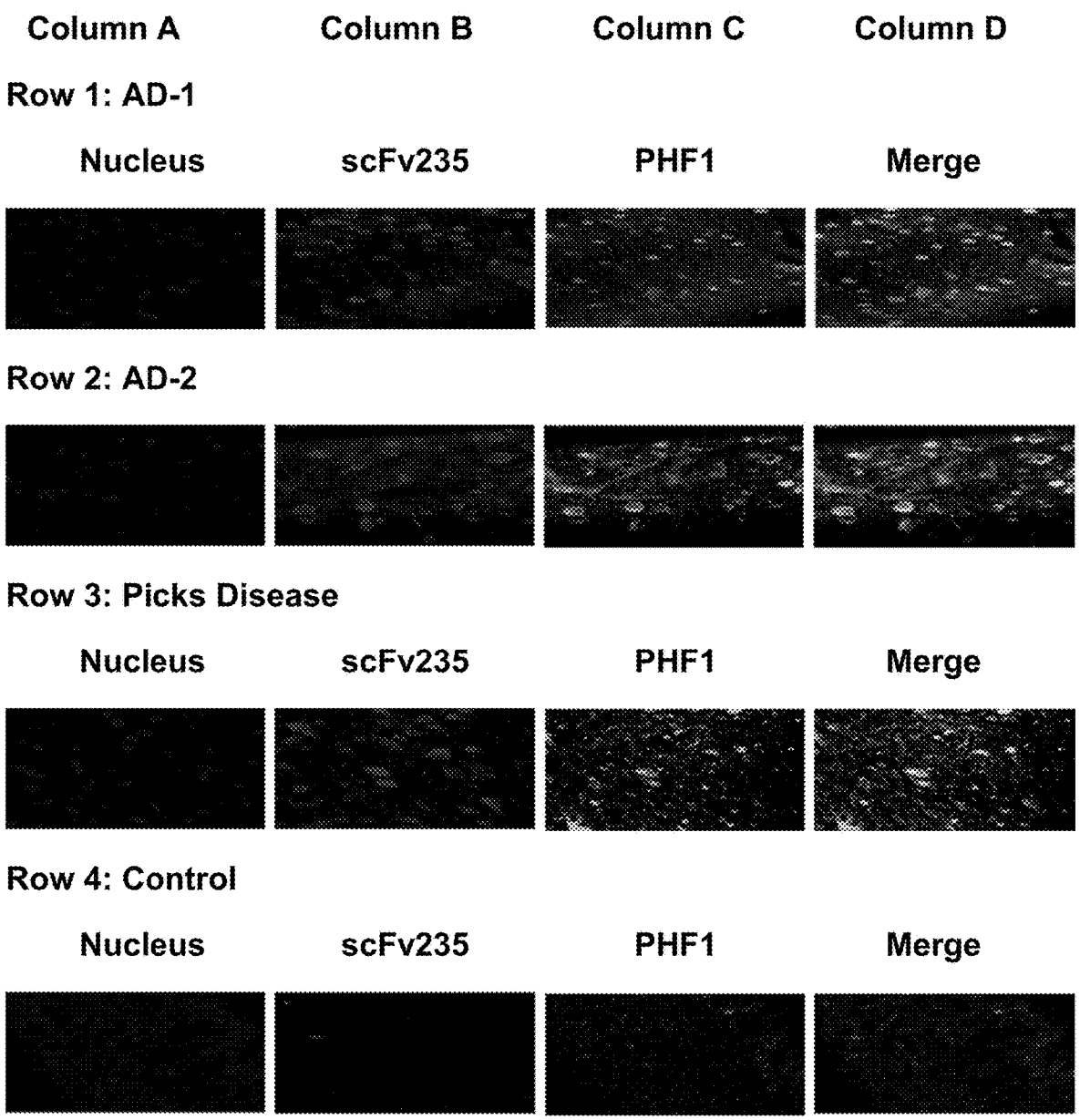
Figure 2E:
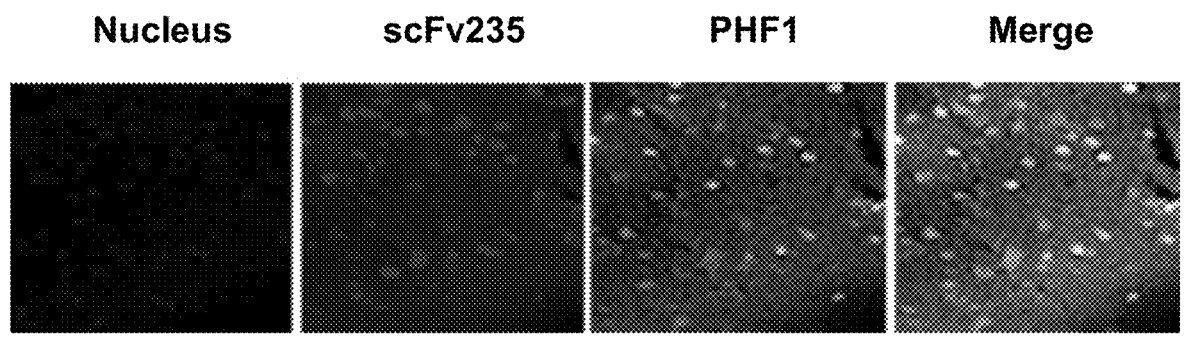
Figure 2E:
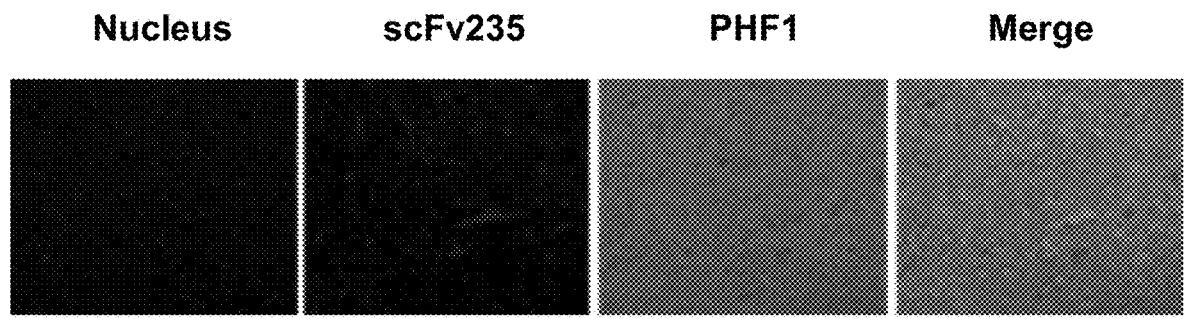

A single construct of those, scFv235 showed superior phospho-epitope specificity both when the peptide is coated on ELISA plates (FIG. 2A) as well as in Biacore when the molecule was immobilized and the binding peptides are in solution. Furthermore, scFv235 or its parent antibody, 6B2G12, immunoprecipitated Tau protein in brain homogenates of individuals who had Alzheimer's disease (FIGS. 2B-2C), and show partial co-localization staining with pathological Tau on fixed Alzheimer's and Pick's disease brain tissue (FIG. 2D-2E). Significantly, scFv235 detected only full length Tau protein bands, whereas 6B2G12 bound to both full length and degraded Tau fragments.

The His-tagged scFv235 was purified using Ni-NTA agarose resin loaded in a gravity column, following the Qiagen kit protocol. The antibody fragment was then dialyzed in PBS and used for further characterization. Phospho-

TABLE 5

| Analyte Peptides | $K_D$ Affinity (M) | |
| --- | --- | --- |
|  | 6B2G12 | scFv235 |
| Phospho-Tau-serine 396/404 | $3.95 \times 10^{-10}$ | $1.04 \times 10^{-6}$ |
| Tau-serine 396/404 | $2.51 \times 10^{-9}$ | $4.06 \times 10^{-3}$ |

The selectivity of scFv235 for the phosphorylated peptide (SEQ ID NO:28) relative to the non-phosphorylated peptide (SEQ ID NO:27) ($1/[1.04 \times 10^{-6}/4.06 \times 10^{-3}]$) is $3.9 \times 10^3$.

TABLE 6

| Analyte Peptides | Association (1/Ms) | | Dissociation (1/S) | | $K_D$ (M) | |
| --- | --- | --- | --- | --- | --- | --- |
|  | 6B2G12 | scFv235 | 6B2G12 | scFv235 | 6B2G12 | scFv235 |
| Phospho-Tau-serine 396/404 | $3.69 \times 10^6$ | $3.93 \times 10^3$ | $1.46 \times 10^{-3}$ | $3.9 \times 10^{-3}$ | $3.95 \times 10^{-10}$ | $9.94 \times 10^{-7}$ |
| Tau-serine 396/404 | $1.16 \times 10^6$ | 9.74 | $2.92 \times 10^{-3}$ | $3.96 \times 10^{-2}$ | $2.51 \times 10^{-9}$ | $4.06 \times 10^{-3}$ | selectivity of the purified scFv was first confirmed in an ELISA assay as described by Asuni, A. A. et al. (2007) "*Immunotherapy Targeting Pathological Tau Conformers In A Tangle Mouse Model Reduces Brain Pathology With Associated Functional Improvements*," J. Neurosci. 27:9115-9129, in which Tau-phospho-serine 396/404 and Tau-serine 396/404 peptides were coated onto the plate overnight at 4° C., and after blocking, incubated with 2.5 µg scFv235 for 2 h. HRP conjugated anti-HA secondary antibody was used to detect bound scFv235 at 450 nm.

Surface Plasmon Resonance (SPR) Analysis

The binding kinetics of scFv235's and its parent antibody, 6B2G12, to their target molecules were measured by SPR in a Biacore 2000 (GE Healthcare) according to the manufacturer's instructions and as described previously (Krishnaswamy, S. et al. (2009) "*Cloning Antifungal Single Chain Fragment Variable Antibodies By Phage Display And Competitive Panning Elution*," Anal. Biochem. 395:16-24; Krishnaswamy, S. et al. (2011) "*Isolation And Characterization Of Recombinant Single Chain Fragment Variable Anti-Idiotypic Antibody Specific To Aspergillus fumigatus Membrane Protein*," J. Immunol. Methods 366:60-68). Briefly, scFv235/antibody (10 µg/ml) was diluted in 10 mM sodium acetate, pH 5.0, and was immobilized on a separate CM5 sensor chip with an amine coupling kit (7 min contact time at 5 µl/min flow rate). Unreacted surface-bound material was blocked with ethanolamine. One channel of each sensor chip, prepared in the same way without scFv235 or antibody, was used to monitor the nonspecific binding of the peptide. All measurements were done with HBS-EP buffer (10 mM HEPES at pH 7.4, 150 mM NaCl, 3.4 mM EDTA and 0.005% surfactant P20) at flow rate of 5 µl/min at 25° C. After each measurement, the chip surface was regenerated with 10 µl of a buffer containing 500 mM NaCl and 0.1M glycine HCl, pH 8.0. Binding of Tau-phospho-serine 396/404 and Tau-serine 396/404 peptides was determined at various concentrations and the equilibrium dissociation constant (Kd) was calculated using BIAevaluation software with $Kd=k_{off}/k_{on}$. Table 5 and Table 6 summarize the kinetics and specificity of binding of the 6B2G12 antibody and scFv235.

scFv235 thus has an approximately 2,508 fold lower affinity for the phosphorylated P-Ser396/404 peptide than antibody 6B2G12 (i.e., for phospho-Tau-serine 396/404, the ratio of [6B2G12 Association/6B2G12 Dissociation] to [scFv235 Association/scFv235 Dissociation]=2,508), and an 1.62 million fold lower affinity for the non-phosphorylated P-Ser396/404 peptide than antibody 6B2G12 (i.e., for non-phosphorylated Tau 396/404, the ratio of [6B2G12 Association/6B2G12 Dissociation] to [scFv235 Association/scFv235 Dissociation]=1.62 million).

Antibody 6B2G12 thus has a $K_a$ for the non-phosphorylated peptide that is about 3 times lower than its $K_a$ for the phosphorylated peptide, and a $K_d$ for the non-phosphorylated peptide that is about double its $K_d$ for the phosphorylated peptide. In contrast, and unexpectedly, scFv235, which is derived from this antibody, exhibits a $K_a$ for the non-phosphorylated peptide that is about 400 times lower than its $K_a$ for the phosphorylated peptide, and a $K_d$ for the non-phosphorylated peptide that is about ten times lower than its $K_d$ for the phosphorylated peptide.

Immunoprecipitation

Dynabeads His-Tag Isolation and Dynabeads Protein G kits (Invitrogen) were used for immunoprecipitation of Tau in AD brain homogenate (250 µg) with scFv235 or antibody (10 µg), with the protocol as per the kit instructions. The pulled down proteins were separated on 10% acrylamide gels, followed by Western blotting. The proteins were transferred from the gels onto nitrocellulose membranes. The membranes were blocked with 5% skimmed milk in PBS for 1 h at room temperature. Then the blot was incubated with 1:1000 dilution of CP27 (human specific Tau antibody) or total Tau antibody (Dako), overnight at 4° C. This was followed by a 2 h incubation with HRP conjugated secondary antibody (1:1000) in PBS containing 5% skimmed milk. After washing, the proteins on the membrane were detected by enhanced chemiluminescence (ECL; Pierce). Images of immunoreactive bands were acquired using the Fuji LAS-4000 imaging system.

The scFv molecules specifically pulled down Tau bands in the range of 50-70 kDa, bound to pathological Tau in AD and Pick's disease brain sections, and had affinity on Biacore toward the phospho-epitope ($1.04 \times 10^{-6}$–$6.05 \times 10^{-8}$ M) and the non-phospho-epitope ($4.06 \times 10^{-3}$–$1.86 \times 10^{-8}$ M).

Human Brain Tissue Staining

The His-Tag purified scFv235 was labeled using ALEXA® FLUOR 568 protein labeling kit (Molecular Probes, Invitrogen) as per the kit instructions. Several AD, Pick's disease and age-matched control brains (National Disease Research Interchange) were stained with the 568-labeled scFv235 using standard procedures. Briefly, slide mounted paraffin embedded brain sections were deparaffinized in xylene and cleared through an ethanol gradient, washed in PBS, followed with epitope unmasking in 0.3% formic acid, and after PBS washes incubated with a mixture of 10 µg/ml of scFv235 and 1:1000 dilution of PHF1 Tau antibody culture supernatant overnight at 4° C. Bound PHF1 was detected with a fluorescently-tagged secondary antibody (Alexa Fluor 488 goat anti-mouse IgG, 1:500 dilution, Life Technologies). Nuclei were detected with DAPI and the slides coverslipped with ProLong Gold antifade reagent mounting media (Life Technologies). Images were captured on a Fluoview 1000 laser scanning confocal microscope (Olympus) using wavelength and filters according to the characteristics of the fluorophores.

Example 3

Animals, Injections of Labeled Antibodies and IVIS Imaging

In light of its superior characteristics, scFv235 was chosen for in vivo imaging in mice. Mice were housed in AAALAC-approved facilities and received food and water ad libitum. The experiments were performed under an IACUC-approved protocol. Three different transgenic tangle models were used: htau (Andorfer, C. et al. (2003) "*Hyperphosphorylation And Aggregation Of Tau In Mice Expressing Normal Human Tau Isoforms*," J. Neurochem. 86:582-590); htau/PS1 (Boutajangout, A. et al. (2010) "*Immunotherapy Targeting Pathological Tau Prevents Cognitive Decline In A New Tangle Mouse Model*," J. Neurosci. 30:16559-16566), and JNPL3 (Lewis, J. et al. (2000) "*Neurofibrillary Tangles, Amyotrophy And Progressive Motor Disturbance In Mice Expressing Mutant (P301L) Tau Protein*," Nat. Genet. 25:402-405). Controls were wild-type mice and transgenic Aβ plaque mice (Tg-SwDI (Davis, J. et al. (2004) "*Early-Onset And Robust Cerebral Microvascular Accumulation Of Amyloid Beta-Protein In Transgenic Mice Expressing Low Levels Of A Vasculotropic Dutch/Iowa Mutant Form Of Amyloid Beta-Protein Precursor*," J. Biol. Chem. 279:20296-20306).

Intracarotid injections were performed as described by Asuni, A. A. et al. (2007) "*Immunotherapy Targeting Pathological Tau Conformers In A Tangle Mouse Model Reduces Brain Pathology With Associated Functional Improvements*," J. Neurosci. 27, 9115-9129. Briefly, mice were anesthetized with 2% isoflurane and maintained with 1.5% isoflurane in 30% O2. After exposing the carotid sheath, left common carotid artery (CCA), external carotid artery (ECA), and internal carotid artery (ICA) were exposed via a midline incision. A silk suture was tied to the distal end of the ECA, and the left CCA, ICA, and pterygopalatine artery were temporarily tied. A 30 gauge needle connected to PE-10 tubing (Becton Dickinson, San Diego, Calif.) was attached to a 1 ml syringe and 250 µg of labeled scFv235 in 400-500 µl PBS was then administered into the common carotid artery over a period of 10-15 min. KRAZY® glue was applied to the site of injection to prevent postoperative bleeding. Alternatively, mice were injected into the femoral vein using the same dose. The medial side of the right thigh was shaved and cleaned with Betadine solution and 70% ethanol. A small incision (0.5 cm) parallel to the vein was made on the skin of the internal side of the thigh. When the buttonhole of skin opens, the femoral vein is visible. A 30 gauge needle connected to PE-10 tubing was attached to a 1 ml syringe, administered through the needle punctured upward into the femoral vein over a period of 3-5 min manually. Once the needle was removed, the site of the puncture was compressed with a cotton-tipped applicator, in order to avoid bleeding. As soon as the blood flow had ceased, the skin was sutured with 4/0 braided silk thread using single interrupted sutures. For IVIS imaging, scFv235 or 6B2G12 was conjugated with VIVOTAG 680 XL FLUOROCHROME™ (Perkin Elmer). The mice were shaved on the head and body to avoid light diffraction caused by the fur. After injection, mice were subjected to imaging, at various intervals as detailed in FIGS. 3A-3D, in IVIS Lumina XR (Perkin Elmer) using an excitation filter of 675 nm and Cy5.5 emission filter.

Intracarotid injection with scFv235 tagged with a fluorophore led to a partial (Tau-5) to complete co-localization (PHF-1) with stained intraneuronal Tau aggregates within the brain in transgenic tauopathy mice (n=6) but not in wt mice (n=4). Furthermore, the scFv co-localized with markers of endosomes-autophagosomes-lysosomes, which are known to contain Tau aggregates, suggesting that this interaction takes place in these degradation pathways. Preliminary findings from IVIS imaging in live mice show a substantially stronger signal from the right hemisphere in transgenic compared to wild-type mice when imaged about 30 min after right intracarotid injection. This signal gradually diminishes and spreads from the brain to the periphery over several hours.

Analysis of IVIS Images

Images were analyzed using the Living Imaging software from Perkin Elmer as per online protocol. Total Radiant Efficiency (summed signal intensity) was calculated in the outlined region of interest (brain). Total Radiant Efficiency was calculated as:

$$\text{Total Radiant Efficiency} = \frac{p/\sec/cm^2/sr}{\mu W/cm^2}$$

Immunohistochemistry of Mouse Brain Sections

After imaging, the tissue was processed as described by Asuni, A. A. et al. (2007) "*Immunotherapy Targeting Pathological Tau Conformers In A Tangle Mouse Model Reduces Brain Pathology With Associated Functional Improvements*," J. Neurosci. 27, 9115-9129. Briefly, the mice were perfused transaortically with PBS, the brains removed and fixed in 2% PLP overnight, placed in 2% DMSO in 20% glycerol phosphate buffer overnight, then sectioned to detect 680XL-scFv235 signal and to determine scFv subcellular location by co-staining with marker of Tau protein and the endosomal/autophagosomal/lysosomal system. Serial coronal 40 µm sections of the brain were prepared and immunofluorescence staining was performed per standard protocol on free floating sections. Briefly, after PBS washes, 0.3% Triton-X-100 permeabilization, and block in 5% BSA, tissue was incubated with antibodies (1:500-1:1000) overnight at 4° C. [Tau (Taus, MC1, PHF1), microglia (Iba1), early endosomes (EEA1), late endosomes (rab7), late endosomes/lysosomes (lamp2, P62), and autophagosomes (LC3 and P62). Bound antibodies were detected with an Alexa Fluor 488 goat anti-mouse/rabbit IgG (Invitrogen), and nuclei with DAPI. After coverslipping with ProLong Gold, the tissue was analyzed with an LSM 700 Zeiss confocal laser scanning microscope. The extent of staining with each label and their co-localization was rated using a semi-quantitative scale of 0-4 4 with 1-4 indicating increasing degree of these parameters (1: minimal; 2: modest; 3: moderate; 4: extensive). Such analysis was performed for: 1) residual signal of the injected fluorescently-tagged scFv/antibody; 2) degree of brain Tau pathology; 3-4) extent of co-localization of injected scFv/antibody signal with 3) Tau antibody staining or 4) endosome/lysosome/autophagosome antibody staining.

Statistics

Correlation analysis between the different parameters described in FIGS. 6A-6F was analyzed by Spearman rank correlation. When scFv235 or antibody brain tissue signal was one parameter, only mouse brains removed within few hours after injection were included, as the brain tissue signal weakens over time. For correlations between IVIS signal and Tau pathology, all the injected mice were included.

Imaging Analysis

Imaging studies using In vivo Imaging System ("IVIS") revealed strong brain signals from transgenic ("tg") tauopathy mice when near-infrared-dye-labeled-scFv235 was injected into the right carotid artery (250 µg/450-500 µl). The signal remained high and relatively stable for at least up to 250-300 min (FIGS. 3A-3D). JNPL3 mice (Lewis, J. et al. (2000) "*Neurofibrillary Tangles, Amyotrophy And Progressive Motor Disturbance In Mice Expressing Mutant (P301L) Tau Protein*," Nat. Genet. 25:402-405), with the P301L Tau mutation, showed stronger signal than htau/PS1 mice (Boutajangout, A. et al. (2010) "*Immunotherapy Targeting Pathological Tau Prevents Cognitive Decline In A New Tangle Mouse Model*," J. Neurosci. 30:16559-16566), which have milder overall Tau pathology. Brain signal from scFv235 injected P301L mice peaked at 35-38 min (1714% above pre-injection baseline signal), and remained strong at 82 and 330 minutes post-injection (1675% and 1468%, respectively). In the htau/PS1 mice, the scFv235 brain signal peaked at 37 minutes (1443% above pre-injection baseline signal), and remained strong at 65 and 176 minutes post-injection (1144% and 1093%, respectively). The htau/PS1 model had less signal than P301L mice, both in brain and periphery. Older mice within each genotype had stronger signal than younger mice which is as expected since those should have more advanced Tau pathology. Minimal signal was observed in wild-type (wt) mice injected with the same probe or in tangle mice that received only the fluorescent dye alone without the scFv. The antibody from which the scFv was derived, 6B2G12, provided similar results when injected at the same dose and via the same route, albeit its signal intensity was substantially less. Imaging at 20-95 minutes post-injection showed a signal of 600-632% above baseline value with a modest reduction at the depicted 170 and 291 minutes (497% and 431%, respectively). Older (11-12 months) P301L mice injected with scFv235 had peak brain signal [total radiant efficiency (TRE)] of $2.23 \times 10^{11}$ and $2.64 \times 10^{11}$ respectively, whereas the younger mice (3 and 8 months) had lower peak signals of $1.88 \times 10^{11}$ and $1.86 \times 10^{11}$, respectively. The same P301L model (7-10 months) had strong but lesser brain signal after 6B2G12 injection, ranging from $2.20 \times 10^{1}1$ to $1.16 \times 10^{11}$. Similar signal intensity was observed in an old scFv235-injected htau/PS1 mouse (22 months; peak at $1.40 \times 10^{11}$) but limited in a 7 months old htau/PS1 mouse, which was confirmed to lack Tau pathology. Wt mice (12-13 months) and one htau mouse (13 months) had low signal at all time points and had no Tau pathology. Injection of the fluorescent-tag alone in an old htau/PS1 mouse (23 months) and a P301L mouse (7 months) gave a higher brain signal than in wt mice, injected with scFv235 or 6B2G12, but it was substantially less than in any of the tauopathy mice injected with the scFv or antibody. These two dye injected mice were confirmed to have extensive Tau pathology.

The brains were subsequently removed for further analyses to verify the presence and subcellular location of the scFv or antibody in the brain (FIGS. 4A-4D). Both were detected primarily in neurons, partially co-localized with pathological Tau proteins and exclusively in the endosome-autophagosome-lysosome system. A smaller portion was detected in microglia. Transgenic mice with limited Tau pathology, because of young age, model differences or intra-model variability, had a weak IVIS brain signal after the diagnostic ligand injection.

The inventors also assessed the feasibility of using the intravenous (i.v.) route, which would be more useful applicable for multiple injections and for clinical use. Importantly, strong brain signals were also observed for both ligands when this route of administration was used, at the same dose, indicating that even with first pass liver clearance sufficient amount of the ligand entered the brain to allow us to clearly detect Tau lesions. Longer imaging sessions were conducted in the i.v. injected mice, showing a gradual clearance of the signal over 8-14 days (FIG. 3C-3D). As for the intracutaneous (i.c.) injection, mice injected with the scFv showed generally stronger signal than mice injected with the Tau antibody. In i.v. injected P301L mice, peak scFv235 brain signal was detected at 18 min (1754% above pre-injection baseline), with lesser signal at 210 min (18% reduction from peak signal), that had substantially subsided at 8 days (43% reduction). In 6B2G12 antibody injected mice, brain signal was strong at 25 minutes (1211% above pre-injection baseline), peaked at 35 minutes (1445%), with lesser signal at 120 minutes (11% reduction from peak signal) and was much weaker by 8 and 12 days (67% and 70% reduction, respectively). P301L mice injected with control pooled IgG had a modest IVIS signal despite having very extensive Tau pathology, and the brain signal did not co-localize with Tau markers. This is consistent with the inventors' prior tissue findings in P301L mice following intracarotid injection of control IgG (Asuni, A. A. et al. (2007) "*Immunotherapy Targeting Pathological Tau Conformers In A Tangle Mouse Model Reduces Brain Pathology With Associated Functional Improvements*," J. Neurosci. 27:9115-9129). Wild-type (Wt) or mice with Aβ plaques (Tg-SwDI, (Davis, J. et al. (2004) "*Early-Onset And Robust Cerebral Microvascular Accumulation Of Amyloid Beta-Protein In Transgenic Mice Expressing Low Levels Of A Vasculotropic Dutch/Iowa Mutant Form Of Amyloid Beta-Protein Precursor*," J. Biol. Chem. 279:20296-20306) had minimal brain signal at all time points, highlighting the specificity of the probes for Tau pathology. As with the i.c. injection, the scFv or Tau antibody co-localized with pathological Tau and the probes were detected in the endosome-autophagosome-lysosome system within neurons (FIGS. 3A-3D, FIGS. 4A-4D), and to some extent in microglia.

scFv235 was found to co-localize with pathological Tau within brain neurons following intracarotid injection in P301L (F6) and htau/PS1 (A47) tangle mice (FIG. 5). Brains were harvested after the last imaging session. Tau aggregates were detected with PHF-1 and Tau-5 antibodies, and show partial co-localization with scFv235. A nuclear-specific stain was used to identify the cell nuclei. FIG. 5 also shows that control wild-type mice (R1) did not have detectable brain uptake of scFv235 after intracarotid injection. Tau-5 stained mainly normal axonal Tau and pathological PHF1 staining was not observed.

In sum, a comparison of the degree of the IVIS signal, residual scFv or antibody signal from sectioned brains and the extent of Tau pathology, after both routes of administration, revealed excellent correlation between these parameters (FIGS. 4A-4D, Table 7, Table 8 (Parts A-C), FIG. 5 and FIGS. 6A-6F), scFv: IVIS signal vs. brain tissue scFv signal, $r=0.93$, $p<0.0006$; IVIS signal vs. brain Tau pathology, $r=0.86$, $p<0.0002$; brain tissue scFv signal vs. brain Tau pathology, $r=0.87$, $p<0.01$; 6B2G12: IVIS signal vs. brain tissue 6B2G12 signal, $r=0.87$, $p=0.1$; IVIS signal vs. brain Tau pathology, $r=0.9$, $p<0.0004$; brain tissue 6B2G12 signal vs. brain Tau pathology, $r=0.8$, $p=0.05$. These findings indicate that this particular scFv, the parental antibody, and the overall approach worked very well to detect and assess the degree of Tau pathology in live animals.

TABLE 7

Overview of IVIS Imaging Studies of Mice That Received Intracarotid or Intravenous Injection with Diagnostic Probes scFv235 or 6B2G12 Antibody

| Injection Route and Probe | Mice | Results | |
|---|---|---|---|
| Objective: | Uptake Of scFV235 In The Brain And Binding To Pathological Tau Within Neurons | | |
| Conjugated Dye: | Alexa Fluor 568 | | |
| Intracarotid - scFv235 | 3 htau/PS1 | Good scFv signal that co- localizes well with Tau5 and MCI antibody. | |
| Intracarotid - scFv235 | 2 WT | Limited scFv signal | |
| Objective: | Live IVIS imaging for scFv235/6B2G12 | | |
| Conjugated Dye: | VIVOTAG 680 XL FLUOROCHROME ™ | | |

| | | IVIS Signals | Staining Signal |
|---|---|---|---|
| Intracarotid - scFv235 | 3 htau/PS1 | Imaging not performed for B32 mouse | Strong scFv signal that co-localizes well with Tau aggregates and endosome/autophagosome/lysosome (e/a/l) markers for B32 mouse |
| | | Weak signal for BB5 mouse | Weak scFv signal and no Tau pathology for BB5 mouse |
| | | Strong signal in the right hemisphere that slowly decreases up to 4 h for A47 mouse | Strong scFv signal that co-localizes well with Tau aggregates and e/a/l markers for A47 mouse |
| Intracarotid - scFv235 | 4 P301L | Strong scFv signal that is sustained even after 5 h | Strong scFv signal that co-localizes well with Tau aggregates and e/a/i markers |
| Intracarotid - scFv235 | 2 WT and 1 htau | Weak signal | Weak scFv signal. Limited (htau) or no (wt) Tau pathology |
| Intracarotid - Free Dye | 2 P301L | Modest signal | Weak signal that does not co-localize with Tau aggregates |
| Intracarotid - 6B2G12 | 3 P301L | Strong signal that slowly decreases the next 3-5 h | Strong 6B2G12 signal that co-localizes well with Tau aggregates and e/a/l markers |
| Intracarotid - 6B2G12 | 3 WT | Weak signal | Weak 6B2G12 signal: No Tau pathology |
| Intravenous - scFv235 | 3 P301L | Strong signal up to 1 h that slowly decreases the next 3 h | Weak scFv signal after 7-31 days that co-localizes well with Tau aggregates and e/a/l markers |
| Intravenous - scFv235 | 1 TgSwDl, 1 WT | Weak Signal | Weak scFv and Tau antibody signals |
| Intravenous - 6B2G12 | 3 P301L | Strong signal up to 1 h that slowly decreases the next 3 h | Weak signal after 7-31 days that co-localizes well with Tau aggregates and e/a/l markers |
| Intravenous - 6B2G12 | 1 Tg-SwDI, 1 WT | Weak signal | Weak 6B2G12 signal. No Tau pathology |
| Intravenous - Control IgG | 2 P301L | Modest signal | Weak control IgG signal. Extensive Tau pathology, but control IgG does not co-localize with Tau aggregates |

TABLE 8

(Part A)
IVIS Signal (Maximum Total Radiant Efficiency) And Semi-Quantitative Assessment Of Probe Signal From The Brain Sections, Tau Pathology And Co-Localization Of The Injected Probe With Various Markers Of The Tau Protein And The Endosome-Autophagosome-Lysosome System

| Mice ID | Strain | Age (Months) | Injected Material/Route Intracarotid (IC) Intravenous (IV) | IVIS-Maximum Total Radiant Efficiency | Brain Removal After Injection |
|---|---|---|---|---|---|
| BB8 | P301L | 8 | IC-scFv235 | 1.86E+11 | 180 minutes |
| A12 | P301L | 12 | IC-scFv235 | 2.64E+11 | 330 minutes |
| A13 | P301L | 11 | IC-scFv235 | 2.23E+11 | 252 minutes |
| F6 | P301L | 3 | IC-scFv235 | 1.88E+11 | 280 minutes |
| A50 | P301L | 9 | IC-6B2G12 | 1.16E+11 | 291 minutes |
| A52 | P301L | 9 | IC-6B2G12 | 1.23E+11 | 235 minutes |
| C1 | P301L | 7 | IC-6B2G12 | 2.20E+11 | Day 7 |
| B32 | htau/PS1 | 23 | IC-scFv235 | — | 120 minutes |
| A47 | htau/PS1 | 22 | IC-scFv235 | 1.40E+11 | 200 minutes |
| BB5 | htau/PS1 | 7 | IC-scFv235 | 2.56E+10 | 200 minutes |
| R1 | WT | 11 | IC-scFv235 | 4.36E+10 | 125 minutes |
| 4 | WT | 8 | IC-scFv235 | 1.34E+10 | 265 minutes |
| N32 | htau | 11 | IC-scFv235 | 3.87E+10 | Day 7 |
| A56 | htau/PS1 | 23 | IC-680 Dye | 7.45E+10 | 122 minutes |
| D24 | P301L | 7 | IC-680 Dye | 6.56E+10 | 165 minutes |
| 1 | WT | 8 | IC-6B2G12 | 1.22E+10 | 290 minutes |
| 2 | WT | 8 | IC-6B2G12 | 1.48E+10 | 225 minutes |
| 3 | WT | 8 | IC-6B2G12 | 1.21E+10 | 180 minutes |
| A55 | P301L | 9 | IV-scFv235 | 2.07E+11 | Day 7 |
| B11 | P301L | 13 | IV-scFv235 | 2.28E+11 | Day 31 |
| E19 | P301L | 8 | IV-scFv235 | 1.13E+11 | Day 7 |
| A49 | P301L | 11 | IV-6B2G12 | 1.48E+11 | Day 12 |
| C2 | P301L | 7 | IV-6B2G12 | 1.85E+11 | Day 12 |
| B15 | P301L | 13 | IV-6B2G12 | 7.62E+10 | Day 31 |
| VN139 | Tg-SwDI | 12 | IV-scFv235 | 1.58E+10 | Day 31 |
| 6 | WT | 8 | IV-scFv235 | 1.11E+10 | Day 7 |
| VN142A | Tg-SwDI | 12 | IV-6B2G12 | 1.49E+10 | Day 31 |
| 7 | WT | 8 | IV-6B2G12 | 8.95E+09 | Day 7 |
| D13 | P301L | 13 | IV-Control IgG | 8.94E+10 | Day 16 |
| D15 | P301L | 13 | IV-Control IgG | 9.03E+10 | Day 16 |

(Part B)
IVIS Signal (Maximum Total Radiant Efficiency) And Semi-Quantitative Assessment Of Probe Signal From The Brain Sections, Tau Pathology And Co-Localization Of The Injected Probe With Various Markers Of The Tau Protein And The Endosome-Autophagosome-Lysosome System

| Mice ID | Brain Signal In Sections | Brain Tau Pathology | Co-Localization With Tau Markers | | |
|---|---|---|---|---|---|
| | | | Tau5 | MC1 | PHF1 |
| BB8 | +++ | +++ | +++ | +++ | +++ |
| A12 | ++++ | ++++ | +++ | +++ | +++ |
| A13 | ++++ | +++ | +++ | +++ | +++ |
| F6 | +++ | ++ | +++ | +++ | +++ |
| A50 | +++ | +++ | +++ | +++ | ++ |
| A52 | +++ | +++ | +++ | +++ | +++ |
| C1 | ++ | ++++ | +++ | +++ | +++ |
| B32 | +++ | +++ | +++ | +++ | +++ |
| A47 | +++ | +++ | +++ | +++ | +++ |
| BB5 | + | 0 | 0 | 0 | 0 |
| R1 | + | 0 | 0 | 0 | 0 |
| 4 | + | 0 | 0 | 0 | 0 |
| N32 | + | 0 | + | 0 | + |
| A56 | + | ++ | 0 | 0 | 0 |
| D24 | ++ | +++ | 0 | 0 | 0 |
| 1 | + | 0 | 0 | 0 | 0 |
| 2 | + | 0 | 0 | 0 | 0 |
| 3 | + | 0 | 0 | 0 | 0 |
| A55 | ++ | +++ | ++++ | ++++ | +++ |
| B11 | + | +++ | ++++ | ++++ | +++ |
| E19 | + | +++ | ++++ | ++++ | +++ |
| A49 | ++ | +++ | ++++ | ++++ | ++ |
| C2 | ++ | +++ | ++++ | ++++ | ++ |
| B15 | + | +++ | ++++ | ++++ | ++ |
| VN139 | 0 | 0 | 0 | 0 | 0 |
| 6 | + | 0 | 0 | 0 | 0 |
| VN142A | 0 | 0 | 0 | 0 | 0 |
| 7 | + | 0 | 0 | 0 | 0 |

TABLE 8-continued

| D13 | + | ++++ | 0 | 0 | 0 |
| D15 | + | ++++ | 0 | 0 | 0 |

(Part C)
IVIS Signal (Maximum Total Radiant Efficiency) And Semi-Quantitative Assessment Of Probe Signal From The Brain Sections, Tau Pathology And Co-Localization Of The Injected Probe With Various Markers Of The Tau Protein And The Endosome-Autophagosome-Lysosome System

| Mice ID | Co-Localization With Endosome/Lysozyme/Autophagy Markers | | | |
|---|---|---|---|---|
| | EEA1 | Rab7 | LC3 | P62 |
| BB8 | +++ | +++ | +++ | +++ |
| A12 | +++ | +++ | +++ | +++ |
| A13 | +++ | +++ | ++++ | +++ |
| F6 | +++ | +++ | ++++ | +++ |
| A50 | +++ | +++ | +++ | +++ |
| A52 | +++ | +++ | +++ | +++ |
| C1 | +++ | +++ | +++ | +++ |
| B32 | +++ | +++ | ++++ | +++ |
| A47 | +++ | +++ | ++++ | +++ |
| BB5 | 0 | 0 | 0 | 0 |
| R1 | 0 | 0 | 0 | 0 |
| 4 | 0 | 0 | 0 | 0 |
| N32 | + | 0 | 0 | 0 |
| A56 | 0 | 0 | 0 | 0 |
| D24 | 0 | 0 | 0 | 0 |
| 1 | 0 | 0 | 0 | 0 |
| 2 | 0 | 0 | 0 | 0 |
| 3 | 0 | 0 | 0 | 0 |
| A55 | +++ | +++ | +++ | +++ |
| B11 | +++ | +++ | +++ | +++ |
| E19 | +++ | +++ | +++ | +++ |
| A49 | +++ | +++ | +++ | +++ |
| C2 | +++ | +++ | +++ | +++ |
| B15 | +++ | +++ | +++ | +++ |
| VN139 | 0 | 0 | 0 | 0 |
| 6 | 0 | 0 | 0 | 0 |
| VN142A | 0 | 0 | 0 | 0 |
| 7 | 0 | 0 | 0 | 0 |
| D13 | – | – | – | – |
| D15 | – | – | – | – |

Thus, in summary, scFv molecules of a monoclonal Tau antibody were generated using phage display technology. Following extensive characterization, scFv235 was assessed as a diagnostic imaging probe in live tauopathy mice. scFv235 consistently showed strong brain signal after peripheral injection in two tauopathy tangle mouse models but not in wild-type or Aβ plaque mice. Administration of the parent antibody led to similar results, but at a lesser signal intensity. Both probes co-localized with intraneuronal Tau aggregates and markers of the endosome/autophagosome/lysosome pathways.

The data show that Tau antibodies and their derivatives administered peripherally can be used to image Tau brain lesions in live animals. Importantly, the brain signal intensity correlated very well with the extent of the Tau pathology with major implications for experimental and clinical use of this approach. It can be used in this form for non-invasive monitoring of Tau pathology and treatment efficacy in animal models of tauopathy, and such ligands have great potential as clinical PET ligands for the same purpose.

The excellent correlation between the IVIS signal, residual probe signal in the brain tissue and the Tau pathology confirms that this approach is useful for the diagnosis of Alzheimer's disease and other tauopathy in humans and related animal models and that it provides a means for monitoring treatment efficacy in such patients and related animal models.

The scFv molecule or its parent antibody were detected primarily in neurons, co-localized with pathological Tau proteins in the endosome-autophagosome-lysosome system. This is consistent with the similar distribution of labeled Tau antibodies and their Fab fragments that is observed after the intracarotid injection or administration of such molecules to brain slice cultures derived from tauopathy mice (Gu, J. et al. (2013) "Two Novel Tau Antibodies Targeting The 396/404 Region Are Primarily Taken Up By Neurons And Reduce Tau Protein Pathology," J. Biol Chem. 288:33081-33095; Congdon, E. E. et al. (2013) "Antibody Uptake into Neurons Occurs Primarily via Clathrin-dependent Fcgamma Receptor Endocytosis and Is a Prerequisite for Acute Tau Protein Clearance," J. Biol Chem. 288:35452-35465; Asuni, A. A. et al. (2007) "Immunotherapy Targeting Pathological Tau Conformers In A Tangle Mouse Model Reduces Brain Pathology With Associated Functional Improvements," J. Neurosci. 27: 9115-9129; Krishnamurthy, P. K. et al. (2011) "Mechanistic Studies Of Antibody Mediated Clearance Of Tau Aggregates Using An Ex Vivo Brain Slice Model," Front. Psychiatry 2:59). However, this is the first report detecting such aggregates in vivo using antibodies or their fragments as imaging agents. Prior preclinical and clinical studies targeting Aβ, α-synuclein or the Tau protein demonstrate that antibodies have substantial access into brains with aggregates of these peptides/proteins, presumably because of associated inflammation that leads to opening of the blood-brain barrier (Congdon. E. E. et al. (2014) *"Harnessing The Immune System For Treatment And Detection Of Tau Pathology,"* J. Alzheimers. Dis. 40:S113-S121; Lemere, C. A. et al. (2010) *"Can Alzheimer Disease Be Prevented By Amyloid-Beta Immunotherapy?,"* Nat. Rev. Neurol. 6:108-119).

There are several possible explanations for the lower signal of the antibody compared to the scFv. The antibody is about 6 times the size of the scFv (150 kDa vs. 25 kDa) which may result in less brain and neuronal uptake. The injections are both of the same weight (250 µg), and thus contain 6 times fewer molecules of the antibody compared to the fragment. This initial dose was chosen based on a previous study of brain uptake of tagged polyclonal anti-Tau mouse IgG (Asuni, A. A. et al. (2007) *"Immunotherapy Targeting Pathological Tau Conformers In A Tangle Mouse Model Reduces Brain Pathology With Associated Functional Improvements,"* J. Neurosci. 27:9115-9129). The higher affinity of the antibody for Tau, compared to the scFv may counteract these issues.

The weak IVIS brain signal in Tg mice with limited Tau pathology, further supports the conclusion that the enhanced signal in the Tg mice is not a mere reflection of Tau overexpression but rather indicates the presence of Tau pathology. JNPL3 (P301L) mice exhibit stronger brain and peripheral signal than htau/PS1 mice. Within the brain, this fits with more severe Tau pathology. The greater peripheral signal observed in P301L mice appears in part to be derived from the spinal cord which is known to have extensive Tau lesions in this model (Lewis, J. et al. *"Neurofibrillary Tangles, Amyotrophy And Progressive Motor Disturbance In Mice Expressing Mutant (P301L) Tau Protein,"* Nat. Genet. 25, 402-405). Also, the prion promoter of its mutated Tau transgene results in more global Tau expression than in the htau/PS1 model. This may lead to Tau aggregation in various organs.

For animal studies, IVIS imaging is more cost-effective than positron emission tomography (PET) studies and involves a much simpler probe preparation; its labeling with a near infrared dye instead of more complicated radiolabeling procedure, which may require an on-site cyclotron. Hence, IVIS imaging is ideal for probe development to select ligands for subsequent PET studies. Such studies further indicate that it is an efficient way to monitor the development of Tau pathology and to screen for Tau therapy-mediated clearance of Tau aggregates, with each animal serving as its own control during longitudinal studies.

The findings strongly support the ability and use of Tau antibodies and/or their scFv molecules to detect Tau lesions in vivo. In contrast to β-sheet binding dyes, Tau s antibody-derived probes (e.g., scFv235) targeting different epitopes are believed to provide more detailed picture of the pathological profile of Tau proteins in each individual. This information is envisaged to be able to guide the treatment regimen, which may include active or passive Tau immunotherapy targeting the same Tau epitopes that were detected with imaging. Such a tailored approach is likely to be more efficacious to slow the progression of the tauopathy that is being targeted (see, e.g., Gu, J. et al. (2013) *"Two Novel Tau Antibodies Targeting The 396/404 Region Are Primarily Taken Up By Neurons And Reduce Tau Protein Pathology,"* J. Biol. Chem. 288:33081-33095; Congdon, E. E. et al. (2013) *"Antibody Uptake into Neurons Occurs Primarily via Clathrin-dependent Fcgamma Receptor Endocytosis and Is a Prerequisite for Acute Tau Protein Clearance,"* J. Biol Chem. 288:35452-35465; Boutajangout, A. et al. (2010) "Immunotherapy Targeting Pathological Tau Prevents Cognitive Decline In A New Tangle Mouse Model," J. Neurosci. 30:16559-16566; Asuni, A. A. et al. (2007) *"Immunotherapy Targeting Pathological Tau Conformers In A Tangle Mouse Model Reduces Brain Pathology With Associated Functional Improvements,"* J. Neurosci. 27:9115-9129; Boutajangout, A. et al. (2011) *"Passive Immunization Targeting Pathological Phospho-Tau Protein In A Mouse Model Reduces Functional Decline And Clears Tau Aggregates From The Brain,"* J. Neurochem. 118:658-667; Boimel, M. et al. (2010) *"Efficacy And Safety Of Immunization With Phosphorylated Tau Against Neurofibrillary Tangles In Mice,"* Exp. Neurol. 224, 472-485 (2010); Chai, X. et al. (2011) *"Passive Immunization With Anti-Tau Antibodies In Two Transgenic Models: Reduction Of Tau Pathology And Delay Of Disease Progression,"* J. Biol Chem. 286:34457-34467 (2011); Bi, A. et al. (2011) *"Tau-Targeted Immunization Impedes Progression of Neurofibrillary Histopathology in Aged P301L Tau Transgenic Mice,"* PLoS. One. 6:e26860; d'Abramo, C. et al. (2013) *"Tau Passive Immunotherapy in Mutant P301L Mice: Antibody Affinity versus Specificity,"* PLoS ONE 8:e62402; Troquier, L. et al. (2012) *"Targeting Phospho-Ser422 By Active Tau Immunotherapy In The THY-Tau22 Mouse Model: A Suitable Therapeutic Approach,"* Curr. Alzheimer Res. 9, 397-405; Kfoury, N. et al. (2012) *"Trans-cellular Propagation of Tau Aggregation by Fibrillar Species,"* J. Biol. Chem. 287:19440-19451; Theunis, C. et al. (2013) *"Efficacy And Safety Of A Liposome-Based Vaccine Against Protein Tau, Assessed In Tau.P 301L Mice That Model Tauopathy,"* PLoS. One. 8:e72301: Yanamandra, K. et al. (2013) *"Anti-Tau Antibodies That Block Tau Aggregate Seeding In Vitro Markedly Decrease Pathology And Improve Cognition in vivo,"* Neuron 80:402-414; Castillo-Carranza, D. L. et al. (2014) *"Specific Targeting Of Tau Oligomers In Htau Mice Prevents Cognitive Impairment And Tau Toxicity Following Injection With Brain-Derived Tau Oligomeric Seeds,"* J. Alzheimers. Dis. 40:S97-S111; Castillo-Carranza, D. L. et al. (2014) *"Passive Immunization with Tau Oligomer Monoclonal Antibody Reverses Tauopathy Phenotypes without Affecting Hyperphosphorylated Neurofibrillary Tangles,"* J. Neurosci. 34:4260-4272). The availability of selective biomarkers to determine target engagement, clearance and disease progression will be essential to avoid the lengthy, expensive and inconclusive studies in previous Alzheimer' s clinical immunotherapy trials. Imaging of these Tau lesions will be very helpful to evaluate the efficacy of future trials as well as to diagnose Aβ negative tauopathies.

Example 4

Specific and Epitope Dependent Detection of Tau Aggregates in Transgenic Tauopathy Mice In Vivo As indicated above, the peripheral injection of a single-chain variable antibody fragment (scFv) generated from antibody 6B2G12 resulted in a strong in vivo brain signal in transgenic tauopathy mice using an In Vivo Imaging System (IVIS) but not in wild-type or amyloid-βplaque mice (Krishnaswamy S. et al. (2014) *"Antibody-Derived In Vivo Imaging of Tau Pathology,"* J. Neurosci. 34:16835-16850; hereby incorporated by reference herein). Similar specificity but a weaker signal was observed with the parent 6B2G12 antibody. Importantly, the intensity of the imaging signal correlated well with the degree of tau pathology and the co-localization of the probe with intraneuronal tau aggregates. Both attributes were associated with markers of endosomes, autophagosomes and lysosomes, indicating their interaction in these degradation pathways.

A comparison of the signal intensity of various tau antibodies against different tau epitopes in the same transgenic tauopathy mice (P301L, htau) was conducted by administering single intravenous injections of different tau antibodies. Two different doses were compared (50 µg vs. 250 µg) sometimes in the same animals. Injections were separated by at least a week interval in order to allow the brain signal to subside to baseline background values. As expected, the larger dose gave a several-fold higher brain signal for all the antibodies, suggesting that their brain uptake is not saturated at the lower dose. Generally, administration of the 6B2G12 antibody (nM to pM affinity) led to an approximately 2-3 fold stronger signal than: (1) the signal provided by a lower affinity (nM to µM), but more phospho-selective antibody that immunospecifically binds to the same p396,404 epitope; (2) the signal provided by a high affinity (nM) antibody that immunospecifically binds to an epitope that is distinct from the p396,404 epitope; or (3) the signal provided by a low affinity antibody that immunospecifically binds to a conformational tau epitope. These differences likely reflect both the relative prominence of these tau antibody epitopes in these animals and the affinities of the antibodies. All the antibodies evaluated showed specificity for tau pathology, resulting in a much stronger brain signal in tauopathy mice compared to a very weak brain signal in Aβ plaque-(Tg-SwDI) or wild-type mice. Limited signal was also detected with control IgG antibody. Importantly, the observed signal correlated well with the degree of tau pathology and the intravenously injected antibodies partially co-localized with stained neuronal tau aggregates (PHF1, MC1 and tau-5) and markers of endosomes, autophagosomes and lysosomes (EEA1, LC3, P62 and Rab7) as has been observed with the 6B2G12 antibody.

Overall, these findings indicate that tau antibodies against different epitopes can be used to assess epitope prominence in vivo in mouse models. Smaller antibody fragments of such imaging probes with even better brain penetration resulting in a stronger brain signal (such as scFv235) have great potential as clinical imaging ligands.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A pharmaceutical composition comprising:
   (A) a molecule capable of immunospecifically binding to phosphorylated Tau with greater selectivity than to non-phosphorylated Tau, wherein said molecule is a humanized antibody, or comprises an epitope-binding portion thereof;
   wherein said antibody and said epitope-binding portion thereof comprise:
   (1) a Light Chain CDR1 having the amino acid sequence of SEQ ID NO:12;
   (2) a Light Chain CDR2 having the amino acid sequence of SEQ ID NO:13;
   (3) a Light Chain CDR3 having the amino acid sequence of SEQ ID NO:14;
   (4) a Heavy Chain CDR1 having the amino acid sequence of SEQ ID NO:15;
   (5) a Heavy Chain CDR2 having the amino acid sequence of SEQ ID NO:16; and
   (6) a Heavy Chain CDR3 having the amino acid sequence of SEQ ID NO:17; and
   (B) a pharmaceutically acceptable carrier, diluent and/or stabilizer.

2. The pharmaceutical composition of claim 1, wherein said molecule is capable of immunospecifically binding to phosphorylated Tau and to a phosphorylated Tau peptide having the amino acid sequence of SEQ ID NO:7.

3. The pharmaceutical composition of claim 1, wherein said molecule capable of immunospecifically binding to phosphorylated Tau with greater selectivity than to non-phosphorylated Tau is an antibody.

4. The pharmaceutical composition of claim 1, wherein said molecule capable of immunospecifically binding to phosphorylated Tau with greater selectivity than to non-phosphorylated Tau is an scFv or a diabody.

5. The pharmaceutical composition of claim 1, wherein said antibody or said epitope-binding portion thereof, upon peripheral injection into a recipient, co-localizes with a Tau aggregate.

6. The pharmaceutical composition of claim 1, wherein said molecule capable of immunospecifically binding to phosphorylated Tau with greater selectivity than to non-phosphorylated Tau is an scFv.

7. The pharmaceutical composition of claim 6, wherein said molecule is an scFv, or a fusion protein thereof, and comprises an amino acid sequence selected from the group consisting of: SEQ ID NO:5, SEQ ID NO:6, SEQ ID NO:19, SEQ ID NO:20, and SEQ ID NO:21.

8. The pharmaceutical composition of claim 1, wherein said antibody or said epitope-binding portion thereof is detectably labeled.

9. The pharmaceutical composition of claim 8, wherein said detectable label is a fluorescent label, a chemoluminescent label, a paramagnetic label, a radioisotopic label or an enzyme label.

10. A kit for detecting or measuring the presence or amount of phosphorylated Tau protein in the brain of a subject, or for diagnosing Alzheimer's disease or another tauopathy in a subject, wherein said kit comprises the pharmaceutical composition of claim 8, and a solid phase to which said antibody or said epitope-binding portion thereof is bound.

11. The kit of claim 10, wherein said kit is for diagnosing a tauopathy in said subject, wherein said subject is a human subject and wherein said tauopathy is selected from the group consisting of: frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

12. A method for detecting or measuring the presence or amount of phosphorylated Tau protein in the brain, cerebrospinal fluid, blood, serum or plasma of a recipient subject, wherein said method comprises:
    (A) administering the pharmaceutical composition of claim 8 to said subject; and
    (B) detecting or measuring binding, if any, of said antibody, or said epitope-binding portion thereof, of said composition to phosphorylated Tau in the brain, cerebrospinal fluid, blood, serum or plasma of said subject.

13. The method of claim 12, wherein said detection or measurement comprises in vivo or ex vivo imaging of said binding molecule bound to said phosphorylated Tau protein.

14. The method of claim 12, wherein said detection or measurement is for diagnosing Alzheimer's disease or other tauopathy of said subject.

15. The method of claim 14, wherein said detection or measurement is for diagnosing a tauopathy in a human subject, wherein said tauopathy is selected from the group consisting of: frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

16. An in vivo medicament for the treatment of Alzheimer's disease or another tauopathy of a subject, wherein said medicament comprises the pharmaceutical composition of claim 1 in an amount effective to treat said Alzheimer's disease or other tauopathy.

17. The in vivo medicament of claim 16, wherein said medicament comprises said pharmaceutical composition in an amount effective to treat a tauopathy in said subject, wherein said subject is a human subject and said tauopathy is selected from the group consisting of: frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

18. A method for the treatment of Alzheimer's disease or other tauopathy of a subject, wherein said method comprises administering a therapeutically effective amount of the medicament of claim 16 to a subject in need thereof.

19. The method of treatment of claim 18, wherein said method is for the treatment of a tauopathy in said subject, wherein said subject is a human subject and wherein said tauopathy is selected from the group consisting of: frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, acute traumatic brain injury and chronic traumatic encephalopathy.

20. The method of claim 18, wherein said subject is a human.

\* \* \* \* \*

SEQUENCE LISTING

```
<160> NUMBER OF SEQ ID NOS: 26

<210> SEQ ID NO 1
<211> LENGTH: 441
<212> TYPE: PRT
<213> ORGANISM: Homo sapiens
<220> FEATURE:
<221> NAME/KEY: MISC_FEATURE
<222> LOCATION: (1)..(441)
<223> OTHER INFORMATION: Huamn Tau Protein

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160
```

```
Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 15
<212> TYPE: PRT
<213> ORGANISM: Artificial Sequence
<220> FEATURE:
<223> OTHER INFORMATION: Glycine-Containing Linker

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Glycine-Containing Linker

<400> SEQUENCE: 3

Gly Ser Thr Ser Gly Ser Gly Lys Pro Gly Ser Gly Glu Gly Ser Thr
```

```
Lys Gly

<210> SEQ ID NO 4
<211> LENGTH: 18
<212> TYPE: PRT
<213> ORGANISM: Artificial Sequence
<220> FEATURE:
<223> OTHER INFORMATION: Glycine-Containing Linker

<400> SEQUENCE: 4

Ser Ser Gly Gly Gly Gly Ser Gly Gly Gly Gly Gly Gly Ser Ser Arg
1               5                   10                  15

Ser Ser

<210> SEQ ID NO 5
<211> LENGTH: 6
<212> TYPE: PRT
<213> ORGANISM: Artificial Sequence
<220> FEATURE:
<223> OTHER INFORMATION: Histidine-Containing Linker ("His-Tag")

<400> SEQUENCE: 5

His His His His His His
1               5

<210> SEQ ID NO 6
<211> LENGTH: 12
<212> TYPE: PRT
<213> ORGANISM: Artificial Sequence
<220> FEATURE:
<223> OTHER INFORMATION: Human Influenza hemagglutinin (HA)-Derived
      Linker ("HA-Tag")

<400> SEQUENCE: 6

Gly Ala Tyr Pro Tyr Asp Val Pro Asp Tyr Ala Ser
1               5                   10

<210> SEQ ID NO 7
<211> LENGTH: 23
<212> TYPE: PRT
<213> ORGANISM: Homo sapiens
<220> FEATURE:
<221> NAME/KEY: MISC_FEATURE
<222> LOCATION: (1)..(23)
<223> OTHER INFORMATION: Phospho-Tau 386-408 Peptide
<220> FEATURE:
<221> NAME/KEY: MISC_FEATURE
<222> LOCATION: (11)..(11)
<223> OTHER INFORMATION: Phospho-Serine Residue
<220> FEATURE:
<221> NAME/KEY: MISC_FEATURE
<222> LOCATION: (19)..(19)
<223> OTHER INFORMATION: Phospho-Serine Residue

<400> SEQUENCE: 7

Thr Asp His Gly Ala Glu Ile Val Tyr Lys Ser Pro Val Val Ser Gly
1               5                   10                  15

Asp Thr Ser Pro Arg His Leu
            20

<210> SEQ ID NO 8
<211> LENGTH: 114
<212> TYPE: PRT
<213> ORGANISM: Mus musculus
<220> FEATURE:
<221> NAME/KEY: MISC_FEATURE
```

```
<222> LOCATION: (1)..(114)
<223> OTHER INFORMATION: Light Chain Variable Domain of Antibody 6B2G12

<400> SEQUENCE: 8

Glu Leu Asp Val Gln Met Thr Gln Thr Pro Leu Thr Leu Ser Val Thr
1               5                   10                  15

Ile Gly Gln Pro Ala Ser Ile Ser Cys Lys Ser Ser Gln Ser Leu Leu
            20                  25                  30

Tyr Ser Asn Gly Lys Thr Tyr Leu Asn Trp Leu Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Val
                85                  90                  95

Gln Gly Thr His Ser Pro Leu Thr Phe Gly Ala Gly Thr Lys Leu Glu
            100                 105                 110

Leu Lys

<210> SEQ ID NO 9
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: Heavy Chain Variable Domain of Antibody 6B2G12

<400> SEQUENCE: 9

Leu Glu Val Gln Leu Gln Gln Ser Gly Pro Glu Leu Val Lys Pro Gly
1               5                   10                  15

Ala Ser Val Lys Ile Ser Cys Lys Thr Ser Gly Tyr Thr Phe Thr Glu
            20                  25                  30

Tyr Thr Lys His Trp Val Lys Gln Ser His Gly Lys Ser Leu Glu Trp
        35                  40                  45

Ile Gly Ser Ile Asn Pro Asn Asn Gly Asp Thr Tyr Tyr Asn Gln Lys
    50                  55                  60

Phe Thr Asp Lys Ala Thr Leu Thr Val Asp Lys Ser Ser Thr Thr Ala
65                  70                  75                  80

Ser Met Glu Leu Arg Ser Leu Thr Phe Glu Asp Ser Ala Val Tyr Tyr
                85                  90                  95

Cys Ala Met Gly Asp Ser Ala Trp Phe Ala Tyr Trp Gly Gln Gly Thr
            100                 105                 110

Leu Val Thr Val Ser
        115

<210> SEQ ID NO 10
<211> LENGTH: 114
<212> TYPE: PRT
<213> ORGANISM: Mus musculus
<220> FEATURE:
<221> NAME/KEY: MISC_FEATURE
<222> LOCATION: (1)..(114)
<223> OTHER INFORMATION: Light Chain Variable Domain of scFv235

<400> SEQUENCE: 10

Glu Leu Asp Val Val Met Thr Gln Thr Pro Leu Thr Leu Ser Val Thr
1               5                   10                  15
```

```
Ile Gly Gln Pro Ala Ser Ile Ser Cys Lys Ser Ser Gln Ser Leu Leu
            20                  25                  30

Tyr Ser Asn Gly Lys Thr Tyr Leu Asn Trp Leu Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Val
                85                  90                  95

Gln Gly Thr His Ser Pro Leu Thr Phe Gly Ala Gly Thr Lys Leu Glu
            100                 105                 110

Leu Lys

<210> SEQ ID NO 11
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: Heavy Chain Variable Domain of scFv235

<400> SEQUENCE: 11

Leu Glu Val Gln Leu Gln Gln Ser Gly Pro Glu Leu Val Lys Pro Gly
1               5                   10                  15

Ala Ser Val Lys Ile Ser Cys Lys Thr Ser Glu Tyr Thr Phe Thr Glu
            20                  25                  30

Tyr Thr Lys His Trp Val Lys Gln Ser His Gly Lys Ser Leu Glu Trp
        35                  40                  45

Ile Gly Ser Ile Asn Pro Asn Asn Gly Asp Thr Tyr Tyr Asn Gln Lys
    50                  55                  60

Phe Thr Asp Lys Ala Thr Leu Thr Val Asp Lys Ser Ser Thr Thr Ala
65                  70                  75                  80

Ser Met Glu Leu Arg Ser Leu Thr Phe Glu Asp Ser Ala Val Tyr Tyr
                85                  90                  95

Cys Ala Met Gly Asp Ser Ala Trp Phe Ala Tyr Trp Gly Gln Gly Thr
            100                 105                 110

Leu Val Thr Val Ser
        115

<210> SEQ ID NO 12
<211> LENGTH: 16
<212> TYPE: PRT
<213> ORGANISM: Mus musculus
<220> FEATURE:
<221> NAME/KEY: MISC_FEATURE
<223> OTHER INFORMATION: Light Chain Variable Domain CDR1 of scFv235 and
      Antibody 6B2G12

<400> SEQUENCE: 12

Lys Ser Ser Gln Ser Leu Leu Tyr Ser Asn Gly Lys Thr Tyr Leu Asn
1               5                   10                  15

<210> SEQ ID NO 13
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
```

<223> OTHER INFORMATION: Light Chain Variable Domain CDR2 of scFv235 and
      Antibody 6B2G12

<400> SEQUENCE: 13

Leu Val Ser Lys Leu Asp Ser
1               5

<210> SEQ ID NO 14
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: Light Chain Variable Domain CDR3 of scFv235 and
      antibody 6B2G12

<400> SEQUENCE: 14

Val Gln Gly Thr His Ser Pro Leu Thr
1               5

<210> SEQ ID NO 15
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: Heavy Chain Variable Domain CDR1 of scFv235 and
      antibody 6B2G12

<400> SEQUENCE: 15

Glu Tyr Thr Phe Thr Glu Tyr Thr Lys His
1               5                   10

<210> SEQ ID NO 16
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: Heavy Chain Variable Domain CDR2 of scFv235 and
      antibody 6B2G12

<400> SEQUENCE: 16

Ser Ile Asn Pro Asn Asn Gly Asp Thr Tyr Tyr Asn Gln Lys Phe Thr
1               5                   10                  15

Asp

<210> SEQ ID NO 17
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: Heavy Chain Variable Domain CDR3 of scFv235 and
      antibody 6B2G12

<400> SEQUENCE: 17

Gly Asp Ser Ala Trp Phe Ala Tyr
1               5

<210> SEQ ID NO 18
<211> LENGTH: 250
<212> TYPE: PRT
<213> ORGANISM: Artificial Sequence

```
<220> FEATURE:
<223> OTHER INFORMATION: Amino Acid Sequence of scFv235

<400> SEQUENCE: 18

Glu Leu Asp Val Val Met Thr Gln Thr Pro Leu Thr Leu Ser Val Thr
1               5                   10                  15

Ile Gly Gln Pro Ala Ser Ile Ser Cys Lys Ser Ser Gln Ser Leu Leu
                20                  25                  30

Tyr Ser Asn Gly Lys Thr Tyr Leu Asn Trp Leu Leu Gln Arg Pro Gly
            35                  40                  45

Gln Ser Pro Lys Arg Leu Ile Tyr Leu Val Ser Lys Leu Asp Ser Gly
        50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Val
                85                  90                  95

Gln Gly Thr His Ser Pro Leu Thr Phe Gly Ala Gly Thr Lys Leu Glu
            100                 105                 110

Leu Lys Ser Ser Gly Gly Gly Ser Gly Gly Gly Gly Gly Gly Gly Ser
        115                 120                 125

Ser Arg Ser Ser Leu Glu Val Gln Leu Gln Gln Ser Gly Pro Glu Leu
    130                 135                 140

Val Lys Pro Gly Ala Ser Val Lys Ile Ser Cys Lys Thr Ser Glu Tyr
145                 150                 155                 160

Thr Phe Thr Glu Tyr Thr Lys His Trp Val Lys Gln Ser His Gly Lys
                165                 170                 175

Ser Leu Glu Trp Ile Gly Ser Ile Asn Pro Asn Asn Gly Asp Thr Tyr
            180                 185                 190

Tyr Asn Gln Lys Phe Thr Asp Lys Ala Thr Leu Thr Val Asp Lys Ser
        195                 200                 205

Ser Thr Thr Ala Ser Met Glu Leu Arg Ser Leu Thr Phe Glu Asp Ser
    210                 215                 220

Ala Val Tyr Tyr Cys Ala Met Gly Asp Ser Ala Trp Phe Ala Tyr Trp
225                 230                 235                 240

Gly Gln Gly Thr Leu Val Thr Val Ser Ala
                245                 250

<210> SEQ ID NO 19
<211> LENGTH: 28
<212> TYPE: PRT
<213> ORGANISM: Artificial Sequence
<220> FEATURE:
<223> OTHER INFORMATION: N-Terminal Leader Peptide

<400> SEQUENCE: 19

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala
                20                  25

<210> SEQ ID NO 20
<211> LENGTH: 15
<212> TYPE: PRT
<213> ORGANISM: Artificial Sequence
<220> FEATURE:
<223> OTHER INFORMATION: C-Terminal Peptide

<400> SEQUENCE: 20
```

Ala Lys Thr Thr Pro Pro Ser Val Thr Ser Gly Gln Ala Gly Gln
1               5                   10                  15

<210> SEQ ID NO 21
<211> LENGTH: 33
<212> TYPE: PRT
<213> ORGANISM: Artificial Sequence
<220> FEATURE:
<223> OTHER INFORMATION: Prefeered C-Terminal Peptide

<400> SEQUENCE: 21

Ala Lys Thr Thr Pro Pro Ser Val Thr Ser Gly Gln Ala Gly Gln His
1               5                   10                  15

His His His His His Gly Ala Tyr Pro Tyr Asp Val Pro Asp Tyr Ala
            20                  25                  30

Ser

<210> SEQ ID NO 22
<211> LENGTH: 278
<212> TYPE: PRT
<213> ORGANISM: Artificial Sequence
<220> FEATURE:
<223> OTHER INFORMATION: scFv235 Fusion Protein Comprising N-Terminal
      Leader Peptide Portion (SEQ ID NO:19) and scFv235 (SEQ ID NO:18)

<400> SEQUENCE: 22

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Glu Leu Asp Val
            20                  25                  30

Val Met Thr Gln Thr Pro Leu Thr Leu Ser Val Thr Ile Gly Gln Pro
        35                  40                  45

Ala Ser Ile Ser Cys Lys Ser Ser Gln Ser Leu Leu Tyr Ser Asn Gly
    50                  55                  60

Lys Thr Tyr Leu Asn Trp Leu Leu Gln Arg Pro Gly Gln Ser Pro Lys
65                  70                  75                  80

Arg Leu Ile Tyr Leu Val Ser Lys Leu Asp Ser Gly Val Pro Asp Arg
                85                  90                  95

Phe Thr Gly Ser Gly Ser Gly Thr Asp Phe Thr Leu Lys Ile Ser Arg
            100                 105                 110

Val Glu Ala Glu Asp Leu Gly Val Tyr Tyr Cys Val Gln Gly Thr His
        115                 120                 125

Ser Pro Leu Thr Phe Gly Ala Gly Thr Lys Leu Glu Leu Lys Ser Ser
    130                 135                 140

Gly Gly Gly Gly Ser Gly Gly Gly Gly Ser Ser Arg Ser Ser
145                 150                 155                 160

Leu Glu Val Gln Leu Gln Gln Ser Gly Pro Glu Leu Val Lys Pro Gly
                165                 170                 175

Ala Ser Val Lys Ile Ser Cys Lys Thr Ser Glu Tyr Thr Phe Thr Glu
            180                 185                 190

Tyr Thr Lys His Trp Val Lys Gln Ser His Gly Lys Ser Leu Glu Trp
        195                 200                 205

Ile Gly Ser Ile Asn Pro Asn Asn Gly Asp Thr Tyr Tyr Asn Gln Lys
    210                 215                 220

Phe Thr Asp Lys Ala Thr Leu Thr Val Asp Lys Ser Ser Thr Thr Ala
225                 230                 235                 240

Ser Met Glu Leu Arg Ser Leu Thr Phe Glu Asp Ser Ala Val Tyr Tyr
                245                 250                 255

```
Cys Ala Met Gly Asp Ser Ala Trp Phe Ala Tyr Trp Gly Gln Gly Thr
            260                 265                 270

Leu Val Thr Val Ser Ala
        275
```

<210> SEQ ID NO 23
<211> LENGTH: 265
<212> TYPE: PRT
<213> ORGANISM: Artificial Sequence
<220> FEATURE:
<223> OTHER INFORMATION: scFv235 Fusion Protein Comprising scFv235 (SEQ
      ID NO:18) and C-Terminal Peptide Portion (SEQ ID NO:20)

<400> SEQUENCE: 23

```
Glu Leu Asp Val Val Met Thr Gln Thr Pro Leu Thr Leu Ser Val Thr
1               5                   10                  15

Ile Gly Gln Pro Ala Ser Ile Ser Cys Lys Ser Ser Gln Ser Leu Leu
            20                  25                  30

Tyr Ser Asn Gly Lys Thr Tyr Leu Asn Trp Leu Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Val
                85                  90                  95

Gln Gly Thr His Ser Pro Leu Thr Phe Gly Ala Gly Thr Lys Leu Glu
            100                 105                 110

Leu Lys Ser Ser Gly Gly Gly Ser Gly Gly Gly Gly Gly Gly Gly Ser
        115                 120                 125

Ser Arg Ser Ser Leu Glu Val Gln Leu Gln Gln Ser Gly Pro Glu Leu
    130                 135                 140

Val Lys Pro Gly Ala Ser Val Lys Ile Ser Cys Lys Thr Ser Glu Tyr
145                 150                 155                 160

Thr Phe Thr Glu Tyr Thr Lys His Trp Val Lys Gln Ser His Gly Lys
                165                 170                 175

Ser Leu Glu Trp Ile Gly Ser Ile Asn Pro Asn Asn Gly Asp Thr Tyr
            180                 185                 190

Tyr Asn Gln Lys Phe Thr Asp Lys Ala Thr Leu Thr Val Asp Lys Ser
        195                 200                 205

Ser Thr Thr Ala Ser Met Glu Leu Arg Ser Leu Thr Phe Glu Asp Ser
    210                 215                 220

Ala Val Tyr Tyr Cys Ala Met Gly Asp Ser Ala Trp Phe Ala Tyr Trp
225                 230                 235                 240

Gly Gln Gly Thr Leu Val Thr Val Ser Ala Ala Lys Thr Thr Pro Pro
                245                 250                 255

Ser Val Thr Ser Gly Gln Ala Gly Gln
            260                 265
```

<210> SEQ ID NO 24
<211> LENGTH: 282
<212> TYPE: PRT
<213> ORGANISM: Artificial Sequence
<220> FEATURE:
<223> OTHER INFORMATION: scFv235 Fusion Protein Comprising scFv235 (SEQ
      ID NO:18) and Preferred C-Terminal Peptide Portion (SEQ ID NO:21)

<400> SEQUENCE: 24

```
Glu Leu Asp Val Val Met Thr Gln Thr Pro Leu Thr Leu Ser Val Thr
1               5                   10                  15

Ile Gly Gln Pro Ala Ser Ile Ser Cys Lys Ser Ser Gln Ser Leu Leu
            20                  25                  30

Tyr Ser Asn Gly Lys Thr Tyr Leu Asn Trp Leu Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Val
                85                  90                  95

Gln Gly Thr His Ser Pro Leu Thr Phe Gly Ala Gly Thr Lys Leu Glu
            100                 105                 110

Leu Lys Ser Ser Gly Gly Gly Ser Gly Gly Gly Gly Ser
        115                 120                 125

Ser Arg Ser Ser Leu Glu Val Gln Leu Gln Gln Ser Gly Pro Glu Leu
    130                 135                 140

Val Lys Pro Gly Ala Ser Val Lys Ile Ser Cys Lys Thr Ser Glu Tyr
145                 150                 155                 160

Thr Phe Thr Glu Tyr Thr Lys His Trp Val Lys Gln Ser His Gly Lys
                165                 170                 175

Ser Leu Glu Trp Ile Gly Ser Ile Asn Pro Asn Asn Gly Asp Thr Tyr
            180                 185                 190

Tyr Asn Gln Lys Phe Thr Asp Lys Ala Thr Leu Thr Val Asp Lys Ser
        195                 200                 205

Ser Thr Thr Ala Ser Met Glu Leu Arg Ser Leu Thr Phe Glu Asp Ser
    210                 215                 220

Ala Val Tyr Tyr Cys Ala Met Gly Asp Ser Ala Trp Phe Ala Tyr Trp
225                 230                 235                 240

Gly Gln Gly Thr Leu Val Thr Val Ser Ala Lys Thr Thr Pro Pro Ser
                245                 250                 255

Val Thr Ser Gly Gln Ala Gly Gln His His His His His His Gly Ala
            260                 265                 270

Tyr Pro Tyr Asp Val Pro Asp Tyr Ala Ser
        275                 280

<210> SEQ ID NO 25
<211> LENGTH: 293
<212> TYPE: PRT
<213> ORGANISM: Artificial Sequence
<220> FEATURE:
<223> OTHER INFORMATION: scFv235 Fusion Protein Comprising N-Terminal
      Leader Peptide Portion (SEQ ID NO:19), scFv235 (SEQ ID NO:18) and
      C-Terminal Peptide Portion (SEQ ID NO:20)

<400> SEQUENCE: 25

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala Glu Leu Asp Val
            20                  25                  30

Val Met Thr Gln Thr Pro Leu Thr Leu Ser Val Thr Ile Gly Gln Pro
        35                  40                  45

Ala Ser Ile Ser Cys Lys Ser Ser Gln Ser Leu Leu Tyr Ser Asn Gly
    50                  55                  60
```

```
Lys Thr Tyr Leu Asn Trp Leu Leu Gln Arg Pro Gly Gln Ser Pro Lys
 65                  70                  75                  80

Arg Leu Ile Tyr Leu Val Ser Lys Leu Asp Ser Gly Val Pro Asp Arg
             85                  90                  95

Phe Thr Gly Ser Gly Ser Gly Thr Asp Phe Thr Leu Lys Ile Ser Arg
            100                 105                 110

Val Glu Ala Glu Asp Leu Gly Val Tyr Tyr Cys Val Gln Gly Thr His
            115                 120                 125

Ser Pro Leu Thr Phe Gly Ala Gly Thr Lys Leu Glu Leu Lys Ser Ser
        130                 135                 140

Gly Gly Gly Gly Ser Gly Gly Gly Gly Ser Ser Arg Ser Ser
145                 150                 155                 160

Leu Glu Val Gln Leu Gln Gln Ser Gly Pro Glu Leu Val Lys Pro Gly
                165                 170                 175

Ala Ser Val Lys Ile Ser Cys Lys Thr Ser Glu Tyr Thr Phe Thr Glu
                180                 185                 190

Tyr Thr Lys His Trp Val Lys Gln Ser His Gly Lys Ser Leu Glu Trp
            195                 200                 205

Ile Gly Ser Ile Asn Pro Asn Asn Gly Asp Thr Tyr Tyr Asn Gln Lys
210                 215                 220

Phe Thr Asp Lys Ala Thr Leu Thr Val Asp Lys Ser Ser Thr Thr Ala
225                 230                 235                 240

Ser Met Glu Leu Arg Ser Leu Thr Phe Glu Asp Ser Ala Val Tyr Tyr
                245                 250                 255

Cys Ala Met Gly Asp Ser Ala Trp Phe Ala Tyr Trp Gly Gln Gly Thr
            260                 265                 270

Leu Val Thr Val Ser Ala Ala Lys Thr Thr Pro Pro Ser Val Thr Ser
        275                 280                 285

Gly Gln Ala Gly Gln
        290

<210> SEQ ID NO 26
<211> LENGTH: 311
<212> TYPE: PRT
<213> ORGANISM: Artificial Sequence
<220> FEATURE:
<223> OTHER INFORMATION: scFv235 Fusion Protein Comprising N-Terminal
      Leader Peptide Portion (SEQ ID NO:19), scFv235 (SEQ ID NO:18) and
      Preferred C-Terminal Peptide Portion (SEQ ID NO:21)

<400> SEQUENCE: 26

Ile Gln Glu Glu Phe Lys Met Lys Lys Thr Ala Ile Ala Ile Ala Val
 1               5                  10                  15

Ala Leu Ala Gly Phe Ala Thr Val Ala Gln Ala Ala Glu Leu Asp Val
             20                  25                  30

Val Met Thr Gln Thr Pro Leu Thr Leu Ser Val Thr Ile Gly Gln Pro
         35                  40                  45

Ala Ser Ile Ser Cys Lys Ser Ser Gln Ser Leu Leu Tyr Ser Asn Gly
     50                  55                  60

Lys Thr Tyr Leu Asn Trp Leu Leu Gln Arg Pro Gly Gln Ser Pro Lys
 65                  70                  75                  80

Arg Leu Ile Tyr Leu Val Ser Lys Leu Asp Ser Gly Val Pro Asp Arg
             85                  90                  95

Phe Thr Gly Ser Gly Ser Gly Thr Asp Phe Thr Leu Lys Ile Ser Arg
            100                 105                 110

Val Glu Ala Glu Asp Leu Gly Val Tyr Tyr Cys Val Gln Gly Thr His
```

```
                         -continued
            115               120             125
Ser Pro Leu Thr Phe Gly Ala Gly Thr Lys Leu Glu Leu Lys Ser Ser
        130             135             140

Gly Gly Gly Gly Ser Gly Gly Gly Gly Ser Ser Arg Ser Ser
145             150             155             160

Leu Glu Val Gln Leu Gln Gln Ser Gly Pro Glu Leu Val Lys Pro Gly
                165             170             175

Ala Ser Val Lys Ile Ser Cys Lys Thr Ser Glu Tyr Thr Phe Thr Glu
            180             185             190

Tyr Thr Lys His Trp Val Lys Gln Ser His Gly Lys Ser Leu Glu Trp
        195             200             205

Ile Gly Ser Ile Asn Pro Asn Asn Gly Asp Thr Tyr Tyr Asn Gln Lys
    210             215             220

Phe Thr Asp Lys Ala Thr Leu Thr Val Asp Lys Ser Ser Thr Thr Ala
225             230             235             240

Ser Met Glu Leu Arg Ser Leu Thr Phe Glu Asp Ser Ala Val Tyr Tyr
                245             250             255

Cys Ala Met Gly Asp Ser Ala Trp Phe Ala Tyr Trp Gly Gln Gly Thr
            260             265             270

Leu Val Thr Val Ser Ala Ala Lys Thr Thr Pro Pro Ser Val Thr Ser
        275             280             285

Gly Gln Ala Gly Gln His His His His His His Gly Ala Tyr Pro Tyr
    290             295             300

Asp Val Pro Asp Tyr Ala Ser
305             310
```